US012624364B2

(12) United States Patent
To et al.

(10) Patent No.: US 12,624,364 B2
(45) Date of Patent: May 12, 2026

(54) PLANT REGULATORY ELEMENTS AND USES THEREOF FOR AUTOEXCISION

(71) Applicant: Monsanto Technology LLC, St. Louis, MO (US)

(72) Inventors: Pokchun Jennifer To, Wildwood, MO (US); Zarir Vaghchhipawala, Madison, WI (US); Xudong Ye, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 119 days.

(21) Appl. No.: 18/032,313

(22) PCT Filed: Oct. 19, 2021

(86) PCT No.: PCT/US2021/055596
§ 371 (c)(1),
(2) Date: Apr. 17, 2023

(87) PCT Pub. No.: WO2022/086951
PCT Pub. Date: Apr. 28, 2022

(65) Prior Publication Data
US 2024/0035039 A1     Feb. 1, 2024

Related U.S. Application Data

(60) Provisional application No. 63/093,893, filed on Oct. 20, 2020.

(51) Int. Cl.
| | |
|---|---|
| *C12N 15/82* | (2006.01) |
| *C12N 9/12* | (2006.01) |
| *C12N 9/22* | (2006.01) |

(52) U.S. Cl.
CPC ....... *C12N 15/8216* (2013.01); *C12N 9/1241* (2013.01); *C12N 9/22* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 8,362,319 B2 * | 1/2013 | Andre | ..................... | A01H 1/06 |
| | | | | 800/298 |
| 9,631,197 B2 | 4/2017 | Los et al. | | |
| 2002/0147168 A1 | 10/2002 | Surin et al. | | |
| 2018/0213800 A1 * | 8/2018 | Djonovic | ............... | A01N 63/36 |
| 2020/0056196 A1 | 2/2020 | Davis et al. | | |

OTHER PUBLICATIONS

Grimwood (EST Accession No. GS978664, version GS978664.1, published online May 3, 2010). (Year: 2010).*

Feng, et al. "A Highly Efficient Cell Division-Specific CRISPR/Cas9 System Generates Homozygous Mutants for Multiple Genes in *Arabidopsis*." Int. J. Mol. Sci., 19(12), 3925, (2018).

Wang, et al. "Recombinase technology: applications and possibilities." Plant Cell Reports, vol. 30, pp. 267-285, (2011).

Ye, et al. "Cre-mediated autoexcision of selectable marker genes in soybean, cotton, canola and maize transgenic plants." Plant Cell Reports, vol. 42, pp. 45-55, (2023).

International Search Report and Written Opinion for International Application No. PCT/US2021/055596 mailed Feb. 28, 2022.

Komari, et al. Vectors carrying two separate T-DNAs for co-transformation of higher plants mediated by Agrobacterium tumefaciens and segregation of transformants free from selection markers, The Plant Journal, 10(1):165-174, (1996).

Lyznik, et al. Gene Transfer Mediated by Site-Specific Recombination Systems. In: Gelvin, S.B., Schilperoort, R.A. (eds) Plant Molecular Biology Manual. Springer, Dordrecht, (2000).

Machida, et al. Use of the R-RS Site-Specific Recombination System in Plants. In: Gelvin, S.B., Schilperoort, R.A. (eds) Plant Molecular Biology Manual. Springer, Dordrecht, (2000).

Maeser, S. et al. The Gin recombinase of phage Mu can catalyse site-specific recombination in plant protoplasts. Molec. Gen. Genet. 230, 170-176 (1991).

Nakagawa et al., Diversity of preferred nucleotide sequences around the translation initiation codon in eukaryote genomes, Nucleic Acids Research, vol. 36, Issue 3, pp. 861-871, (2008).

Van Ex et al. Evaluation of seven promoters to achieve germline directed Cre-lox recombination in *Arabidopsis thaliana* Plant Cell Rep 28, 1509-1520, (2009).

GenBank Accession No. X04753. "Potato light-inducible tissue-specific ST-LS1 gene". Dated Nov. 14, 2006.

Invitation to Pay Additional Fees regarding International App. No. PCT/US21/55596 mailed Dec. 21, 2021.

* cited by examiner

*Primary Examiner* — Charles Logsdon
*Assistant Examiner* — Jessica Nicole Stockdale
(74) *Attorney, Agent, or Firm* — Dentons US LLP

(57) ABSTRACT

Recombinant DNA molecules and constructs are provided that are useful for modulating gene expression in plants. One or more expression cassette(s) of a recombinant DNA molecule or construct may be excised from transgenic plants following transformation by the presence of flanking site-specific recombination sites in the recombinant DNA molecule or construct by expression of a recombinase enzyme encoded by the recombinant DNA molecule or construct. Such a recombinase system may be used to remove such expression cassette(s) from plants transformed with the recombinant DNA construct or vector. The recombinase transgene may be operably linked to a tissue-preferred or tissue-specific promoter for autoexcision in transformed plants without crossing to a different transgenic line expressing the recombinase. Methods for causing autoexcision of one or more expression cassette(s) in a transgenic plant, and plants and cells containing or transformed with a recombinant DNA molecule or construct of the present disclosure, are also provided.

27 Claims, No Drawings
Specification includes a Sequence Listing.

SEQUENCE LISTING

```
<160> NUMBER OF SEQ ID NOS: 67

<210> SEQ ID NO 1
<211> LENGTH: 2810
<212> TYPE: DNA
<213> ORGANISM: Artificial
<220> FEATURE:
<223> OTHER INFORMATION: DNA sequence of an EXP,
      EXP-Zm.Cdc45-1+Zm.DnaK:1:1 comprising a promoter (P-Zm.Cdc45-1:8)
      operably linked 5' to a leader (L-Zm.Cdc45-1:1), operably linked
      5' to an intron (I-Zm.DnaK:1).

<400> SEQUENCE: 1
agccacatgc agtgaattct atactcgatg cggaaattca tttgtgccca aggtgacact        60
gatagggagg atcatcgcga ggatatcgca ataaaaactt cttcgggttt gaggtgaatt       120
gagagaattg gaagggatca aatcccttcc tatatgaatt tatataggag gcgatttaat       180
cccctctaat ccctctcaat taattcacct ctaatcagag attggtctat gtgagcttga       240
tagaggagat ctgcatttgt ctcgaatgtg tgtggagaga ggaggttgag gctagcccca       300
```

-continued

```
ccattgaaca gggcatgccc gactttgacg ttactgatga tgaagctaca aggggcaaaa    360
ttcgtgtgcc tgccatgctg ctaggacaag cagaggagtc aaaggagatg gaggtatcga    420
attcgtagga tagcggcttg agatggtttt tacattggtt caggaagtcc cctacgtaca    480
atttgatctt aaaatctttg ttgctgattg gaggtcttac caggcggagc acatatctcc    540
cgtgcttgtg tgaagtactc gctactgtca tgcttgctag ttccagtgcc tcgatgctaa    600
gtttgctggg ttctatgaga ggcttgttcc ccgtatatag tccaacgagt aggtagctct    660
gcccctctcc tttccgttgg acaatagatg tgatatccta ttcaggtgga ttgtatgata    720
ttctggccca aggtttaata ggattgatat aatacttata ccaacaatgt ctatcttctt    780
ttttggaagc ctatcttaaa agaatctctg ggttaaggat cttggtctag agaagttttc    840
ccggtgcgca cgagtgaggg caaaatacgt ataaaaactc gtgttggtca gttaggatat    900
tttatgatta tagagagcta ccagaaataa gtactacagg tgtgagagtg gactagatgt    960
tacaacagac accatgtgca aaggtgaagt aatgatgaag aaagaggtga gtccacttgt    1020
cggtaagaga ttacgagagt tgtatgtgaa ggactatgga tggcatatgt ggttcgctca    1080
acattccccc cccccccaaa atgtacaatt gctcaactaa gcaactattg accttcaact    1140
tagggagtgt ttgatactgc tctgtgttcc atctttatca tgaagctgcg gcgtataata    1200
gaaaattaaa cggtttttaga aaatattttt aatctaaata agaaacaaaa tgacttatct    1260
aaatgtcttc tgaaagtttg caacttcagc ttcacgattt tctgaaactc ctcatgacat    1320
gtttcatcaa cttcactaga ttttgtgaag ctgaagcaat tccaaacaga tcctaacaac    1380
atattattca tatcccacca attacatatt caaccaaagg acaaaccagc acattcactt    1440
gatcaatttc ttggatcaat tcagaaagac taagatgttc taataaggct atctctacca    1500
ccttactcat tcctcagcac ctattccgaa ctctagtgtt tttcatagtc atatgcacga    1560
tctactcacc ataccctaag actgtgtcca gcaattcacc catatggtca tctaaactgt    1620
tttgcactat aaatttgttg tccataaaac agagtttgaa tatggttata gagatgagat    1680
atcctattaa gatagacctg ggccgagtcg acaagccatg gtagccgact tcataagtgt    1740
gcaggtccgc ccacgatcgg aaggaccctc gtgccatgag aaatccaaat tttttgcttg    1800
gcgatggcgg ccttcgactt ctctcccaaa ttcaaatttc aaatccaccc aaatcccaat    1860
ttcaccgatc cccgcgcgcc ctcacagaaa gctcccgccg ccacaacatt cctcagatcc    1920
cttgaattcc ttcaacctct ccgagctccg acaattccat gatggccctc tcgatccgac    1980
ctagctgatt gatgaggcac ggaccgaccg tcttcggtac gcgctcactc cgccctctgc    2040
ctttgttact gccacgtttc tctgaatgct ctcttgtgtg gtgattgctg agagtggttt    2100
agctggatct agaattacac tctgaaatcg tgttctgcct gtgctgatta cttgccgtcc    2160
tttgtagcag caaaatatag ggacatggta gtacgaaacg aagatagaac ctacacagca    2220
atacgagaaa tgtgtaattt ggtgcttagc ggtatttatt taagcacatg ttggtgttat    2280
agggcacttg gattcagaag tttgctgtta atttaggcac aggcttcata ctacatgggt    2340
caatagtata gggattcata ttataggcga tactataata atttgttcgt ctgcagagct    2400
tattatttgc caaaattaga tattcctatt ctgtttttgt ttgtgtgctg ttaaattgtt    2460
aacgcctgaa ggaataaata taaatgacga aattttgatg tttatctctg ctcctttatt    2520
gtgaccataa gtcaagatca gatgcacttg ttttaaatat tgttgtctga agaaataagt    2580
actgacagta ttttgatgca ttgatctgct tgtttgttgt aacaaaattt aaaaataaag    2640
agtttccttt ttgttgctct ccttacctcc tgatggtatc tagtatctac caactgacac    2700
```

-continued

```
tatattgctt ctctttacat acgtatcttg ctcgatgcct tctccctagt gttgaccagt    2760
gttactcaca tagtctttgc tcatttcatt gtaatgcaga taccaagcgg             2810
```

<210> SEQ ID NO 2
<211> LENGTH: 1887
<212> TYPE: DNA
<213> ORGANISM: Zea mays
<220> FEATURE:
<221> NAME/KEY: misc_feature
<222> LOCATION: (1)..(1887)
<223> OTHER INFORMATION: DNA sequence of a promoter, P-Zm.Cdc45-1:8.

<400> SEQUENCE: 2

```
agccacatgc agtgaattct atactcgatg cggaaattca tttgtgccca aggtgacact      60
gatagggagg atcatcgcga ggatatcgca ataaaaactt cttcgggttt gaggtgaatt     120
gagagaattg gaagggatca aatcccttcc tatatgaatt tatataggag gcgatttaat     180
cccctctaat ccctctcaat taattcacct ctaatcagag attggtctat gtgagcttga     240
tagaggagat ctgcatttgt ctcgaatgtg tgtggagaga ggaggttgag gctagcccca     300
ccattgaaca gggcatgccc gactttgacg ttactgatga tgaagctaca aggggcaaaa     360
ttcgtgtgcc tgccatgctg ctaggacaag cagaggagtc aaaggagatg gaggtatcga     420
attcgtagga tagcggcttg agatggtttt tacattggtt caggaagtcc cctacgtaca     480
atttgatctt aaaatctttg ttgctgattg gaggtcttac caggcggagc acatatctcc     540
cgtgcttgtg tgaagtactc gctactgtca tgcttgctag ttccagtgcc tcgatgctaa     600
gtttgctggg ttctatgaga ggcttgttcc ccgtatatag tccaacgagt aggtagctct     660
gcccctctcc tttccgttgg acaatagatg tgatatccta ttcaggtgga ttgtatgata     720
ttctggccca aggtttaata ggattgatat aatacttata ccaacaatgt ctatcttctt     780
ttttggaagc ctatcttaaa agaatctctg ggttaaggat cttggtctag agaagttttc     840
ccggtgcgca cgagtgaggg caaaatacgt ataaaaactc gtgttggtca gttaggatat     900
tttatgatta tagagagcta ccagaaataa gtactacagg tgtgagagtg gactagatgt     960
tacaacagac accatgtgca aaggtgaagt aatgatgaag aaagaggtga gtccacttgt    1020
cggtaagaga ttacgagagt tgtatgtgaa ggactatgga tggcatatgt ggttcgctca    1080
acattccccc ccccccaaa atgtacaatt gctcaactaa gcaactattg accttcaact    1140
tagggagtgt ttgatactgc tctgtgttcc atctttatca tgaagctgcg gcgtataata    1200
gaaaattaaa cggtttttaga aaatattttt aatctaaata agaaacaaaa tgacttatct    1260
aaatgtcttc tgaaagtttg caacttcagc ttcacgattt tctgaaactc ctcatgacat    1320
gtttcatcaa cttcactaga ttttgtgaag ctgaagcaat tccaaacaga tcctaacaac    1380
atattattca tatcccacca attacatatt caaccaaagg acaaaccagc acattcactt    1440
gatcaatttc ttggatcaat tcagaaagac taagatgttc taataaggct atctctacca    1500
ccttactcat tcctcagcac ctattccgaa ctctagtgtt tttcatagtc atatgcacga    1560
tctactcacc ataccctaag actgtgtcca gcaattcacc catatggtca tctaaactgt    1620
tttgcactat aaatttgttg tccataaaac agagtttgaa tatggttata gagatgagat    1680
atcctattaa gatagacctg gccgagtcg acaagccatg gtagccgact tcataagtgt    1740
gcaggtccgc ccacgatcgg aaggaccctc gtgccatgag aaatccaaat tttttgcttg    1800
gcgatggcgg ccttcgactt ctctcccaaa ttcaaatttc aaatccaccc aaatcccaat    1860
```

```
ttcaccgatc cccgcgcgcc ctcacag                                    1887

<210> SEQ ID NO 3
<211> LENGTH: 112
<212> TYPE: DNA
<213> ORGANISM: Zea mays
<220> FEATURE:
<221> NAME/KEY: misc_feature
<222> LOCATION: (1)..(112)
<223> OTHER INFORMATION: DNA sequence of a leader, L-Zm.Cdc45-1:1.

<400> SEQUENCE: 3
aaagctcccg ccgccacaac attcctcaga tcccttgaat tccttcaacc tctccgagct      60
ccgacaattc catgatggcc ctctcgatcc gacctagctg attgatgagg ca            112

<210> SEQ ID NO 4
<211> LENGTH: 1957
<212> TYPE: DNA
<213> ORGANISM: Oryza sativa
<220> FEATURE:
<221> NAME/KEY: misc_feature
<222> LOCATION: (1)..(1957)
<223> OTHER INFORMATION: DNA sequence of an EXP, EXP-Os.Cdc45-1:1:1
      comprising a promoter (P-Os.Cdc45-1-1:1:1), operably linked 5' to
      a leader (L-Os.Cdc45-1-1:1:1).

<400> SEQUENCE: 4
acatacatct gtctagattc attaatattt aaatgaatgt gggtaatgtt agaaagtctt      60
acattgtgaa acggataaag tattagttaa aagttagtat atatgaactt gtaaaacgct     120
catttgatgt atgaacttgt ttgacgcgtg tgaaccaaag ttaaaatgac accgaaaggc     180
taatcttact aacttgtcgt tgattaggac ttgaggtggc atgcatgaga cattatattt     240
gaaatcttag tctctatttt ctctttctat gtttctacta cttgcatcat tttgtttttgg    300 tttttcatat cttttttgttt acgattatta ttatgtctta tactatattt tttattgaat    360
tgatgtgtgt ctatctagta ttttttctcat ctactatatc ctttctttaa agagtgtatt    420
tttagatatg aagattgaca aggacaatat gtgagaacaa ttaactacta atactatata    480
tacattcaag ataaaaacct gacagattaa tttaccgcaa gttaaattta ctcctcacta    540
taatcaattt aagcatagtt caacatgtaa atagaagtgg taaatcgttc tctcgactga    600
tgtggcccca aaccgaaagc tcacacaact caaatgagtt ccatccaatt ttgcgaggag    660
tacctagcgt gtgaaactag agctacaatc ttggattcag cgctactcct actagcttag     720
cttgggcccg ttcgtaccaa ataataggag gcggcatgca ggtatgccaa aacacatatt     780
ggagctagca atagcaacag ttcttttttgc agctcaacat gtatatccaa tcaactaatg     840
tctcgacttt gaacatgatt ggtttgtgta tatattcagg tatgtagata tagataatat    900
ttgtaatttt cgaatcaact catgcacata caacatgcaa aagctagtag tatttgatct    960
catcacttac tgggcctaca tgctgataat cctcagtaat ccatggccat tcagacatgg   1020
aaaatgaccc ctttaactcc gttaactagt ggatggatct aatttgtatc ccttaatcgg   1080
aaaacaagat atgccgactt gtccaactat taaacggtcc aaaacgacta tcgttgacga   1140
gacatccacg tggtagtcca atcacaaaat aaattaaaaa aaataaaatg gagcccgcat   1200
gccattcctt ctctctatca atctctctct ctctccctat caagcgcagc aggacgtaag   1260
gatgtaagtg ggtagtcccg ctacccacat aaaatctatt tgctagtata ttttttatat   1320
ggtgctacaa aatttagaag aaaaaataaa cgaagtgaga taagcgggct aaaaaacccca   1380 cttgcccgcc ccgcttgcat ccctagcagg gcagggttct cctctttctc ccctcctaac   1440
```

-continued

```
cccttccgca ctggcgttgg cggcggagtg gccggccgag tggggatgcg gggtggcgcg    1500
ggaggaggga gaggacggag cggcgacgtt tgggggggaag aagtgcaggc ctacgacgca    1560
ggtgacgatc cgccggacca aggcaggcag aactgggccg gaacgccacc gcggcttacg    1620
tgaagcccat attacttggg ccggaacgga gttgcggttt acgtgcggcc caagagcaat    1680
tcttctacga cggcctacga gcaatcggct ccacatgtcg gtcactgaaa cttcgctgtg    1740
gttcgaatcg tgagatcccc aaatacccaa tttcgatcga gtggtttccc tcccaaaccc    1800
aaaatttccg aattcctccc cgcgctgccc cgctccaacc caaattcaat tccccatttc    1860
acctcttctt ctctttgtcc ccttctccat ttccaaattc ctatccattc ctcccagatc    1920
cccaatcctc caattcacca cttcgattga tgcgcca                             1957
```

```
<210> SEQ ID NO 5
<211> LENGTH: 1871
<212> TYPE: DNA
<213> ORGANISM: Oryza sativa
<220> FEATURE:
<221> NAME/KEY: misc_feature
<222> LOCATION: (1)..(1871)
<223> OTHER INFORMATION: DNA sequence of a promoter, P-Os.Cdc45-1-1:1:1.

<400> SEQUENCE: 5
```

```
acatacatct gtctagattc attaatattt aaatgaatgt gggtaatgtt agaaagtctt      60
acattgtgaa acggataaag tattagttaa aagttagtat atatgaactt gtaaaacgct     120
catttgatgt atgaacttgt ttgacgcgtg tgaaccaaag ttaaaatgac accgaaaggc     180
taatcttact aacttgtcgt tgattaggac ttgaggtggc atgcatgaga cattatattt     240
gaaatcttag tctctatttt ctctttctat gtttctacta cttgcatcat tttgtttttgg     300 tttttcatat cttttttgttt acgattatta ttatgtctta tactatattt tttattgaat     360
tgatgtgtgt ctatctagta ttttttctcat ctactatatc ctttctttaa agagtgtatt     420
tttagatatg aagattgaca aggacaatat gtgagaacaa ttaactacta atactatata     480
tacattcaag ataaaaacct gacagattaa tttaccgcaa gttaaattta ctcctcacta     540
taatcaattt aagcatagtt caacatgtaa atagaagtgg taaatcgttc tctcgactga     600
tgtggcccca aaccgaaagc tcacacaact caaatgagtt ccatccaatt ttgcgaggag     660
tacctagcgt gtgaaactag agctacaatc ttggattcag cgctactcct actagcttag     720
cttgggcccg ttcgtaccaa ataataggag gcggcatgca ggtatgccaa aacacatatt     780
ggagctagca atagcaacag ttcttttttgc agctcaacat gtatatccaa tcaactaatg     840
tctcgacttt gaacatgatt ggtttgtgta tatattcagg tatgtagata tagataaatat     900 ttgtaatttt cgaatcaact catgcacata caacatgcaa aagctagtag tatttgatct     960
catcacttac tgggcctaca tgctgataat cctcagtaat ccatggccat tcagacatgg    1020
aaaatgaccc ctttaactcc gttaactagt ggatggatct aatttgtatc ccttaatcgg    1080
aaaacaagat atgccgactt gtccaactat taaacggtcc aaaacgacta tcgttgacga    1140
gacatccacg tggtagtcca atcacaaaat aaattaaaaa aaataaaatg gagcccgcat    1200
gccattcctt ctctctatca atctctctct ctctccctat caagcgcagc aggacgtaag    1260
gatgtaagtg ggtagtcccg ctacccacat aaaatctatt tgctagtata ttttttatat    1320
ggtgctacaa aatttagaag aaaaaataaa cgaagtgaga taagcgggct aaaaaaccca    1380
cttgcccgcc ccgcttgcat ccctagcagg gcagggttct cctctttctc ccctcctaac    1440
```

-continued

```
ccccttccgca ctggcgttgg cggcggagtg gccggccgag tggggatgcg gggtggcgcg   1500
ggaggaggga gaggacggag cggcgacgtt tggggggaag aagtgcaggc ctacgacgca   1560
ggtgacgatc cgccggacca aggcaggcag aactgggccg gaacgccacc gcggcttacg   1620
tgaagcccat attacttggg ccggaacgga gttgcggttt acgtgcggcc caagagcaat   1680
tcttctacga cggcctacga gcaatcggct ccacatgtcg gtcactgaaa cttcgctgtg   1740
gttcgaatcg tgagatcccc aaatacccaa tttcgatcga gtggtttccc tcccaaaccc   1800
aaaatttccg aattcctccc cgcgctgccc cgctccaacc caaattcaat tccccatttc   1860
acctcttctt c                                                        1871

<210> SEQ ID NO 6
<211> LENGTH: 86
<212> TYPE: DNA
<213> ORGANISM: Oryza sativa
<220> FEATURE:
<221> NAME/KEY: misc_feature
<222> LOCATION: (1)..(86)
<223> OTHER INFORMATION: DNA sequence of a leader, L-Zm.Cdc45-1:1.

<400> SEQUENCE: 6
tctttgtccc cttctccatt tccaaattcc tatccattcc tcccagatcc ccaatcctcc        60
aattcaccac ttcgattgat gcgcca                                             86

<210> SEQ ID NO 7
<211> LENGTH: 1434
<212> TYPE: DNA
<213> ORGANISM: Arabidopsis thaliana
<220> FEATURE:
<221> NAME/KEY: misc_feature
<222> LOCATION: (1)..(1434)
<223> OTHER INFORMATION: DNA sequence of an EXP, EXP-At.mei1 comprised
      of a promoter and leader.

<400> SEQUENCE: 7
ttcagatgta agttcctctc caacctttat attttgccat tctttgtcta tttgctttcc        60
agatccattc aaaaacatta gactagacct tgcctaatat tcaagattgt ttaccaaacc       120
ttcctgattg attttctttt ggatttattc ttgctccagc tagctcaact gtggcccaat       180
agtttagttg acaatcatga gatcaggcgt gccatttgcc gggaaaagga aaggcggaga       240
gcattggaag gaaacattgg gaaggagatg gtatttgaga aattcttaac tttttttacgc      300 catagctgtt tgtttgcttc taacgtgcta acttttggat gtgataaata tccatttgtc       360
atcgaatatt atcatgaact cgcacatttc gctcatgttt atcattcctc aactttttatt      420 ttattttagg atcaaacgaa gataacaaag aagaaacaga cacaattggt ccctaaatct       480
gagggtatta cttatcccga caagacttca ggtgttgaag ttaaagcaag tgttgtccta       540
actgcaacca ccacgtcctt agtggactgt caacctgcag cagactcgtc ctttgaaagg       600
tcaaagcagc aacatgagaa attaaagcga acttcgagct taagcaatcc tgcagcagaa       660
ggaaagaaag tcagaagaaa gacagaacca gctctagaag aaactcacct gcccgcagag       720
aaacccctcg ttctggccct gaagcggcag acacatctaa aatccaagac acataaacag       780
gtacaggtac atccacagtc caaggcacat aaacaggcac aggtacatcc aaaggccaag       840
acacagactc ctccagacct gaacctgcca agttaggtac tacagcttag attttttttc       900
tcaaagtctg gctctagcct tgcctttgtt tttcgtagct atagtttcgc ttctaatttt       960
tgcgcctagt attgattttc tagtcgtttc ttacgtagaa gacgaagtcc ctctcctcgt      1020
```

-continued

```
tacaaattaa agatgttaag agaagctcca attctttcaa tctgtttttt ttgacggaat      1080
aaaccaacac atgtagccta tttctaaatg ggtctaaatt tgtcggcggc ccaataaggg      1140
gtcataataa aagaataaaa agccttaaaa aggaattagt atgtatctga aatcaagctc      1200
actggactgg acgaccaaaa aaaaagcgca ccgaaaattc ccgcgttctc ttcttaccag      1260
ttaccacgcc gaatcactga cctcaaatcc agagcttgac gaatctcgtg ctatgcgaat      1320
gctactaggt tctaatatcc atcttcttcc gacgattcta gggtttcaat tttctccgat      1380
aaccccgtga agctcttaca aagtcgagaa gtgcgtggtt aggttttccg gcgg           1434

<210> SEQ ID NO 8
<211> LENGTH: 667
<212> TYPE: DNA
<213> ORGANISM: Arabidopsis thaliana
<220> FEATURE:
<221> NAME/KEY: misc_feature
<222> LOCATION: (1)..(667)
<223> OTHER INFORMATION: DNA sequence of a 3' UTR, T-At.mei1-1:2:1.

<400> SEQUENCE: 8
gacagagtga ggtgctcgtt gagacagaaa catcaaccat gtgtgtcctg atgagaagtc       60
cgatgaaatg ttggaaaagc attcattaaa gaaacatcaa ggtcattgat catatttata      120
tgtagatcac agttttttttt cttttttataa agtaatttttg ttaagtttat gagaatgatg      180
cagacattcc tatacttccg gttaccgttt ttgctgctag gttacagatt tatatgatgt      240
tttttccctc taattttagt catccacaag agacaaaaga aaaaggcaca cacatttata      300
ttcaaaaact aagaacatag gtcacacaag aaagattcat acatcacatg gcaaaacaaa      360
aaaaaacaaa aaaatataaa gcctggagag cagatgccaa atttttaact atataaatttg      420 gcatttatag cttaagagaa aatacataat gggtgtagat aaaacagtga tagtactgta      480
aaaataaata aaatagtaca tttagagaga ctttacagct agaaaacgag gctctttagg      540
catgaacttc tggtttgcat aaacatccat gtaatctcca aacacaaact ttggatactt      600
cttctcactt ccttcctctt ccgccaccgc ggctggccct atcgccgcct tgtacgacgg      660
attgtag                                                                667

<210> SEQ ID NO 9
<211> LENGTH: 1030
<212> TYPE: DNA
<213> ORGANISM: Arabidopsis thaliana
<220> FEATURE:
<221> NAME/KEY: misc_feature
<222> LOCATION: (1)..(1030)
<223> OTHER INFORMATION: DNA sequence of an EXP, EXP-At.Cdc45:1:1
      comprising a promoter (P-At.Cdc45-1:1:1), operably linked 5' to a
      leader (L-At.Cdc45-1:1:1).

<400> SEQUENCE: 9
ctaatacaaa ggtgcatgag tagtagtaac tgaataaata ataagtgcaa atagttgact       60
taaaataaga agttgaaaga gttgaatgat ttcatctcac tttttaccat ttgagataaa      120
taagtttgaa aattgattca acttattcaa ccacaaaaat tagaaaacta aaccaattat      180
aaaaaacgaa ttgttcaacc ctttcatcta ctattttgga gaggaattga ttaaatgatg      240
ttcaactttt ttttcaaact caaaattttc ctatcattta tatatctagc aattcatttg      300
caactgaaat gttttttttcg tgtcaaactc taggtttgaa acccgtatac atcaccaaca      360
ataactagag tttgaaatca aataatattt tttcatatat aaaacaattt aaaatttctt      420
ttagataatt aataaaaaat gtatgacaca cagacacagc tggttgattt gtttatttga      480
```

-continued

```
atttttgact aggattaaga acattaatca tcaaccgttg attatataag caagttgaag       540
aaaaggcacg gttcagattc acctcttctc atatgatgcg ttacataaga tcctttccct       600
ctttccctca ttttcaggtt cagcgccatc gtcaaaaact tttggcggtc gatcaaaaaa       660
tttcgaaatt tgaagatttc gccggcaaat acacaaaccc gaaatgaat aacacttcaa        720 aattttcatt accagaagaa agaaatcaaa taccttcaga tctctatctt cctcattcac       780
acaccctctc tctcttctcc ttttctctct tctcctttc tctatctccc tctttgttcc        840
gttcgcatcc tctaatcatc gtcaacaagc cgacgaagag agaaacgaat ccaaagttcg       900
ttacttgaaa gctacccaga agaattcaaa tctcaggtac ttttcctgtg gatttgatct       960
gggcactgct tattagggat ttgattggat ctacaaaatt ctgccttctg ggtgattcaa      1020
tttcacggaa                                                             1030
```

```
<210> SEQ ID NO 10
<211> LENGTH: 737
<212> TYPE: DNA
<213> ORGANISM: Arabidopsis thaliana
<220> FEATURE:
<221> NAME/KEY: misc_feature
<222> LOCATION: (1)..(737)
<223> OTHER INFORMATION: DNA sequence of a promoter, P-At.Cdc45-1:1:1:1.

<400> SEQUENCE: 10
```

```
ctaatacaaa ggtgcatgag tagtagtaac tgaataaata ataagtgcaa atagttgact        60
taaaataaga agttgaaaga gttgaatgat ttcatctcac tttttaccat ttgagataaa       120
taagtttgaa aattgattca acttattcaa ccacaaaaat tagaaaacta aaccaattat       180
aaaaaacgaa ttgttcaacc ctttcatcta ctatttggga gaggaattga ttaaatgatg       240 ttcaacttt ttttcaaact caaaattttc ctatcattta tatatctagc aattcatttg        300
caactgaaat gttttttttcg tgtcaaactc taggtttgaa acccgtatac atcaccaaca      360
ataactagag tttgaaatca ataatatttt tttcatatat aaaacaattt aaaatttctt       420
ttagataatt aataaaaaat gtatgacaca cagacacagc tggttgattt gtttatttga       480
atttttgact aggattaaga acattaatca tcaaccgttg attatataag caagttgaag       540
aaaaggcacg gttcagattc acctcttctc atatgatgcg ttacataaga tcctttccct       600
ctttccctca ttttcaggtt cagcgccatc gtcaaaaact tttggcggtc gatcaaaaaa       660
tttcgaaatt tgaagatttc gccggcaaat acacaaaccc gaaatgaat aacacttcaa        720 aattttcatt accagaa                                                      737
```

```
<210> SEQ ID NO 11
<211> LENGTH: 293
<212> TYPE: DNA
<213> ORGANISM: Arabidopsis thaliana
<220> FEATURE:
<221> NAME/KEY: misc_feature
<222> LOCATION: (1)..(293)
<223> OTHER INFORMATION: DNA sequence of a leader, L-At.Cdc45-1:1:1.

<400> SEQUENCE: 11
```

```
gaaagaaatc aaataccttc agatctctat cttcctcatt cacacaccct ctctctcttc        60
tccttttctc tcttctcctt ttctctatct ccctctttgt tccgttcgca tcctctaatc       120
atcgtcaaca agccgacgaa gagagaaacg aatccaaagt tcgttacttg aaagctaccc       180
agaagaattc aaatctcagg tacttttcct gtggatttga tctgggcact gcttattagg       240
```

-continued

```
gatttgattg gatctacaaa attctgcctt ctgggtgatt caatttcacg gaa                   293
```

```
<210> SEQ ID NO 12
<211> LENGTH: 734
<212> TYPE: DNA
<213> ORGANISM: Arabidopsis thaliana
<220> FEATURE:
<221> NAME/KEY: misc_feature
<222> LOCATION: (1)..(734)
<223> OTHER INFORMATION: DNA sequence of a 3' UTR, T-At.Cdc45:1.

<400> SEQUENCE: 12
catagtctca ttgttcttcg attcagtgtg ttttctttta tagttttcag ttttatctca            60
ctgtttgcat tttttacgag cctgtgtaat aggcacaatc tgttatcaat catgtaactt           120
gtttaatcaa ataaccatag agttttatgt gaaaaggtcc tttactcatt tggtgttaac           180
tctttacctc ttcaggtctt taactctgtt tatataaaac atctaatgaa caatctgtgt           240
tttgaacgga tagattaaaa atacacgcag gcacaagaca agaccaaaga cgatatgggt           300
ttggctaaat ccccaaaatt tgtacaaaaa catgaacaaa cataatgaaa ttcaacaaag           360
attaatactc caacaatcca gttccctcta gtctaaccca aacttgaaag agaaaaaaat           420
ggagacctgc tcagactcgt gaagcgaaat cttcattgag atgatggaaa cttgagaaca           480
aaatggctaa agacattgtc tatttcttaa cttgaaggct tctttctcca cagagttgtc           540
ccgcggttga tctcctgacc atctccagac aacctcagga ggtgcaagaa ctggctatcg           600
ttgtggccct gtgtgccaga cgtggcagag ccattggttc caccaatttc agaggtggtg           660
gtggtgagtg aatccaccac atcgtcttgt tgacattctc ttctataatc cagagttatg           720
acctgaagct cgtg                                                             734
```

```
<210> SEQ ID NO 13
<211> LENGTH: 1346
<212> TYPE: DNA
<213> ORGANISM: Arabidopsis thaliana
<220> FEATURE:
<221> NAME/KEY: misc_feature
<222> LOCATION: (1)..(1346)
<223> OTHER INFORMATION: DNA sequence of an EXP, EXP-At.Swi1 comprised
      of a promoter and leader.

<400> SEQUENCE: 13
ttaaatgtat tgttgactgt ttttgataat taagaaaaaa atatttttaa attattaaaa            60
atattgttga ctcaacaaaa aaatataact taaatgtatt gggcaaataa tcatggtcat           120
aagtcctcaa gcttattatt tgttttgatt ggtttaaata ctttataaaa aaaatatcaa           180
ttatatcatg ttattacgta aattaagctt tttgatttta aaaagcttc agctcaataa            240 agaaaaacag attcagttat cattggagta taaaattggt cgatacatta gagacattaa           300
tccttacatc ataaacaatt taatgtgaat aaaacatcat aaatcacata tcattatccg           360
aaaataatca tatgtaagaa taatcactgt gacaaaaaaa aaaaacaatt cctcacgtgt           420
gtagtcggtc cccactctag tagcagtagc ttaatgatgc cttctccgca cgtgtaacac           480
gaaatttatt cgctacggcc aattacatta accttcaggt cttatcaccg ttaaattttc           540
aaaatgacac acgtggcatc aatccgtaat atcactacgt ctgctttcaa tctttcattg           600
tagatgattt cgtacaccaa tttccgcgaa cgtttacagt ttagatacag tttgagggca           660
aatctgtcaa tatacgccaa cttgctgcga aagcaatata gtcacgtgcc gtgcacacgc           720
atataagact cacacactca caccactctc tctctctctc taacctcata tataaagcca           780
```

```
cctcccagat tcattaaatg cgacatttca aaactttct ttttgctgtc ttccccataa     840
gctctctgct gattaaaaag attttctggt ataaaacaaa attcttcaaa tatttctggg     900
tttatgtttt ctctctattt ctcagaaatg ctttaatttc tccatccgcg tccatgtttt     960
tttttctccg ttgctgattt tgattttttt aatccagtga aaaggaggaa cgaagattat    1020
cgagagcaaa aatcatgagt gtaagatctc tctcgctctc agattttatt tttttttcgct   1080 gtgatataaa tggctcagtc actatcagtc tcatgatgag aaaaataaaa ctcatcaccg    1140
cttgattctg tttccttagt gtctcccacg cgcgtaccag aaagcgcgtg tgtgtttctt    1200
gttatactcg cagagtcagg tttttttcaaa tatattctct ccaggcagca gcaacaacaa   1260
caaaccgatt ttttcattat tccttataac aatttttgat tctccagaaa aaaaatatct    1320
ctcttagttt ttctcttgtt ctacag                                        1346
```

<210> SEQ ID NO 14
<211> LENGTH: 1721
<212> TYPE: DNA
<213> ORGANISM: Arabidopsis thaliana
<220> FEATURE:
<221> NAME/KEY: misc_feature
<222> LOCATION: (1)..(1721)
<223> OTHER INFORMATION: DNA sequence of an EXP, EXP-At.Swi1a comprised
      of a promoter and leader.

<400> SEQUENCE: 14

```
ttaaatgtat tgttgactgt ttttgataat taagaaaaaa atatttttaa attattaaaa      60
atattgttga ctcaacaaaa aaatataact taaatgtatt gggcaaataa tcatggtcat     120
aagtcctcaa gcttattatt tgttttgatt ggtttaaata ctttataaaa aaaatatcaa     180
ttatatcatg ttattacgta aattaagctt tttgattttta aaaaagcttc agctcaataa    240
agaaaaacag attcagttat cattggagta taaaattggt cgatacatta gagacattaa     300
tccttacatc ataaacaatt taatgtgaat aaaacatcat aaatcacata tcattatccg     360
aaaataatca tatgtaagaa taatcactgt gacaaaaaaa aaaacaatt cctcacgtgt      420 gtagtcggtc cccactctag tagcagtagc ttaatgatgc cttctccgca cgtgtaacac     480
gaaatttatt cgctacggcc aattacatta accttcaggt cttatcaccg ttaaattttc     540
aaaatgacac acgtggcatc aatccgtaat atcactacgt ctgctttcaa tctttcattg     600
tagatgattt cgtacaccaa tttccgcgaa cgtttacagt ttagatacag tttgagggca     660
aatctgtcaa tatacgccaa cttgctgcga aagcaatata gtcacgtgcc gtgcacacgc     720
atataagact cacacactca caccactctc tctctctctc taacctcata tataaagcca     780
cctcccagat tcattaaatg cgacatttca aaactttct ttttgctgtc ttccccataa     840
gctctctgct gattaaaaag attttctggt ataaaacaaa attcttcaaa tatttctggg     900
tttatgtttt ctctctattt ctcagaaatg ctttaatttc tccatccgcg tccatgtttt     960
tttttctccg ttgctgattt tgattttttt aatccagtga aaaggaggaa cgaagattat    1020
cgagagcaaa aatcatgagt gtaagatctc tctcgctctc agattttatt tttttttcgct   1080 gtgatataaa tggctcagtc actatcagtc tcatgatgag aaaaataaaa ctcatcaccg    1140
cttgattctg tttccttagt gtctcccacg cgcgtaccag aaagcgcgtg tgtgtttctt    1200
gttatactcg cagagtcagg tttttttcaaa tatattctct ccaggcagca gcaacaacaa   1260
caaaccgatt ttttcattat tccttataac aatttttgat tctccagaaa aaaaatatct    1320
ctcttagttt ttctcttgtt ctacagagta cgatgttcgt gaaacggaat ccgattagag    1380
```

-continued

```
aaaccaccgc cgggaaaatc tcttcgccgt cgtcaccgac tttgaatggt aaactactga     1440
agctatagtt tcttcgtttt tgttgatttt ctcgcttctc ttctaatttc tgaatttttg     1500
gtttgggttt gttcttacag ttgcagtcgc gcatataaga gctggatctt attacgaaat     1560
cgatgcttcg attcttcctc agagatcgcc ggaaaatctt aaatcgatta gagtcgtcat     1620
ggtattcact cgattctctg cttttttcac cttttattat agacagatct cgttttttgt     1680
tgttcgtctg ggttttcgag tgattttttta aggtttattg g                       1721
```

```
<210> SEQ ID NO 15
<211> LENGTH: 709
<212> TYPE: DNA
<213> ORGANISM: Arabidopsis thaliana
<220> FEATURE:
<221> NAME/KEY: misc_feature
<222> LOCATION: (1)..(709)
<223> OTHER INFORMATION: DNA sequence of a 3' UTR, T-At.Swi1-1:2:1.

<400> SEQUENCE: 15
```

```
agttgtcact ggaaactgat gcatcagatc ttactttccc tacaagtaag ctgatgtgaa       60
ctggtaaggt ctcttccatg aaatatataa taacttacaa gcgagcaggt atttaaaagt      120
accacttata tttatataag gaactatatt tatgggaata atttggcaac ttttttgaaat      180 tattcctctt taatttaggg attttacgtc tctggttatt aattatatat agagagagat      240
gatttgaaat agagaggctt atcataggaa tatattcttt tgaaagacag ggatcatcat      300
attctgtatt actgaacaat ttctataatg atacagttat atatatatat atatacttat      360
tattcaattc ctagcgcttt tgattttaaa tatattattt tcgtgtagtt gattaatttt      420
gaaaaacttg tattacgcat atgaattatg tcccgttgat ctataaaaat catattttgc      480
gattaagcac aaactataaa agtatgttta agttcctgcg ggttgaccag tttcacttta      540
aaatcttggt ctttgggatg agtttgccga taaattttgt gacttatggt tatctaataa      600
tacgaatgtt atactttcca aaatttgaaa aaaacaatat gaatacttta ttattatctt      660
tttccttcca tttctcttcc cgcgtttttgt tgttcgaccg atcttgtag              709
```

```
<210> SEQ ID NO 16
<211> LENGTH: 1361
<212> TYPE: DNA
<213> ORGANISM: Arabidopsis thaliana
<220> FEATURE:
<221> NAME/KEY: misc_feature
<222> LOCATION: (1)..(1361)
<223> OTHER INFORMATION: DNA sequence of an EXP, EXP-At.Asy1-1:1
      comprising a promoter (P-At.Asy1-1:1:1), operably linked 5' to a
      leader (L-At.Asy1-1:1:1).

<400> SEQUENCE: 16
```

```
caaaacattt gactggaaac tcataagagc agaataagga aaaatggaga gaaacctggg       60
ttatcgattc cgcaacacta ttggaaagag cagcgataag tccactctcg tatgtagcac      120
ttagcaaatc gaagtggagg taaggcactt gtttccatac attcttccat cgtgtagaca      180
acacacttgt cttcaaagca tcttcagtgg acaaacttgc taggatcatg accaacacat      240
cgtcggggag tttactgatc cggtcgtcga ttggatcgat gaggatacgt ttgcctcttg      300
catccgatga tcgtggtgcg ttcatggatt tgggctgatg gtgaggttga gaggttttga      360
gaattgagag agggaattga ctcatttcga cttgtagact agagagatta gaataggatt      420
atagatgaag agaagagaga cgaagaggtt acatatatat acatgatata cgaagagata      480
agagtgatta tagtcagaca acgaaaatat ctggtaataa ttgtaatgaa accctaatca      540
```

```
aagtttattt ttattcttca tttttaattt tcattacaat ttataacagt tagttatttt          600
tgttgactat gacatttaat aaaatggaaa gaatttaaca attaatgcat tccgtataaa          660
tggcacagga taaaatatgc attcagattt ctttccatga caccagaaat cataacatat          720
ataaccatca ccaagttggt tatttcaagt ctttaacgac ttttgaaaga aaaagaaaaa          780
tacaaaacga agaaacaaaa caaaattttc aaaagaacag aaatgtaatt ggggctaaac          840
ccaaaaacaa tatatgagcc tgggttgggc tgtaacatta aataatcaaa aaacaaaatt          900
atactagaaa aattaaaatc agggtggggt ccagttaaga agagcaacga acttttggat          960
tttggcagcg cttgtacgtg attatagtaa ttagactata ttgcccctac taccatctca         1020
aataccaacg ttacccctaa atatcttctg gacgttgaaa cgaatagacg atattgaccc         1080
tgcttttgtc actaaatacc aacgttacca ctaaatatct ttcgcgtcgt tacacaatta         1140
gtcgatttta cccatgctat caccactaaa tatcagcttt gccactaaat attcttctcc         1200
atttctataa acttcaaacg atctcccaga ctccctcact agtcataaac tgataaacat         1260
tctctccatt ttcaattttt tttgaaattt tctcttccct ccttctctct gagaattcct         1320
ccgacgacga atctcgttat tcgtttcaca cttctgcaaa a                            1361
```

<210> SEQ ID NO 17
<211> LENGTH: 1237
<212> TYPE: DNA
<213> ORGANISM: Arabidopsis thaliana
<220> FEATURE:
<221> NAME/KEY: misc_feature
<222> LOCATION: (1)..(1237)
<223> OTHER INFORMATION: DNA sequence of a promoter, P-At.Asy1-1:1:1.

<400> SEQUENCE: 17

```
caaaacattt gactggaaac tcataagagc agaataagga aaaatggaga gaaacctggg           60
ttatcgattc cgcaacacta ttggaaagag cagcgataag tccactctcg tatgtagcac          120
ttagcaaatc gaagtggagg taaggcactt gtttccatac attcttccat cgtgtagaca          180
acacacttgt cttcaaagca tcttcagtgg acaaacttgc taggatcatg accaacacat          240
cgtcggggag tttactgatc cggtcgtcga ttggatcgat gaggatacgt ttgcctcttg          300
catccgatga tcgtggtgcg ttcatggatt tgggctgatg gtgaggttga gaggttttga          360
gaattgagag agggaattga ctcatttcga cttgtagact agagagatta gaataggatt          420
atagatgaag agaagagaga cgaagaggtt acatatatat acatgatata cgaagagata          480
agagtgatta tagtcagaca acgaaaatat ctggtaataa ttgtaatgaa accctaatca          540
aagtttattt ttattcttca tttttaattt tcattacaat ttataacagt tagttatttt          600
tgttgactat gacatttaat aaaatggaaa gaatttaaca attaatgcat tccgtataaa          660
tggcacagga taaaatatgc attcagattt ctttccatga caccagaaat cataacatat          720
ataaccatca ccaagttggt tatttcaagt ctttaacgac ttttgaaaga aaaagaaaaa          780
tacaaaacga agaaacaaaa caaaattttc aaaagaacag aaatgtaatt ggggctaaac          840
ccaaaaacaa tatatgagcc tgggttgggc tgtaacatta aataatcaaa aaacaaaatt          900
atactagaaa aattaaaatc agggtggggt ccagttaaga agagcaacga acttttggat          960
tttggcagcg cttgtacgtg attatagtaa ttagactata ttgcccctac taccatctca         1020
aataccaacg ttacccctaa atatcttctg gacgttgaaa cgaatagacg atattgaccc         1080
tgcttttgtc actaaatacc aacgttacca ctaaatatct ttcgcgtcgt tacacaatta         1140
```

-continued

```
gtcgatttta cccatgctat caccactaaa tatcagcttt gccactaaat attcttctcc      1200
atttctataa acttcaaacg atctcccaga ctccctc                              1237

<210> SEQ ID NO 18
<211> LENGTH: 124
<212> TYPE: DNA
<213> ORGANISM: Arabidopsis thaliana
<220> FEATURE:
<221> NAME/KEY: misc_feature
<222> LOCATION: (1)..(124)
<223> OTHER INFORMATION: DNA sequence of a leader, L-At.Asy1-1:1:1.

<400> SEQUENCE: 18
actagtcata aactgataaa cattctctcc attttcaatt ttttttgaaa ttttctcttc       60
cctccttctc tctgagaatt cctccgacga cgaatctcgt tattcgtttc acacttctgc      120
aaaa                                                                   124

<210> SEQ ID NO 19
<211> LENGTH: 505
<212> TYPE: DNA
<213> ORGANISM: Arabidopsis thaliana
<220> FEATURE:
<221> NAME/KEY: misc_feature
<222> LOCATION: (1)..(505)
<223> OTHER INFORMATION: DNA sequence of a 3' UTR, T-At.Asy1-1:1:1.

<400> SEQUENCE: 19
agacaccacc tctatcagac accataacca ccttcttcag tggtgatgat attaacctga       60
aacactcgct ttttattgct ttatttctcc tctgcattca gactattttc atactccatg      120
cttgttatta tctctcttaa agtatcatat cttatcgcac ttttgggaag ataatttatt      180
gcatatcaaa ctttaacact tattagttat tactgtgagt attattcact aatgctctac      240
atgcttttat ggaacaagta tgaagtatag gactatcttc gttttaaatt ccctgtcga       300 tcactttaat ccaaaaactt taactttaga tactaacacg tgttgaaacg tgtactacgc      360
cattccacgc gtcaggaaat cgagcaccgc cgaattcatc tcgccggagc atcaccgcct      420
tcgatcagtc accgccgatc cgtctagtag tgatggatag ccttctcctt gttgtcgatc      480
tcgaatccaa atccaataaa cgtcg                                            505

<210> SEQ ID NO 20
<211> LENGTH: 720
<212> TYPE: DNA
<213> ORGANISM: Glycine max
<220> FEATURE:
<221> NAME/KEY: misc_feature
<222> LOCATION: (1)..(720)
<223> OTHER INFORMATION: DNA sequence of an EXP, EXP-Gm.Rsp-1:1
      comprising a promoter (P-Gm.Rsp-1-1:1:1), operably linked 5' to a
      leader (L-Gm.Rsp-1-1:1:1).

<400> SEQUENCE: 20
aaataatata taaaaatatt acaaaaatct tatttattag tgatctcttt ttatatataa       60
ataagaaaaa tttaggggggg catgactccc cccaagatta actaagcttc accactaatc      120
acagagtata tactacattc aactcaagta tttatctatc agaaataaaa taaaataaca      180
atggtatcgg ttgttctgtt ggcacaattt tttagagagg ctaatcaagt taaaaataca      240
ttagatatta gtttggaatt ttcaaactat tctttttcta cttttttttta tcagaaaaaa      300 taaatagttt gaaaactcca aactatttta tttatgtatt ctgtttttta tttctcatgc      360
tttatgagca catcttgctt ccatgtatta gttttttcttg aggtttctca gctttaaata      420
```

-continued

```
aattttattt ctaagcttta ataatatttg aattaacgaa taaaaattat tatttgaata      480
aaaattatta tacctaataa tatataaagt caaattgtta taaattgata cgtctaaata      540
ataaatgtat agtttcttac aaaattcgtg tttcatatcc acctaaacca taagtcctat      600
tggctcaaat gcaacatatg cctcataatg ccatctcacc cttcctccaa aaggtctata      660
tatatctttg gtttctctgt gtctcaatat cacattctca tctctaacca ctttgcttca      720
```

```
<210> SEQ ID NO 21
<211> LENGTH: 558
<212> TYPE: DNA
<213> ORGANISM: Glycine max
<220> FEATURE:
<221> NAME/KEY: misc_feature
<222> LOCATION: (1)..(558)
<223> OTHER INFORMATION: DNA sequence of a promoter, P-Gm.Rsp-1-1:1:1.

<400> SEQUENCE: 21
aaataatata taaaaatatt acaaaaatct tatttattag tgatctcttt ttatatataa       60
ataagaaaaa tttagggggg catgactccc cccaagatta actaagcttc accactaatc      120
acagagtata tactacattc aactcaagta tttatctatc agaaataaaa taaaataaca      180
atggtatcgg ttgttctgtt ggcacaattt tttagagagg ctaatcaagt taaaaataca      240
ttagatatta gtttggaatt ttcaaactat tcttttttcta cttttttttta tcagaaaaaa      300 taaatagttt gaaaactcca aactatttta tttatgtatt ctgttttttta tttctcatgc      360 tttatgagca catcttgctt ccatgtatta gtttttcttg aggtttctca gctttaaata      420
aattttattt ctaagcttta ataatatttg aattaacgaa taaaaattat tatttgaata      480
aaaattatta tacctaataa tatataaagt caaattgtta taaattgata cgtctaaata      540
ataaatgtat agtttctt                                                     558
```

```
<210> SEQ ID NO 22
<211> LENGTH: 162
<212> TYPE: DNA
<213> ORGANISM: Glycine max
<220> FEATURE:
<221> NAME/KEY: misc_feature
<222> LOCATION: (1)..(162)
<223> OTHER INFORMATION: DNA sequence of a leader, L-Gm.Rsp-1-1:1:1.

<400> SEQUENCE: 22
acaaaattcg tgtttcatat ccacctaaac cataagtcct attggctcaa atgcaacata       60
tgcctcataa tgccatctca cccttcctcc aaaaggtcta tatatatctt tggtttctct      120
gtgtctcaat atcacattct catctctaac cactttgctt ca                         162
```

```
<210> SEQ ID NO 23
<211> LENGTH: 188
<212> TYPE: DNA
<213> ORGANISM: Arabidopsis thaliana
<220> FEATURE:
<221> NAME/KEY: misc_feature
<222> LOCATION: (1)..(188)
<223> OTHER INFORMATION: DNA sequence of a 3' UTR, T-At.Cdc45:3.

<400> SEQUENCE: 23
catagtctca ttgttcttcg attcagtgtg ttttcttttta tagttttcag ttttatctca       60
ctgtttgcat ttttttacgag cctgtgtaat aggcacaatc tgttatcaat catgtaactt      120
gtttaatcaa ataaccatag agtttttatgt gaaaaggtcc tttactcatt tggtgttaac      180
```

-continued

```
tctttacc                                                          188
```

```
<210> SEQ ID NO 24
<211> LENGTH: 509
<212> TYPE: DNA
<213> ORGANISM: Arabidopsis thaliana
<220> FEATURE:
<221> NAME/KEY: misc_feature
<222> LOCATION: (1)..(509)
<223> OTHER INFORMATION: DNA sequence of a 3' UTR, T-At.Cdc45:4.

<400> SEQUENCE: 24
catagtctca ttgttcttcg attcagtgtg ttttctttta tagttttcag ttttatctca    60
ctgtttgcat tttttacgag cctgtgtaat aggcacaatc tgttatcaat catgtaactt   120
gtttaatcaa ataaccatag agtttttatgt gaaaaggtcc tttactcatt tggtgttaac   180
tctttacctc ttcaggtctt taactctgtt tatataaaac atctaatgaa caatctgtgt   240
tttgaacgga tagattaaaa atacacgcag gcacaagaca agaccaaaga cgatatgggt   300
ttggctaaat ccccaaaatt tgtacaaaaa catgaacaaa cataatgaaa ttcaacaaag   360
attaatactc caacaatcca gttccctcta gtctaaccca aacttgaaag agaaaaaaat   420
ggagacctgc tcagactcgt gaagcgaaat cttcattgag atgatggaaa cttgagaaca   480
aaatggctaa agacattgtc tatttctta                                     509
```

```
<210> SEQ ID NO 25
<211> LENGTH: 1474
<212> TYPE: DNA
<213> ORGANISM: Artificial
<220> FEATURE:
<223> OTHER INFORMATION: DNA sequence of an EXP,
      EXP-Gm.Rsp-1+Gm.Rsp-1+At.AtpE:1 comprising a promoter
      (P-Gm.Rsp-1-1:1:1), operably linked 5' to a leader
      (L-Gm.Rsp-1-1:1:1), operably linked 5' to an intron (I-At.AtpE:1).

<400> SEQUENCE: 25
aaataatata taaaaatatt acaaaaatct tatttattag tgatctcttt ttatatataa     60
ataagaaaaa tttaggggggg catgactccc cccaagatta actaagcttc accactaatc   120
acagagtata tactacattc aactcaagta tttatctatc agaaataaaa taaaataaca   180
atggtatcgg ttgttctgtt ggcacaattt tttagagagg ctaatcaagt taaaaataca   240
ttagatatta gtttggaatt ttcaaactat tcttttttcta cttttttttta tcagaaaaaa   300 taaatagttt gaaaactcca aactatttta tttatgtatt ctgtttttta tttctcatgc   360
tttatgagca catcttgctt ccatgtatta gttttttcttg aggtttctca gctttaaata   420 aattttatttt ctaagcttta ataatatttg aattaacgaa taaaaattat tatttgaata   480
aaaattatta tacctaataa tatataaagt caaattgtta taaattgata cgtctaaata   540
ataaatgtat agtttcttac aaaattcgtg tttcatatcc acctaaacca taagtcctat   600
tggctcaaat gcaacatatg cctcataatg ccatctcacc cttcctccaa aaggtctata   660
tatatctttg gtttctctgt gtctcaatat cacattctca tctctaacca ctttgcttca   720
caggtaagcc ttttcgatcc tttaatcgtc gatgttggat cttagatctg gattcttcac   780
gttcttgtgt tctcgattcc tgatttgttt ttgagtaatt tgttggaata atctgatttc   840
ctaaaagtta tcggaattaa gtggaaagtg aatcatctgc ttctggattt gatcttcgat   900
tttgcattta accttttcctc tgcttctgga tttgatcagt tcaatactat cttcatacaa   960
tgttgttatg tccaaattgt tgaattttttc atttagagtt agcttcagag aaaacaacaa  1020
```

```
aactagtagt atgtgtgaaa caagaacatg aagaagatgg aaagctgatt gggaacattg        1080
catttagatg tctttttctcg tttatgtttg gatctcaatt cttcatgttc ttgttgtgtg       1140
tcattgaaat tgttggaata cgtagatatc agagtaggtc attttgggaa agctattgaa        1200
tttaagagga agatgaatca ttttaacaag ctccatcgat tttgcgctta atctgtctct        1260
cttctgcttc tggatttgat taatttcatt ctattttgtt ttctcataag ttgttgttat        1320
gttcaaattg ttgaatttgg aatgatttca tttctcaaat agggtttact gagacaatga        1380
ttccagattt agtctatctg aaaatggttc agctttcttc ttgttgatcc atttgtctaa        1440
cattctctca tgttttttgtt tttccttgac aggt                                   1474

<210> SEQ ID NO 26
<211> LENGTH: 754
<212> TYPE: DNA
<213> ORGANISM: Arabidopsis thaliana
<220> FEATURE:
<221> NAME/KEY: misc_feature
<222> LOCATION: (1)..(754)
<223> OTHER INFORMATION: DNA sequence of an intron, I-At.AtpE:1.

<400> SEQUENCE: 26
caggtaagcc ttttcgatcc tttaatcgtc gatgttggat cttagatctg gattcttcac          60
gttcttgtgt tctcgattcc tgatttgttt ttgagtaatt tgttggaata atctgatttc         120
ctaaaagtta tcggaattaa gtggaaagtg aatcatctgc ttctggattt gatcttcgat         180
tttgcattta accttttcctc tgcttctgga tttgatcagt tcaatactat cttcatacaa        240
tgttgttatg tccaaattgt tgaattttttc atttagagtt agcttcagag aaaacaacaa        300
aactagtagt atgtgtgaaa caagaacatg aagaagatgg aaagctgatt gggaacattg         360
catttagatg tctttttctcg tttatgtttg gatctcaatt cttcatgttc ttgttgtgtg        420
tcattgaaat tgttggaata cgtagatatc agagtaggtc attttgggaa agctattgaa         480
tttaagagga agatgaatca ttttaacaag ctccatcgat tttgcgctta atctgtctct         540
cttctgcttc tggatttgat taatttcatt ctattttgtt ttctcataag ttgttgttat         600
gttcaaattg ttgaatttgg aatgatttca tttctcaaat agggtttact gagacaatga         660
ttccagattt agtctatctg aaaatggttc agctttcttc ttgttgatcc atttgtctaa         720
cattctctca tgttttttgtt tttccttgac aggt                                    754

<210> SEQ ID NO 27
<211> LENGTH: 2831
<212> TYPE: DNA
<213> ORGANISM: Artificial
<220> FEATURE:
<223> OTHER INFORMATION: DNA sequence of an EXP,
     EXP-Zm.Cdc45-2+Zm.DnaK:1:2 comprising a promoter
     (P-Zm.Cdc45-2-1:1:3), operably linked 5' to a leader
     (L-Zm.Cdc45-2-1:1:1), operably linked 5' to an intron
     (I-Zm.DnaK:1).

<400> SEQUENCE: 27
tattgttatc tctgttttga attagtttgt gtcataacaa catgatgcga aacattgtca          60
aacgtttgcc tttgtggttg aaccaatggt gtacataatt aaaatgatat aacatgcaat         120
attcttaatg tatgtaatac aataacttta ccgtctacca ttttaacaaa tttgctagat        180
ctttatttgt tattcgataa tctaaaaccc ataaaaggga tagagatgta cctacactgc        240
ccctagaggc ggctcacccg ctcctgtttt ggaacgtaaa aaatttaccc tagttgcaca        300
aaaattaata gaaatcagca catgaacatt gagctgtttg gttcaccgtc ttgctttaca        360
```

-continued

```
tggtttgcca cttctaaggt taaacatatt tgaccaattc agtcgtgtat ttgatttgta    420
gtcatagttg tggtaaaaaa atttctcctt gtgcgtagat cttatctatc aattactttt    480
aaaaatgtgt caaaattatc ttcgccatga taaaatatgg tgaagaattt agttcttaat    540
tttaggcgag tagtataata ataaatttaa gttcttaata ataagttctt aaatttaggg    600
agtccaaaca aggttgtaaa tgtagagatg aatttgagtt ttgtagagag tttgttaatt    660
tgaggacctg ttttatataa ctgtcggaga agagttttct ccgaaaactt attatattca    720
tatttagaga gttgtttata taaatattag agatgttttt agtgcgctaa taatttgttt    780
acccgcgcct ccctcctccg tgtatcctgc gggcctcttc ctacaagacc tccacctata    840
gatgtccaat aagcacgagg tccgcgagcc cggcacgaag cccgctgttt gggcccggtc    900
cgagcccggc acggcccggt tatatgcggg cctggatcgg cccggcacga ataagcgggc    960
caggctcgga caggaaatta ggcacggtgg gctagcccgg cacgacccgt ttagctctaa   1020
gcctgttaag cccgcttttt tacactaaaa cgtgcttttc ggcccgcata gcccgctttt   1080
ttcgtgctaa acgccccggc ccggtccgtt taggcccgtt gcgggccgaa cttggacaag   1140
aaattgagcc cgcgtgctta gccgacccgg ttttctaatc gtacctggcg ggccgggcct   1200
aaaacgggcc gggcttcacc ggaccaggcc ggaccgggcc gggcggcccg tttggacatc   1260
tctacctcca cccctccagt ttgtacagca ttaggctgtc cgcagtcgca tgctcgaaag   1320
ggtactctaa aggatagagt agcggataga gttgaatcag cctgcagccg ctcactcgtt   1380
cggccactgg gaatttaggg agggatagaa aaacgctaac tgcagagtcg ctctctctcg   1440
tactcgaaag ctgtctgtgt gtgtcttggg aggtgtgagg agagaataaa acaacagtga   1500
tggaaggaga gaatggaaaa aaataataaa aaaatgattg ttggtataga gttgagatat   1560
agagtaaaca cgaccgcaga gaattgtggt atagagtaga taatcttgct gacggggata   1620
gaatattcct tttagagtag aaatttagag tagtatgagt gctgatagcc ttactggtat   1680
gtgaaaacag ccactgtaga gcattaatag cggaggtcca gcccacaagg cgaaggaccc   1740
atcaaaggtg gaaatccagc ccagaagcgg gagacggaga actctcgtgt ctgtttcctt   1800
ccgtccccaa atccaaattt ttgcctggcg gtcttcggct tccctcccaa acccaaaccc   1860
aaattccaaa tccgccgatc cccgcgcgcc ctcacaaaaa gctcccgccg ctccatcact   1920
cctcagatcc ctccaactcc aattttcccc caatctctcc gagctccgac aatccccgga   1980
cccggccgat tgatgcggcg ggcgcgccaa gacgcaaact cggaccgacc gtcttcggta   2040
cgcgctcact ccgccctctg cctttgttac tgccacgttt ctctgaatgc tctcttgtgt   2100
ggtgattgct gagagtggtt tagctggatc tagaattaca ctctgaaatc gtgttctgcc   2160
tgtgctgatt acttgccgtc ctttgtagca gcaaaatata gggacatggt agtacgaaac   2220
gaagatagaa cctacacagc aatacgagaa atgtgtaatt tggtgcttag cggtatttat   2280
ttaagcacat gttggtgtta tagggcactt ggattcagaa gtttgctgtt aatttaggca   2340
caggcttcat actacatggg tcaatagtat agggattcat attataggcg atactataat   2400
aatttgttcg tctgcagagc ttattatttg ccaaaattag atattcctat tctgtttttg   2460
tttgtgtgct gttaaattgt taacgcctga aggaataaat ataaatgacg aaattttgat   2520
gtttatctct gctcctttat tgtgaccata agtcaagatc agatgcactt gttttaaata   2580
ttgttgtctg aagaaataag tactgacagt attttgatgc attgatctgc ttgtttgttg   2640
taacaaaatt taaaaataaa gagtttcctt tttgttgctc tccttacctc ctgatggtat   2700
```

-continued

```
ctagtatcta ccaactgaca ctatattgct tctctttaca tacgtatctt gctcgatgcc   2760
ttctccctag tgttgaccag tgttactcac atagtctttg ctcatttcat tgtaatgcag   2820
ataccaagcg g                                                        2831

<210> SEQ ID NO 28
<211> LENGTH: 1924
<212> TYPE: DNA
<213> ORGANISM: Zea mays
<220> FEATURE:
<221> NAME/KEY: misc_feature
<222> LOCATION: (1)..(1924)
<223> OTHER INFORMATION: DNA sequence of a promoter, P-Zm.Cdc45-2-1:1:3.

<400> SEQUENCE: 28
tattgttatc tctgttttga attagtttgt gtcataacaa catgatgcga aacattgtca     60
aacgtttgcc tttgtggttg aaccaatggt gtacataatt aaaatgatat aacatgcaat    120
attcttaatg tatgtaatac aataacttta ccgtctacca tttaacaaa tttgctagat    180 ctttatttgt tattcgataa tctaaaaccc ataaaaggga tagagatgta cctacactgc    240
ccctagaggc ggctcacccg ctcctgtttt ggaacgtaaa aaatttaccc tagttgcaca    300
aaaattaata gaaatcagca catgaacatt gagctgtttg gttcaccgtc ttgctttaca    360
tggtttgcca cttctaaggt taaacatatt tgaccaattc agtcgtgtat ttgatttgta    420
gtcatagttg tggtaaaaaa atttctcctt gtgcgtagat cttatctatc aattactttt    480
aaaaatgtgt caaaattatc ttcgccatga taaaatatgg tgaagaattt agttcttaat    540
tttaggcgag tagtataata ataaatttaa gttcttaata ataagttctt aaatttaggg    600
agtccaaaca aggttgtaaa tgtagagatg aatttgagtt ttgtagagag tttgttaatt    660
tgaggacctg ttttatataa ctgtcggaga agagttttct ccgaaaactt attatattca    720
tatttagaga gttgtttata taaatattag agatgttttt agtgcgctaa taatttgttt    780
acccgcgcct ccctcctccg tgtatcctgc gggcctcttc ctacaagacc tccacctata    840
gatgtccaat aagcacgagg tccgcgagcc cggcacgaag cccgctgttt gggcccggtc    900
cgagcccggc acggcccggt tatatgcggg cctggatcgg cccggcacga ataagcgggc    960
caggctcgga caggaaatta ggcacggtgg gctagcccgg cacgacccgt ttagctctaa   1020
gcctgttaag cccgcttttt tacactaaaa cgtgcttttc ggcccgcata gcccgctttt   1080
ttcgtgctaa acgccccggc ccggtccgtt taggcccgtt gcgggccgaa cttggacaag   1140
aaattgagcc cgcgtgctta gccgacccgg ttttctaatc gtacctggcg ggccgggcct   1200
aaaacgggcc gggcttcacc ggaccaggcc ggaccgggcc gggcggcccg tttggacatc   1260
tctacctcca cccctccagt ttgtacagca ttaggctgtc cgcagtcgca tgctcgaaag   1320
ggtactctaa aggatagagt agcggataga gttgaatcag cctgcagccg ctcactcgtt   1380
cggccactgg gaatttaggg agggatagaa aaacgctaac tgcagagtcg ctctctctcg   1440
tactcgaaag ctgtctgtgt gtgtcttggg aggtgtgagg agagaataaa acaacagtga   1500
tggaaggaga gaatggaaaa aaataataaa aaaatgattg ttggtataga gttgagatat   1560
agagtaaaca cgaccgcaga gaattgtggt atagagtaga taatcttgct gacggggata   1620
gaatattcct tttagagtag aaatttagag tagtatgagt gctgatagcc ttactggtat   1680
gtgaaaacag ccactgtaga gcattaatag cggaggtcca gcccacaagg cgaaggaccc   1740
atcaaaggtg gaaatccagc ccagaagcgg gagacggaga actctcgtgt ctgtttcctt   1800
ccgtccccaa atccaaattt ttgcctggcg gtcttcggct tccctcccaa acccaaaccc   1860
```

```
aaattccaaa tccgccgatc cccgcgcgcc ctcacaaaaa gctcccgccg ctccatcact     1920
cctc                                                                  1924

<210> SEQ ID NO 29
<211> LENGTH: 76
<212> TYPE: DNA
<213> ORGANISM: Zea mays
<220> FEATURE:
<221> NAME/KEY: misc_feature
<222> LOCATION: (1)..(76)
<223> OTHER INFORMATION: DNA sequence of a leader, L-Zm.Cdc45-2-1:1:1.

<400> SEQUENCE: 29
agatccctcc aactccaatt ttcccccaat ctctccgagc tccgacaatc cccggacccg       60
gccgattgat gcggcg                                                       76

<210> SEQ ID NO 30
<211> LENGTH: 439
<212> TYPE: DNA
<213> ORGANISM: Zea mays
<220> FEATURE:
<221> NAME/KEY: misc_feature
<222> LOCATION: (1)..(439)
<223> OTHER INFORMATION: DNA sequence of an EXP, EXP-Zm.Zmg13:2
      comprising a promoter (P-Zm.Zmg13:2), operably linked 5' to a
      leader (L-Zm.Zmg13:2).

<400> SEQUENCE: 30
cgtgacattt gtccaagtac tatgctaaat atgagaagct gccatttagt gattctatat       60
actattcact tatggataca tttaactgat accgttttgt tgagcgcgtc ttatttagtt      120
ttacatagca gcatagaaga ttagaagtcg caaatccaac ttttgtggac cgctgaaaaa      180
ctcaaccaaa ttcgacatat ttttcacctc cccatgccac aaaactaggt caaaacggct      240
ttctgccgtc ggccactatt tctacgggca gccagacaaa tcttcgggtc tcgcagatta      300
tttaaggaca ccacaggctg cgttacgaaa ccaggccaga tttgccaccc tcgtctcacc      360
ctccctccct cacacaaata tttcctccga catccacaag aggggagggg aaaacacgta      420
cattcacccg gcggcaata                                                   439

<210> SEQ ID NO 31
<211> LENGTH: 380
<212> TYPE: DNA
<213> ORGANISM: Zea mays
<220> FEATURE:
<221> NAME/KEY: misc_feature
<222> LOCATION: (1)..(380)
<223> OTHER INFORMATION: DNA sequence of a promoter, P-Zm.Zmg13:2.

<400> SEQUENCE: 31
cgtgacattt gtccaagtac tatgctaaat atgagaagct gccatttagt gattctatat       60
actattcact tatggataca tttaactgat accgttttgt tgagcgcgtc ttatttagtt      120
ttacatagca gcatagaaga ttagaagtcg caaatccaac ttttgtggac cgctgaaaaa      180
ctcaaccaaa ttcgacatat ttttcacctc cccatgccac aaaactaggt caaaacggct      240
ttctgccgtc ggccactatt tctacgggca gccagacaaa tcttcgggtc tcgcagatta      300
tttaaggaca ccacaggctg cgttacgaaa ccaggccaga tttgccaccc tcgtctcacc      360
ctccctccct cacacaaata                                                  380

<210> SEQ ID NO 32
```

-continued

```
<211> LENGTH: 59
<212> TYPE: DNA
<213> ORGANISM: Zea mays
<220> FEATURE:
<221> NAME/KEY: misc_feature
<222> LOCATION: (1)..(59)
<223> OTHER INFORMATION: DNA sequence of a leader, L-Zm.Zmg13:2.

<400> SEQUENCE: 32
tttcctccga catccacaag aggggagggg aaaacacgta cattcacccg gcggcaata          59

<210> SEQ ID NO 33
<211> LENGTH: 2261
<212> TYPE: DNA
<213> ORGANISM: Artificial
<220> FEATURE:
<223> OTHER INFORMATION: DNA sequence of an EXP, EXP-Zm.Waxy+Zm.DnaK:1:5
      comprising a promoter (P-Zm.Waxy-1:1:9), operably linked 5' to a
      leader (L-Zm.Waxy-1:1:1), operably linked 5' to an intron
      (I-Zm.DnaK:1).

<400> SEQUENCE: 33
aaatttcatg gtagttggga gcctacccag atttcatgat taactgtgct attgaattgt          60
tgaaaatggt tgtgtctgtc gtatccgacg gataacggaa acccgtccga aattcaatgg         120
gcatgggcat agatatagat ttgtacccac tactagtatg gtcgcaggcg gatattggtt         180
gcaaccgcag atatagtttc ggggaaaagg attaggctca gctccatccc tagaccccac         240
ttgtgtgtgt gggggggtct acccttcaaa aggaaaaaaa actacacaca gtgcatataa         300
gaagatgaat attccaaaat tcagcagtca agaagccctg ataaactgtc tggcatagct         360
agtactttat acacttcaag accaaaagaa atcactaagt acagattta gtgactcgta          420 agtacagata tcatcttaca aggcccagcc cagcgaccta ttacacagcc cgctcgggcc         480
cgcgacgtcg ggacacatct tcttccccct tttggtgaag ctctgctcgc agctgtccgg         540
ctgcttggac gttcgtgtgg cagattcatc tgtcgtctcg tctcctgtgc ttcctgggta         600
gcttgtgcag tggagctgac atggtctgag caggcttaaa atttgctcgt agacgaggag         660
taccagcaca gcacgttgcg gatttctctg cctgtgaagt gcaacgtcta ggattgtcac         720
acgccttggt cgcgtcgatg cggtggtgag cagagcagca acagctgggc ggcccaaagt         780
tggcttccgt gtcttcgtcg tacgtacgcg cgcgccgggg acacgcagag agcggagagc         840
gagccgtgca cggggggagt ggtgtgcaag tgcagccgcg cgcccgcgcc cgcgcccggt         900
gggcaaccca aaagtaccca cgacaagcga aggcgccaaa gcgatccaag ctccggaacg         960
catcagccac aagcagccga gaaccgaacc ggtgggcgac gcgtcgtggg acggacgcgg        1020
gcgacgcttc caaacggggc cacgtacgcc ggcgtgtgcg tgcgtgcgtg cagacgacaa        1080
gccaaggcga ggcagccccc gatcgggaaa gcgttttggg cgcgagcgct ggcgtgcggg        1140
tcagtcgctg gtgcgcagtg ccgggggaa cgggtatcgt ggggggcgcg ggcggaggag         1200
agcgtggcga gggccgagag cagcgcgcgg ccgggtcacg caacgcgccc cacgtactgc        1260 cctcccctc cgcgcgcgct agaaataccg aggcctggac cgggggcccc cccgtcacat         1320
ccatccatcg accgatcgat cgccacagcc aacaccaccc gccgaggcga cgcgacagcc        1380
gccaggagga aggaataaac tcactgccag ccagtgaagg gggagaagtg tactgctccg        1440
tcgactctag aggatctacc gtcttcggta cgcgctcact ccgccctctg cctttgttac        1500
tgccacgttt ctctgaatgc tctcttgtgt ggtgattgct gagagtggtt tagctggatc        1560
tagaattaca ctctgaaatc gtgttctgcc tgtgctgatt acttgccgtc ctttgtagca        1620
```

-continued

```
gcaaaatata gggacatggt agtacgaaac gaagatagaa cctacacagc aatacgagaa      1680
atgtgtaatt tggtgcttag cggtatttat ttaagcacat gttggtgtta tagggcactt      1740
ggattcagaa gtttgctgtt aatttaggca caggcttcat actacatggg tcaatagtat      1800
agggattcat attataggcg atactataat aatttgttcg tctgcagagc ttattatttg      1860
ccaaaattag atattcctat tctgtttttg tttgtgtgct gttaaattgt taacgcctga      1920
aggaataaat ataaatgacg aaattttgat gtttatctct gctcctttat tgtgaccata      1980
agtcaagatc agatgcactt gttttaaata ttgttgtctg aagaaataag tactgacagt      2040
attttgatgc attgatctgc ttgtttgttg taacaaaatt taaaaataaa gagtttcctt      2100
tttgttgctc tccttacctc ctgatggtat ctagtatcta ccaactgaca ctatattgct      2160
tctctttaca tacgtatctt gctcgatgcc ttctccctag tgttgaccag tgttactcac      2220
atagtctttg ctcatttcat tgtaatgcag ataccaagcg g                         2261
```

```
<210> SEQ ID NO 34
<211> LENGTH: 1312
<212> TYPE: DNA
<213> ORGANISM: Zea mays
<220> FEATURE:
<221> NAME/KEY: misc_feature
<222> LOCATION: (1)..(1312)
<223> OTHER INFORMATION: DNA sequence of a promoter, P-Zm.Waxy-1:1:9.

<400> SEQUENCE: 34
aaatttcatg gtagttggga gcctacccag atttcatgat taactgtgct attgaattgt        60
tgaaaatggt tgtgtctgtc gtatccgacg gataacggaa acccgtccga aattcaatgg       120
gcatgggcat agatatagat ttgtacccac tactagtatg gtcgcaggcg gatattggtt       180
gcaaccgcag atatagtttc ggggaaaagg attaggctca gctccatccc tagaccccac       240
ttgtgtgtgt gggggggtct acccttcaaa aggaaaaaaa actacacaca gtgcatataa       300
gaagatgaat attccaaaat tcagcagtca agaagccctg ataaactgtc tggcatagct       360
agtactttat acacttcaag accaaaagaa atcactaagt acagatttta gtgactcgta       420
agtacagata tcatcttaca aggcccagcc cagcgaccta ttacacagcc cgctcgggcc       480
cgcgacgtcg ggacacatct tcttcccct tttggtgaag ctctgctcgc agctgtccgg       540
ctgcttggac gttcgtgtgg cagattcatc tgtcgtctcg tctcctgtgc ttcctgggta       600
gcttgtgcag tggagctgac atggtctgag caggcttaaa atttgctcgt agacgaggag       660
taccagcaca gcacgttgcg gatttctctg cctgtgaagt gcaacgtcta ggattgtcac       720
acgccttggt cgcgtcgatg cggtggtgag cagagcagca acagctgggc ggcccaaagt       780
tggcttccgt gtcttcgtcg tacgtacgcg cgcgccgggg acacgcagag agcggagagc       840
gagccgtgca cgggggaggt ggtgtgcaag tgcagccgcg cgcccgcgcc cgcgcccggt       900
gggcaaccca aaagtaccca cgacaagcga aggcgccaaa gcgatccaag ctccggaacg       960
catcagccac aagcagccga gaaccgaacc ggtgggcgac gcgtcgtggg acggacgcgg      1020
gcgacgcttc caaacggggc cacgtacgcc ggcgtgtgcg tgcgtgcgtg cagacgacaa      1080
gccaaggcga ggcagccccc gatcgggaaa gcgttttggg cgcgagcgct ggcgtgcggg      1140
tcagtcgctg gtgcgcagtg ccggggggaa cgggtatcgt ggggggcgcg ggcggaggag      1200
agcgtggcga gggccgagag cagcgcgcgg ccgggtcacg caacgcgccc cacgtactgc      1260 cctcccctc cgcgcgcgct agaaataccg aggcctggac cggggggcccc cc              1312
```

```
<210> SEQ ID NO 35
<211> LENGTH: 127
<212> TYPE: DNA
<213> ORGANISM: Zea mays
<220> FEATURE:
<221> NAME/KEY: misc_feature
<222> LOCATION: (1)..(127)
<223> OTHER INFORMATION: DNA sequence of a leader, L-Zm.Waxy-1:1:1.

<400> SEQUENCE: 35
cgtcacatcc atccatcgac cgatcgatcg ccacagccaa caccacccgc cgaggcgacg        60
cgacagccgc caggaggaag gaataaactc actgccagcc agtgaagggg gagaagtgta       120
ctgctcc                                                                 127

<210> SEQ ID NO 36
<211> LENGTH: 983
<212> TYPE: DNA
<213> ORGANISM: Arabidopsis thaliana
<220> FEATURE:
<221> NAME/KEY: misc_feature
<222> LOCATION: (1)..(983)
<223> OTHER INFORMATION: DNA sequence of an EXP, EXP-Syn1 comprised of a
      promoter and leader.

<400> SEQUENCE: 36
tgagaatgaa gacgaagtac aagaatcaga tgaactgtcc tgggcaatct ccccattagc        60
cgcaacgatg gtgcgggaat aacagctgaa ttcatcgata tagctaagac tctgtttttgt      120 gctcgcttca ccagccaaga cattgtgatc ttcaacctcc atccaaccct ctgagtcttg       180
tctgctataa acttggatca aagcctctcc atctgaatgt gtctcattca aggcgtgtga       240
aacattcgtc acgagcatat acgtatcctt gtcgttggtt aaccctctaa gagtagaagt       300
gatcactgta agaggatatg tccgctggtg cacgactcga ttcaccggtt tacccgattc       360
agaagtcacc tccacgatcc gttcggtctt cactctctgc tcaaccctct tgtatgttcc       420
gtttttctcg aacctcacca agctgtcaac cttgaacatg ctcttgacca tggtggtcag       480
attaccttta cttgatctaa cccagccatc atattcacta cttacctctg cttcaacctt       540
aaacgaccca tcaagctgtt caagctgttc ttgtctcatc atatgccgac tcgggctatc       600
ataaagtcta gacccagctt caacattcga agaccgtga tctaaccaga ggtgcaaatt        660
agcgtccaca agccagtatg atatcccatc gttgacccca aacgcaaact catgagactt       720
tccatctaaa agcaacccga gaaatggcgt caagtccatg tcataggaag gtagattgaa       780
ggcaccgatt gctacaactg gttcccagaa caagggattg attccaccag taaagatcac       840
cggaaatggc acctcggatc ccacgtatct cccatctatc ttaacaaaaa cttcccggta       900
tgcaccattg ccacgcccgg ttgttagatt gttcgttctg atataagaat ttggcgggtt       960
tgaataccag aactcatcgt ttc                                               983

<210> SEQ ID NO 37
<211> LENGTH: 2317
<212> TYPE: DNA
<213> ORGANISM: Arabidopsis thaliana
<220> FEATURE:
<221> NAME/KEY: misc_feature
<222> LOCATION: (1)..(2317)
<223> OTHER INFORMATION: DNA sequence of an EXP, EXP-Syn1a comprised of
      a promoter and leader.

<400> SEQUENCE: 37
tgagaatgaa gacgaagtac aagaatcaga tgaactgtcc tgggcaatct ccccattagc        60
```

-continued

```
cgcaacgatg gtgcgggaat aacagctgaa ttcatcgata tagctaagac tctgttttgt       120
gctcgcttca ccagccaaga cattgtgatc ttcaacctcc atccaaccct ctgagtcttg       180
tctgctataa acttggatca aagcctctcc atctgaatgt gtctcattca aggcgtgtga       240
aacattcgtc acgagcatat acgtatcctt gtcgttggtt aaccctctaa gagtagaagt       300
gatcactgta agaggatatg tccgctggtg cacgactcga ttcaccggtt tacccgattc       360
agaagtcacc tccacgatcc gttcggtctt cactctctgc tcaaccctct tgtatgttcc       420
gtttttctcg aacctcacca agctgtcaac cttgaacatg ctcttgacca tggtggtcag       480
attaccttta cttgatctaa cccagccatc atattcacta cttacctctg cttcaacctt       540
aaacgaccca tcaagctgtt caagctgttc ttgtctcatc atatgccgac tcgggctatc       600
ataaagtcta gacccagctt caacattcga agacccgtga tctaaccaga ggtgcaaatt       660
agcgtccaca agccagtatg atatcccatc gttgacccca aacgcaaact catgagactt       720
tccatctaaa agcaacccga gaaatggcgt caagtccatg tcataggaag gtagattgaa       780
ggcaccgatt gctacaactg gttcccagaa caagggattg attccaccag taaagatcac       840
cggaaatggc acctcggatc ccacgtatct cccatctatc ttaacaaaaa cttcccggta       900
tgcaccattg ccacgcccgg ttgttagatt gttcgttctg atataagaat ttggcgggtt       960
tgaataccag aactcatcgt ttccctggaa cgatacatat agttccagca caatctgacg      1020
agtgttggac ggaatttgaa ttccttttga gtaagtttct ctggggttct cgatcatgaa      1080
ccagaaccct ctgttccctc cgtcacatac cggaattatc aaatccgcag gggtttgatc      1140
tcttttctgg gaatctacaa accctaatct gttactaatc ttcaaatttg acgcaatagg      1200
attgaattcg tagaagatga gggtgacatt gatatgatag atgcctgtgt aaacatcgtt      1260
gactatgttc tcaagcatca ttgtgacatt taaatcggat ctcataaaga gcgaggaata      1320
cctagagacg tctttccgaa cattccagaa gattccggat ggactcggct ccgccgtact      1380
ggtgcgaagt agctccactc cgccgagcca caagccggag atacgatcgt actgatcgcc      1440
actcgaggcg gcgcgtaggt caagtacaac ataagaccac ggcggcgata tgcagctgga      1500 aggggggagtg tatggagtgg taaaaggggg tctgttgatg gtgttggcga atgaatggcg      1560
gaagaggaca tgcgagcatg acggcgttag ctgatcggac ggtaggggcc gcctgagctc      1620
ctcgtactcc tgaggctcga ccggtgaccg gagacaagtc gaagccgatc taaggaatcg      1680
atccggcgag gaaggacgag aaacggcggt agcagtgaga aaagcaagtg tgaagaagaa      1740
cttaacggcg ccgttttgat tttctggcat gatagcttct gtgtttttga ttatccgagc      1800
tcgccgatgc gaacttcaat ggagactgga gagagagaag ggacgtaatt aaacaccaaa      1860
gcgtttttat atttcggaga atcaactacg tgtcgtttga catcctaaat tggcagatag      1920
tagaaaggaa atgttgagac tggagagttt gatagtaaca gtgtgtgggac cagcgacggt      1980 aacggaattc gaaatttatt ttagcgtcac gtgtggttac ttataatctg tgcacgtgtc      2040
aaaataagag agggctacta gtgacacttt cgtcactgtc acttaatttt agcctttctc      2100
ctgacatgct tactctctcc tctcccgcta cgatcactgc gagttttccc ttcttaagct      2160
ctcatggcgg cttcataaat ctatatacag acaaatttac acataaagaa acgcattaaa      2220
aaaactattt actcagattc agcttcttct ccacgcaaag actcgcttct ctttttttct      2280
cttcctgagt ttggattttt tttgcttgag ctgaatc                              2317
```

<210> SEQ ID NO 38
<211> LENGTH: 521

```
<212> TYPE: DNA
<213> ORGANISM: Arabidopsis thaliana
<220> FEATURE:
<221> NAME/KEY: misc_feature
<222> LOCATION: (1)..(521)
<223> OTHER INFORMATION: DNA sequence of a 3' UTR, T-At.Syn1-1:2:1.

<400> SEQUENCE: 38
ggtttgattt ctaaattata aaagattctg gtgaaccgat tatccatagt tgttttgctt        60
ttcatattct agcagagaga gttcgtagac tttttttaagt tataaagagc aagcgttctt       120
tacccaaatt cctctgtttg gtccttttgt tatatggtta ttagtacctc atacatcatc       180
acatcctagc tttgtccgaa aacatctgaa actaatttt  acattattct ataatttaag       240
tattttactc gcatatattg agtcttctta gaagatgtat tgaacagagc ataaacaaaa       300
caatagttta atatatactc cgttgacaaa gaaaatggtg gcagtcacgt aataagccgc       360
aactgccccc atttcataca atacatgtat aatcttcata attagtcgct cacacgtttc       420
atacaatttg tcaaatttct caaaaaatta aactaattac acaatcaaat accagcctct       480
atatgtttct atatatacgc atatttctta ccccctgaat c                          521

<210> SEQ ID NO 39
<211> LENGTH: 804
<212> TYPE: DNA
<213> ORGANISM: Zea mays
<220> FEATURE:
<221> NAME/KEY: misc_feature
<222> LOCATION: (1)..(804)
<223> OTHER INFORMATION: DNA sequence of an intron, I-Zm.DnaK:1.

<400> SEQUENCE: 39
accgtcttcg gtacgcgctc actccgccct ctgcctttgt tactgccacg tttctctgaa        60
tgctctcttg tgtggtgatt gctgagagtg gtttagctgg atctagaatt acactctgaa       120
atcgtgttct gcctgtgctg attacttgcc gtcctttgta gcagcaaaat atagggacat       180
ggtagtacga aacgaagata gaacctacac agcaatacga gaaatgtgta atttggtgct       240
tagcggtatt tatttaagca catgttggtg ttatagggca cttggattca gaagtttgct       300
gttaatttag gcacaggctt catactacat gggtcaatag tatagggatt catattatag       360
gcgatactat aataaatttgt tcgtctgcag agcttattat ttgccaaaat tagatattcc       420
tattctgttt ttgtttgtgt gctgttaaat tgttaacgcc tgaaggaata aatataaatg       480
acgaaatttt gatgtttatc tctgctcctt tattgtgacc ataagtcaag atcagatgca       540
cttgttttaa atattgttgt ctgaagaaat aagtactgac agtattttga tgcattgatc       600
tgcttgtttg ttgtaacaaa atttaaaaat aaagagtttc cttttgttg ctctccttac        660 ctcctgatgg tatctagtat ctaccaactg acactatatt gcttctcttt acatacgtat       720
cttgctcgat gccttctccc tagtgttgac cagtgttact cacatagtct ttgctcattt       780
cattgtaatg cagataccaa gcgg                                             804

<210> SEQ ID NO 40
<211> LENGTH: 3960
<212> TYPE: DNA
<213> ORGANISM: Artificial
<220> FEATURE:
<223> OTHER INFORMATION: DNA sequence of an EXP, EXP-At.Dmc1+Zm.DnaK:1:1
      comprised of a promoter (P-At.Dmc1:1), operably linked 5' to a
      leader (L-At.Dmc1-1:1:1), operably linked 5' to an intron
      (I-Zm.DnaK:1).

<400> SEQUENCE: 40
```

-continued

```
gttaacaccg tttatatgag acaaaatcag ctatgagatt actcgtgtat caattctcta        60
attaattaaa aatagtataa attaaataat atagttcgat acacgaatat aattgcgaag       120
aataggcata caaatttgtc atacatgttt cgatatggct cacgaggagg ctgatgcaac       180
agtttgatgt atacgtatgc aaattgagaa gtacttgatc agacctatat atgtgatgct       240
cgaacttatc tttttgtttt ggatcatcta tcgaatacaa tggtactata atttaaatgt       300
tttttttctt ctttttcttt agtatcaaaa gcaacgttag atgctaaata aagagttagt       360
tgattgtgat gactgatagt ctgataatat cattaacttt gcacccgaag tcaaataaaa       420
gtgttcatat ttataaattc caaccaacgt taataagcca cacctaatcg gtgattgcca       480
acaatattat aataaaatta aaaaaactac gactaaagtt aatttgctat aattttgtgg       540 tatgtttttaa aaataaagtt ctttagttct aatatcatga aaattcagtg tactgtaaaa       600
tatgtaaaaa ggttttagta caattctttt ttgtatataa cggcaaagtt caatacatat       660
tttactattg attttttta aaaataaaat aacaattgct accaacttt tgaagcatat        720 tgatcgcaac ttaattataa ttcttctttt ttttcttgga agattaataa aacctaattt       780
caatgtggaa caaataaatg tagaaatatt gttatcacaa actaatatat gatatttttt       840
aatattttca tatatacttt tgagcttctg atgatataac agttttcatt aaaatacaaa       900
ttgtcgtgta ctaatttttc ttttgttcaa gtatgtgata aaaatatgtt gcaaaattgc       960
gagttattat aatggtacaa atatgtagag agaatacatg agaagagtta aaagaagcat      1020
gcttaagcca acagagagtg gatccaaatg ttgctttcca gctttataca aacgtatcac      1080
ccacattact gccactgcta catatattga aggagagaga gatgatgatc ataatgataa      1140
atcgatgtcg atgataaatt gatgatgatg gctccggtat gtgtacccta ggagttgtag      1200
ctagctagct aggaccatgt atatacatac atacatatat tagtgttttt tgtaacttgt      1260
acgtacctta caaacagtat ggagtttact aaaacggcaa cgtttggtgg gggtagtgaa      1320
ttcgcaagtg gggatgagtc tatgtaatag aagatgcaac atgcaaatgg tcccctttct      1380
gtttttattt aaagaaatta gtgtttactg aggaggaaac atcccattta tagattcaca      1440
cccataaaag caaaccactt ctccttcttt ttatttcccc atgatattac ttcgagaata      1500
ttttgaaaat ttgaagtgta catttagaga ttgtgtactt tgaacactca tgtcaaatgc      1560
atctaaatat ataaactcca atttaaaata atcgtctaaa cctagagtgc catttgttta      1620
gccatttgtt ggtcttcatt tctcatgctt tgattacatg taccggttga ttcatgtgaa      1680
aaatcatgtg cataaactaa gaaatagcta gcacataaaa ttttgattta ggttggatat      1740
tactatgttc actttaagag aaaaaaaaac ttatggcaaa aagtgatgat ggtatatgaa      1800
tatgataatc aaagtgcata tgtgaagtga gaggcaactg tagagtaata taataaaatc      1860
caaagaaaat ttttaaatat gagaaaaaat tatataaaaa ggttctttg taatccactt       1920 cttttgatat agggagattc gttgagcatc catgtgctct ttcaatcgac actattctgt      1980
ctgtatctag ccaacccaca tataccttta cactagagaa cttcgatgat tcttttcca       2040 aaatcaatgt gatataatat aattaagcat atatgcataa aaaatgaaga agaatggtag      2100
agtcatgtta cttaaggtca tggtgtgtaa aaacattgat actttacaat atatgagttg      2160
tgaagtgctc ttaaagttat aacatccggt tctacgtatt gacctagaac tagaagaatc      2220
gttttttagt ccaaatcaaa tcaagtcggt tctttatcag ttttgttgta tgtgaattaa      2280
tttgaaaata ttagctatga tcttagcttg ggttttttgtt tctaagggtt aaggatcata     2340
```

-continued

```
tctctttgtc aaatgacatg tggtctatat gtcatgaatt aggcaccgct atcttttact      2400
attgattcga cgacattggg actcctcact acacttatct taaaaaaact caaagttggt      2460
gttaatggct tgtcaccata aactttcatg agctctaaca aattaaactt gaacttgatc      2520
aggtctcaca atatatacaa tttcgaggga taaatatttc aaaaggataa tatgatagtt      2580
ggtagaaatg tatagtttct agtaataata gagatcgttg gttaaactcc ccaacttttt      2640
aaaattaatt tgattagtgg atccgcaaac aaatattaga ttgggcctat atgcatctat      2700
attattttta tttttctgta atttcagtaa aatgggccta tggtcctata tgcatccgaa      2760
taattagtat actgggctta tgggcctata tgcatttgat tttatcgata aaatgtgagt      2820
caaatgtcta atgtgcgccg ttatgaagtg caagtggcta attttttttca cctagattcc      2880 ttctattgac cgtcgataga cggatgataa ctatgacgtg gcattatcgc agccatcaaa      2940
caaagtcatg tataacaaac aagagcacac aaacgaaaac aaattcagtt gcggaaccca      3000
aattcaaatc aacggaatta gaatcacgct ttcaattccg taacccgcca ttaaaaacct      3060
tgaaccctcg aagcaaatcg agcaaagatt ttcaaatttc gaatttcaaa attctatctc      3120
tctcactctt ccaagcttag agagtcttag agcgagaaac ggaccgaccg tcttcggtac      3180
gcgctcactc cgccctctgc ctttgttact gccacgtttc tctgaatgct ctcttgtgtg      3240
gtgattgctg agagtggttt agctggatct agaattacac tctgaaatcg tgttctgcct      3300
gtgctgatta cttgccgtcc tttgtagcag caaaatatag ggacatggta gtacgaaacg      3360
aagatagaac ctacacagca atacgagaaa tgtgtaattt ggtgcttagc ggtatttatt      3420
taagcacatg ttggtgttat agggcacttg gattcagaag tttgctgtta atttaggcac      3480
aggcttcata ctacatgggt caatagtata gggattcata ttataggcga tactataata      3540
atttgttcgt ctgcagagct tattatttgc caaaattaga tattcctatt ctgtttttgt      3600
ttgtgtgctg ttaaattgtt aacgcctgaa ggaataaata taaatgacga aattttgatg      3660
tttatctctg ctcctttatt gtgaccataa gtcaagatca gatgcacttg tttttaaatat      3720 tgttgtctga agaaataagt actgacagta ttttgatgca ttgatctgct tgtttgttgt      3780
aacaaaattt aaaaataaag agtttccttt ttgttgctct ccttacctcc tgatggtatc      3840
tagtatctac caactgacac tatattgctt ctctttacat acgtatcttg ctcgatgcct      3900
tctccctagt gttgaccagt gttactcaca tagtctttgc tcatttcatt gtaatgcaga      3960
```

<210> SEQ ID NO 41
<211> LENGTH: 3083
<212> TYPE: DNA
<213> ORGANISM: Arabidopsis thaliana
<220> FEATURE:
<221> NAME/KEY: misc_feature
<222> LOCATION: (1)..(3083)
<223> OTHER INFORMATION: DNA sequence of a promoter, P-At.Dmc1:1.

<400> SEQUENCE: 41

```
gttaacaccg tttatatgag acaaaatcag ctatgagatt actcgtgtat caattctcta       60
attaattaaa aatagtataa attaaataat atagttcgat acacgaatat aattgcgaag      120
aataggcata caaatttgtc atacatgttt cgatatggct cacgaggagg ctgatgcaac      180
agtttgatgt atacgtatgc aaattgagaa gtacttgatc agacctatat atgtgatgct      240
cgaacttatc ttttttgtttt ggatcatcta tcgaatacaa tggtactata atttaaatgt      300
tttttttctt cttttttcttt agtatcaaaa gcaacgttag atgctaaata aagagttagt      360
tgattgtgat gactgatagt ctgataatat cattaacttt gcacccgaag tcaaataaaa      420
```

-continued

```
gtgttcatat ttataaattc caaccaacgt taataagcca cacctaatcg gtgattgcca      480
acaatattat aataaaatta aaaaaactac gactaaagtt aatttgctat aattttgtgg      540
tatgttttaa aaataaagtt ctttagttct aatatcatga aaattcagtg tactgtaaaa      600
tatgtaaaaa ggttttagta caattctttt ttgtatataa cggcaaagtt caatacatat      660
tttactattg attttttta aaaataaaat aacaattgct accaacttt tgaagcatat        720 tgatcgcaac ttaattataa ttcttctttt ttttcttgga agattaataa aacctaattt      780
caatgtggaa caaataaatg tagaaatatt gttatcacaa actaatatat gatattttt       840 aatattttca tatatacttt tgagcttctg atgatataac agtttcatt aaaatacaaa       900 ttgtcgtgta ctaatttttc ttttgttcaa gtatgtgata aaaatatgtt gcaaaattgc      960
gagttattat aatggtacaa atatgtagag agaatacatg agaagagtta aaagaagcat     1020
gcttaagcca acagagagtg gatccaaatg ttgctttcca gctttataca aacgtatcac     1080
ccacattact gccactgcta catatattga aggagagaga gatgatgatc ataatgataa     1140
atcgatgtcg atgataaatt gatgatgatg gctccggtat gtgtaccta ggagttgtag      1200 ctagctagct aggaccatgt atatacatac atacatatat tagtgtttt tgtaacttgt      1260 acgtaccttat caaacagtat ggagtttact aaaacggcaa cgtttggtgg gggtagtgaa    1320
ttcgcaagtg gggatgagtc tatgtaatag aagatgcaac atgcaaatgg tccccttct      1380 gttttttttt aaagaaatta gtgtttactg aggaggaaac atcccattta tagattcaca     1440
cccataaaag caaaccactt ctccttcttt ttatttcccc atgatattac ttcgagaata     1500
ttttgaaaat ttgaagtgta catttagaga ttgtgtactt tgaacactca tgtcaaatgc     1560
atctaaatat ataaactcca atttaaaata atcgtctaaa cctagagtgc catttgttta     1620
gccatttgtt ggtcttcatt tctcatgctt tgattacatg taccggttga ttcatgtgaa     1680
aaatcatgtg cataaactaa gaaatagcta gcacataaaa ttttgattta ggttggatat     1740
tactatgttc actttaagag aaaaaaaaac ttatggcaaa aagtgatgat ggtatatgaa     1800
tatgataatc aaagtgcata tgtgaagtga gaggcaactg tagagtaata taataaaatc     1860
caaagaaaat ttttaaatat gagaaaaaat tatataaaaa ggttctttg taatccactt      1920 cttttgatat agggagattc gttgagcatc catgtgctct ttcaatcgac actattctgt     1980
ctgtatctag ccaacccaca tataccttta cactagagaa cttcgatgat tcttttttcca    2040 aaatcaatgt gatataatat aattaagcat atatgcataa aaaatgaaga agaatggtag     2100
agtcatgtta cttaaggtca tggtgtgtaa aaacattgat actttacaat atatgagttg     2160
tgaagtgctc ttaaagttat aacatccggt tctacgtatt gacctagaac tagaagaatc     2220 gtttttagt ccaaatcaaa tcaagtcggt tctttatcag ttttgttgta tgtgaattaa      2280
tttgaaaata ttagctatga tcttagcttg ggtttttgtt tctaagggtt aaggatcata     2340
tctctttgtc aaatgacatg tggtctatat gtcatgaatt aggcaccgct atcttttact     2400
attgattcga cgacattggg actcctcact acacttatct taaaaaaact caaagttggt     2460
gttaatggct tgtcaccata aactttcatg agctctaaca aattaaactt gaacttgatc     2520
aggtctcaca atatatacaa tttcgaggga taaatatttc aaaaggataa tatgatagtt     2580
ggtagaaatg tatagtttct agtaataata gagatcgttg gttaaactcc ccaactttt      2640 aaaattaatt tgattagtgg atccgcaaac aaatattaga ttgggcctat atgcatctat     2700
attattttta tttttctgta atttcagtaa aatgggccta tggtcctata tgcatccgaa     2760
```

```
taattagtat actgggctta tgggcctata tgcatttgat tttatcgata aaatgtgagt    2820
caaatgtcta atgtgcgccg ttatgaagtg caagtggcta attttttttca cctagattcc    2880 ttctattgac cgtcgataga cggatgataa ctatgacgtg gcattatcgc agccatcaaa    2940
caaagtcatg tataacaaac aagagcacac aaacgaaaac aaattcagtt gcggaaccca    3000
aattcaaatc aacggaatta gaatcacgct ttcaattccg taacccgcca ttaaaaacct    3060
tgaaccctcg aagcaaatcg agc                                            3083
```

```
<210> SEQ ID NO 42
<211> LENGTH: 76
<212> TYPE: DNA
<213> ORGANISM: Arabidopsis thaliana
<220> FEATURE:
<221> NAME/KEY: misc_feature
<222> LOCATION: (1)..(76)
<223> OTHER INFORMATION: DNA sequence of a leader, L-At.Dmc1-1:1:1.

<400> SEQUENCE: 42
aaagattttc aaatttcgaa tttcaaaatt ctatctctct cactcttcca agcttagaga     60
gtcttagagc gagaaa                                                      76
```

```
<210> SEQ ID NO 43
<211> LENGTH: 1221
<212> TYPE: DNA
<213> ORGANISM: Artificial
<220> FEATURE:
<223> OTHER INFORMATION: A coding sequence for Cre-recombinase (Cre)
      with a processable intron derived from the potato light-inducible
      tissue-specific ST-LS1 gene (Genbank Accession: X04753).

<400> SEQUENCE: 43
atgtccaatt tactgaccgt acaccaaaat ttgcctgcat taccggtcga tgcaacgagt     60
gatgaggttc gcaagaacct gatggacatg ttcagggatc gccaggcgtt ttctgagcat    120
acctggaaaa tgcttctgtc cgtttgccgg tcgtgggcgg catggtgcaa gttgaataac    180
cggaaatggt ttcccgcaga acctgaagat gttcgcgatt atcttctata tcttcaggcg    240
cgcggtctgg cagtaaaaac tatccagcaa catttgggcc agctaaacat gcttcatcgt    300
cggtccgggc tgccacgacc aagtgacagc aatgctgttt cactggttat gcggcggatc    360
cgaaaagaaa acgttgatgc cggtgaacgt gcaaaacagg ctctagcgtt cgaacgcact    420
gatttcgacc aggtaagttt ctgcttctac ctttgatata tatataataa ttatcattaa    480
ttagtagtaa tataatattt caaatatttt tttcaaaata aaagaatgta gtatatagca    540
attgcttttc tgtagtttat aagtgtgtat attttaattt ataacttttc taatatatga    600
ccaaaatttg ttgatgtgca ggttcgttca ctcatggaaa atagcgatcg ctgccaggat    660
atacgtaatc tggcatttct ggggattgct tataacaccc tgttacgtat agccgaaatt    720
gccaggatca gggttaaaga tatctcacgt actgacggtg ggagaatgtt aatccatatt    780
ggcagaacga aaacgctggt tagcaccgca ggtgtagaga aggcacttag cctgggggta    840
actaaactgg tcgagcgatg gatttccgtc tctggtgtag ctgatgatcc gaataactac    900
ctgttttgcc gggtcagaaa aaatggtgtt gccgcgccat ctgccaccag ccagctatca    960
actcgcgccc tggaagggat ttttgaagca actcatcgat tgatttacgg cgctaaggat   1020
gactctggtc agagatacct ggcctggtct ggacacagtg cccgtgtcgg agccgcgcga   1080
gatatggccc gcgctggagt ttcaataccg gagatcatgc aagctggtgg ctggaccaat   1140
gtaaatattg tcatgaacta tatccgtaac ctggatagtg aaacaggggc aatggtgcgc   1200
```

-continued

```
ctgctggaag atggcgatta g                                                    1221

<210> SEQ ID NO 44
<211> LENGTH: 34
<212> TYPE: DNA
<213> ORGANISM: Enterobacteria phage P1
<220> FEATURE:
<221> NAME/KEY: misc_feature
<222> LOCATION: (1)..(34)
<223> OTHER INFORMATION: DNA sequence of a Cre-recombinase site-specific
      recombination site, RS-P1.lox1:1.

<400> SEQUENCE: 44
ataacttcgt atagcataca ttatacgaag ttat                                        34

<210> SEQ ID NO 45
<211> LENGTH: 34
<212> TYPE: DNA
<213> ORGANISM: Artificial
<220> FEATURE:
<223> OTHER INFORMATION: DNA sequence of a Cre-recombinase site-specific
      recombination site, RS-P1.lox.TATA-R9-1:1:1.

<400> SEQUENCE: 45
ataacttcgg atagcataca ttatccgaag gaca                                        34

<210> SEQ ID NO 46
<211> LENGTH: 1399
<212> TYPE: DNA
<213> ORGANISM: Oryza sativa
<220> FEATURE:
<221> NAME/KEY: misc_feature
<222> LOCATION: (1)..(1399)
<223> OTHER INFORMATION: DNA sequence of an EXP, EXP-Os.Act1:1:1
      comprised of a promoter, leader, and intron derived from the Rice
      Actin 1 gene.

<400> SEQUENCE: 46
tcgaggtcat tcatatgctt gagaagagag tcgggatagt ccaaaataaa acaaaggtaa      60
gattacctgg tcaaaagtga aaacatcagt taaaagtgg tataaagtaa aatatcggta        120
ataaaaggtg gcccaaagtg aaatttactc ttttctacta ttataaaaat tgaggatgtt      180
tttgtcggta ctttgatacg tcatttttgt atgaattggt ttttaagttt attcgctttt      240
ggaaatgcat atctgtattt gagtcgggtt ttaagttcgt ttgctttgt aaatacagag       300 ggatttgtat aagaaatatc tttagaaaaa cccatatgct aatttgacat aattttttgag     360 aaaaatatat attcaggcga attctcacaa tgaacaataa taagattaaa atagctttcc      420
cccgttgcag cgcatgggta ttttttctag taaaaataaa agataaactt agactcaaaa      480
catttacaaa aacaaccct aaagttccta aagcccaaag tgctatccac gatccatagc       540
aagcccagcc caacccaacc caacccaacc caccccagtc cagccaactg gacaatagtc      600
tccacacccc cccactatca ccgtgagttg tccgcacgca ccgcacgtct cgcagccaaa      660 aaaaaaaga aagaaaaaa agaaaaagaa aaaacagcag gtgggtccgg gtcgtggggg      720
ccggaaacgc gaggaggatc gcgagccagc gacgaggccg gccctccctc cgcttccaaa     780
gaaacgcccc ccatcgccac tatatacata cccccccctc tcctcccatc ccccaaccc      840 taccaccacc accaccacca cctccacctc ctcccccctc gctgccggac gacgagctcc      900
tcccccctcc cctccgccg ccgccgcgcc ggtaaccacc ccgcccctct cctctttctt      960
tctccgtttt tttttccgtc tcggtctcga tctttggcct tggtagtttg ggtgggcgag     1020
```

-continued

```
aggcggcttc gtgcgcgccc agatcggtgc gcgggagggg cgggatctcg cggctggggc    1080
tctcgccggc gtggatccgg cccggatctc gcggggaatg gggctctcgg atgtagatct    1140
gcgatccgcc gttgttgggg gagatgatgg ggggtttaaa atttccgccg tgctaaacaa    1200
gatcaggaag aggggaaaag ggcactatgg tttatatttt tatatatttc tgctgcttcg    1260
tcaggcttag atgtgctaga tctttctttc ttcttttgt gggtagaatt tgaatccctc     1320
agcattgttc atcggtagtt tttcttttca tgatttgtga caaatgcagc ctcgtgcgga    1380 gctttttgt aggtagaag                                                   1399
```

<210> SEQ ID NO 47
<211> LENGTH: 1596
<212> TYPE: DNA
<213> ORGANISM: Artificial
<220> FEATURE:
<223> OTHER INFORMATION: A coding sequence for a plastid targeted EPSPS,
      CP4 that confers tolerance to the herbicide, glyphosate.

<400> SEQUENCE: 47

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat gcttcacggt     240
gcaagcagcc ggcccgcaac cgcccgcaaa tcctctggcc tttccggaac cgtccgcatt     300
cccggcgaca agtcgatctc ccaccggtcc ttcatgttcg gcggtctcgc gagcggtgaa     360
acgcgcatca ccggccttct ggaaggcgag gacgtcatca atacgggcaa ggccatgcag     420
gcgatgggcg cccgcatccg taaggaaggc gacacctgga tcatcgatgg cgtcggcaat     480
ggcggcctcc tggcgcctga ggcgccgctc gatttcggca atgccgccac gggctgccgc     540
ctgacgatgg gcctcgtcgg ggtctacgat ttcgacagca ccttcatcgg cgacgcctcg     600
ctcacaaagc gcccgatggg ccgcgtgttg aacccgctgc gcgaaatggg cgtgcaggtg     660
aaatcggaag acggtgaccg tcttcccgtt accttgcgcg gccgaagac gccgacgccg      720 atcacctacc gcgtgccgat ggcctccgca caggtgaagt ccgccgtgct gctcgccggc     780
ctcaacacgc ccggcatcac gacggtcatc gagccgatca tgacgcgcga tcatacggaa     840
aagatgctgc agggctttgg cgccaacctt accgtcgaga cggatgcgga cggcgtgcgc     900
accatccgcc tggaaggccg cggcaagctc accggccaag tcatcgacgt gccgggcgac     960
ccgtcctcga cggccttccc gctggttgcg ccctgcttg ttccgggctc cgacgtcacc     1020
atcctcaacg tgctgatgaa ccccacccgc accggcctca tcctgacgct gcaggaaatg     1080
ggcgccgaca tcgaagtcat caacccgcgc cttgccggcg cgaagacgt ggcggacctg      1140 cgcgttcgct cctccacgct gaagggcgtc acggtgccgg aagaccgcgc gccttcgatg     1200
atcgacgaat atccgattct cgctgtcgcc gccgccttcg cggaaggggc gaccgtgatg     1260
aacggtctgg aagaactccg cgtcaaggaa agcgaccgcc tctcggccgt cgccaatggc     1320
ctcaagctca atggcgtgga ttgcgatgag ggcgagacgt cgctcgtcgt gcgtggccgc     1380
cctgacggca aggggctcgg caacgcctcg ggcgccgccg tcgccaccca tctcgatcac     1440
cgcatcgcca tgagcttcct cgtcatgggc ctcgtgtcgg aaaaccctgt cacggtggac     1500
gatgccacga tgatcgccac gagcttcccg gagttcatgg acctgatggc cgggctgggc     1560
gcgaagatcg aactctccga tacgaaggct gcctga                               1596
```

<210> SEQ ID NO 48
<211> LENGTH: 253
<212> TYPE: DNA
<213> ORGANISM: Agrobacterium tumefaciens
<220> FEATURE:
<221> NAME/KEY: misc_feature
<222> LOCATION: (1)..(253)
<223> OTHER INFORMATION: DNA sequence of a 3' UTR, T-AGRtu.nos:13.

<400> SEQUENCE: 48
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag atc                                                        253

<210> SEQ ID NO 49
<211> LENGTH: 1748
<212> TYPE: DNA
<213> ORGANISM: Artificial
<220> FEATURE:
<223> OTHER INFORMATION: DNA sequence of an EXP,
     EXP-Os.Act1+CaMV.35S.2xA1-B3+Ta.Lhcb1:1:1 comprised of an enhanced
     promoter and leader.

<400> SEQUENCE: 49
ctcgaggtca ttcatatgct tgagaagaga gtcgggatag tccaaaataa aacaaaggta      60
agattacctg gtcaaaagtg aaaacatcag ttaaaaggtg gtataaagta aaatatcggt     120
aataaaaggt ggcccaaagt gaaatttact cttttctact attataaaaa ttgaggatgt     180
ttttgtcggt actttgatac gtcatttttg tatgaattgg tttttaagtt tattcgcttt     240
tggaaatgca tatctgtatt tgagtcgggt tttaagttcg tttgcttttg taaatacaga     300
gggatttgta taagaaatat ctttagaaaa acccatatgc taatttgaca taatttttga     360
gaaaaatata tattcaggcg aattctcaca atgaacaata ataagattaa aatagctttc     420
ccccgttgca gcgcatgggt attttttcta gtaaaaataa aagataaact tagactcaaa     480
acatttacaa aaacaacccc taaagttcct aaagcccaaa gtgctatcca cgatccatag     540
caagcccagc ccaacccaac ccaacccaac ccaccccagt ccagccaact ggacaatagt     600
ctccacaccc ccccactatc accgtgagtt gtccgcacgc accgcacgtc tcgcagccaa     660
aaaaaaaaag aaagaaaaaa aagaaaaaga aaaaacagca ggtgggtccg ggtcgtgggg     720
gccggaaacg cgaggaggat cgcgagccag cgacgaggag cttaggcctc atcgttgaag     780
atgcctctgc cgacagtggt cccaaagatg accccaccc cacgaggagc atcgtggaaa     840
aagaagacgt tccaaccacg tcttcaaagc aagtggattg atgtgatatc tccactgacg     900
taagggatga cgcacaatcc cactatcctt cgaggcctca tcgttgaaga tgcctctgcc     960
gacagtggtc ccaaagatgg accccacccc acgaggagc tcgtggaaaa agaagacgtt    1020
ccaaccacgt cttcaaagca agtggattga tgtgatatct ccactgacgt aagggatgac    1080
gcacaatccc actatccttc gaagctccct cctccgcttt ccaaagaaac gcccccatc     1140 gccactatat acatacccc ccctctcctc catcccccc aacccttcta gaaccatctt     1200
ccacacactc aagccacact attggagaac acacagggac aacacaccat aagatccaag    1260
ggaggcctcc gccgccgccg gtaaccaccc gccctctc ctctttcttt ctccgttttt     1320
ttttccgtct cggtctcgat ctttggcctt ggtagtttgg gtgggcgaga ggcggcttcg    1380

```
tgcgcgccca gatcggtgcg cgggaggggc gggatctcgc ggctggggct ctcgccggcg    1440
tggatccggc ccggatctcg cggggaatgg ggctctcgga tgtagatctg cgatccgccg    1500
ttgttggggg agatgatggg gggtttaaaa tttccgccgt gctaaacaag atcaggaaga    1560
ggggaaaagg gcactatggt ttatattttt atatatttct gctgcttcgt caggcttaga    1620
tgtgctagat cttctttct tcttttttgtg ggtagaattt gaatccctca gcattgttca    1680
tcggtagttt ttcttttcat gatttgtgac aaatgcagcc tcgtgcggag ctttttttgta    1740 ggtagaag                                                             1748
```

```
<210> SEQ ID NO 50
<211> LENGTH: 2001
<212> TYPE: DNA
<213> ORGANISM: Artificial
<220> FEATURE:
<223> OTHER INFORMATION: A coding sequence for beta-glucuronidase (GUS)
      with a processable intron derived from the potato light-inducible
      tissue-specific ST-LS1 gene (Genbank Accession: X04753).

<400> SEQUENCE: 50
```

```
atggtccgtc ctgtagaaac cccaacccgt gaaatcaaaa aactcgacgg cctgtgggca    60
ttcagtctgg atcgcgaaaa ctgtggaatt gatcagcgtt ggtgggaaag cgcgttacaa    120
gaaagccggg caattgctgt gccaggcagt tttaacgatc agttcgccga tgcagatatt    180
cgtaattatg cggcaacgt ctggtatcag cgcgaagtct ttataccgaa aggttgggca    240
ggccagcgta tcgtgctgcg tttcgatgcg gtcactcatt acggcaaagt gtgggtcaat    300
aatcaggaag tgatggagca tcagggcggc tatacgccat ttgaagccga tgtcacgccg    360
tatgttattg ccgggaaaag tgtacgtaag tttctgcttc tacctttgat atatatataa    420
taattatcat taattagtag taatataata tttcaaatat tttttttcaaa ataaaagaat    480 gtagtatata gcaattgctt ttctgtagtt tataagtgtg tatattttaa tttataactt    540
ttctaatata tgaccaaaat ttgttgatgt gcaggtatca ccgtttgtgt gaacaacgaa    600
ctgaactggc agactatccc gccgggaatg gtgattaccg acgaaaacgg caagaaaaag    660
cagtcttact tccatgattt ctttaactat gccggaatcc atcgcagcgt aatgctctac    720
accacgccga acacctgggt ggacgatatc accgtggtga cgcatgtcgc gcaagactgt    780
aaccacgcgt ctgttgactg gcaggtggtg gccaatggtg atgtcagcgt tgaactgcgt    840
gatgcggatc aacaggtggt tgcaactgga caaggcacta gcgggacttt gcaagtggtg    900
aatccgcacc tctggcaacc gggtgaaggt tatctctatg aactgtgcgt cacagccaaa    960
agccagacag agtgtgatat ctacccgctt cgcgtcggca tccggtcagt ggcagtgaag    1020
ggcgaacagt tcctgattaa ccacaaaccg ttctactta ctggctttgg tcgtcatgaa    1080
gatgcggact tgcgtggcaa aggattcgat aacgtgctga tggtgcacga ccacgcatta    1140
atggactgga ttggggccaa ctcctaccgt acctcgcatt acccttacgc tgaagagatg    1200
ctcgactggg cagatgaaca tggcatcgtg gtgattgatg aaactgctgc tgtcggcttt    1260
aacctctctt taggcattgg tttcgaagcg ggcaacaagc cgaaagaact gtacagcgaa    1320
gaggcagtca cggggaaac tcagcaagcg cacttacagg cgattaaaga gctgatagcg    1380
cgtgacaaaa accacccaag cgtggtgatg tggagtattg ccaacgaacc ggatacccgt    1440
ccgcaaggtg cacgggaata tttcgcgcca ctggcggaag caacgcgtaa actcgacccg    1500
acgcgtccga tcacctgcgt caatgtaatg ttctgcgacg ctcacaccga taccatcagc    1560
```

-continued

```
gatctctttg atgtgctgtg cctgaaccgt tattacggat ggtatgtcca aagcggcgat      1620
ttggaaacgg cagagaaggt actgaaaaaa gaacttctgg cctggcagga gaaactgcat      1680
cagccgatta tcatcaccga atacggcgtg gatacgttag ccgggctgca ctcaatgtac      1740
accgacatgt ggagtgaaga gtatcagtgt gcatggctgg atatgtatca ccgcgtcttt      1800
gatcgcgtca gcgccgtcgt cggtgaacag gtatggaatt cgccgatttt tgcgacctcg      1860
caaggcatat tgcgcgttgg cggtaacaag aaagggatct tcactcgcga ccgcaaaccg      1920
aagtcggcgg cttttctgct gcaaaaacgc tggactggca tgaacttcgg tgaaaaaccg      1980
cagcagggag gcaaacaatg a                                                2001
```

```
<210> SEQ ID NO 51
<211> LENGTH: 943
<212> TYPE: DNA
<213> ORGANISM: Solanum tuberosum
<220> FEATURE:
<221> NAME/KEY: misc_feature
<222> LOCATION: (1)..(943)
<223> OTHER INFORMATION: DNA sequence of a 3' UTR, T-St.Pis4-1:4:1.

<400> SEQUENCE: 51
```

```
accctgcaat gtgaccctag acttgtccat cttctggatt ggccaactta attaatgtat        60
gaaataaaag gatgcacaca tagtgacatg ctaatcacta taatgtgggc atcaaagttg       120
tgtgttatgt gtaattacta attatctgaa taagagaaag agatcatcca tatttcttat       180
cctaaatgaa tgtcacgtgt ctttataatt ctttgatgaa ccagatgcat tttattaacc       240
aattccatat acatataaat attaatcata tataattaat atcaattggg ttagcaaaac       300
aaatctagtc taggtgtgtt ttgctaatta ttgggggata gtgcaaaaag aaatctacgt       360
tctcaataat tcagatagaa aacttaataa agtgagataa tttacataga ttgctttttat      420 cctttgatat atgtgaaacc atgcatgata taggaaaat agatagagaa ataatttttt         480
acatcgttga atatgtaaac aatttaattc aagaagctag gaatataaat attgaggagt        540
ttatgattat tattattatt ttgatgttca atgaagtttt ttttaatttc atatgaagta        600
tacaaaaatt cttcatagat ttttgtttct atgccgtagt tatctttaat atatttgtgg        660
ttgaagaaat ttattgctag aaacgaatgg attgtcaatt ttttttttaaa gcaaatatat       720 atgaaattat actgtatatt attttagtca tgattaaaat gtggccttaa ttgaatcatc        780
tttctcattc attttttcaa aagcatatca ggatgattga tatttatcta ttttaaaaat       840
taatttaagg gttcaaatta aatttaactt aaaagtgtcc taaccgtagt taaaggttta        900
ctttaaaaaa atactatgaa aaatctaatc ttctatgaat cga                          943
```

```
<210> SEQ ID NO 52
<211> LENGTH: 2181
<212> TYPE: DNA
<213> ORGANISM: Oryza sativa
<220> FEATURE:
<221> NAME/KEY: misc_feature
<222> LOCATION: (1)..(2181)
<223> OTHER INFORMATION: DNA sequence of an EXP, EXP-Os.TubA-3:1
      comprised of a promoter, leader, and intron derived from a Rice
      Tubulin gene.

<400> SEQUENCE: 52
```

```
gacaacaaca tgcttctcat caacatggag ggaagaggga gggagaaagt gtcgcctggt        60
cacctccatt gtcacactag ccactggcca gctctcccac accaccaatg ccaggggcga       120
gctttagcac agccaccgct tcacctccac caccgcacta ccctagcttc gcccaacagc       180
```

```
caccgtcaac gcctcctctc cgtcaacata agagagagag agaagaggag agtagccatg      240
tggggaggag gaatagtaca tggggcctac cgtttggcaa gttattttgg gttgccaagt      300
taggccaata aggggaggga tttggccatc cggttggaaa ggttattggg gtagtatctt      360
tttactagaa ttgtcaaaaa aaaatagttt gagagccatt tggagaggat gttgcctgtt      420
agaggtgctc ttaggacatc aaattccata aaaacatcag aaaaattctc tcgatgaaga      480
tttataacca ctaaaactgc cctcaattcg aagggagttc aaaacaatta aaatcatgtt      540
cgaattgagt ttcaatttca ctttaacccc tttgaaatct caatggtaaa acatcaaccc      600
gtcaggtagc atggttcttt ttattccttt caaaaagagt taattacaaa cagaatcaaa      660
actaacagtt aggcccaagg cccatccgag caaacaatag atcatgggcc aggcctgcca      720
ccaccctccc cctcctggct cccgctcttg aatttcaaaa tccaaaaata tcggcacgac      780
tggccgccga cggagcgggc ggaaaatgac ggaacaaccc ctcgaattct accccaacta      840
cgcccaccaa cccacacgcc actgacaatc cggtcccacc cttgtgggcc cacctacaag      900
cgagacgtca gtcgctcgca gcaaccagtg ggcccacctc ccagtgagcg cgggtagat      960 ctggactctt acccacccac actaaacaaa acggcatgaa tattttgcac taaaaccctc     1020
agaaaaattc cgatattcca aaccagtaca gttcctgacc gttggaggag ccaaagtgga     1080
gcggagtgta aaattgggaa acttaatcga gggggttaaa cgcaaaaacg ccgaggcgcc     1140
tcccgctcta tagaaagggg aggagtggga ggtggaaacc ctaccacacc gcagagaaag     1200
gcgtcttcgt actcgcctct ctccgcgccc tcctccgccg ccgctcgccg ccgttcgtct     1260
ccgccgccac cggctagcca tccaggtaaa acaaacaaaa acggatctga tgcttccatt     1320
cctccgtttc tcgtagtagc gcgcttcgat ctgtgggtgg atctgggtga tcctggggtg     1380
tggttcgttc tgtttgatag atctgtcggt ggatctggcc ttctgtggtt gtcgatgtcc     1440
ggatctgcgt tttgatcagt ggtagttcgt ggatctggcg aaatgttttg gatctggcag     1500
tgagacgcta agaatcggga aatgatgcaa tattaggggg gtttcggatg gggatccact     1560
gaattagtct gtctccctgc tgataatctg ttcctttttg gtagatctgg ttagtgtatg     1620
tttgtttcgg atagatctga tcaatgcttg tttgtttttt caaattttct acctaggttg     1680
tataggaatg gcatgcggat ctggttggat tgccatgatc cgtgctgaaa tgcccctttg     1740
gttgatggat cttgatattt tactgctgtt cacctagatt tgtactcccg tttatactta     1800
atttgttgct tattatgaat agatctgtaa cttaggcaca tgtatggacg gagtatgtgg     1860
atctgtagta tgtacattgc tgcgagctaa gaactatttc agagcaagca cagaaaaaaa     1920
tatttagaca gattgggcaa ctatttgatg gtctttggta tcatgctttg tagtgctcgt     1980
ttctgcgtag taatcttttg atctgatctg aagataggtg ctattatatt cttaaaggtc     2040
attagaacgc tatctgaaag gctgtattat gtggattggt tcacctgtga ctccctgttc     2100
gtcttgtctt gataaatcct gtgataaaaa aaattcttaa ggcgtaattt gttgaaatct     2160
tgttttgtcc tatgcagcct g                                              2181
```

<210> SEQ ID NO 53
<211> LENGTH: 1238
<212> TYPE: DNA
<213> ORGANISM: Arabidopsis thaliana
<220> FEATURE:
<221> NAME/KEY: misc_feature
<222> LOCATION: (1)..(1238)
<223> OTHER INFORMATION: DNA sequence of an EXP, EXP-At.Act7:2 comprised
      of a promoter, leader, and intron derived from the Arabidopsis Actin 7 gene.

<400> SEQUENCE: 53
actagtcaac aattggccaa tctttgttct aaattgctaa taaacgacca tttccgtcaa        60
ttctccttgg ttgcaacagt ctacccgtca aatgtttact aatttataag tgtgaagttt       120
gaattatgaa agacgaaatc gtattaaaaa ttcacaagaa taaacaactc catagatttt       180
caaaaaaaca gtcacgagaa aaaaccaca gtccgtttgt ctgctcttct agttttttatt       240 attttttctat taatagtttt ttgttatttc gagaataaaa tttgaacgat gtccgaacca       300
caaaagccga gccgataaat cctaagccga gcctaacttt agccgtaacc atcagtcacg       360
gctcccgggc taattcattt gaaccgaatc ataatcaacg gtttagatca aactcaaaac       420
aatctaacgg caacatagac gcgtcggtga gctaaaaaga gtgtgaaagc caggtcacca       480
tagcattgtc tctcccagat tttttatttg ggaaataata gaagaaatag aaaaaaataa       540
aagagtgaga aaaatcgtag agctatatat tcgcacatgt actcgtttcg ctttccttag       600
tgttagctgc tgccgctgtt gtttctcctc catttctcta tctttctctc tcgctgcttc       660
tcgaatcttc tgtatcatct tcttcttctt caaggtgagt ctctagatcc gttcgcttga       720
ttttgctgct cgttagtcgt tattgttgat tctctatgcc gatttcgcta gatctgttta       780
gcatgcgttg tggtttttatg agaaaatctt tgttttgggg gttgcttgtt atgtgattcg       840
atccgtgctt gttggatcga tctgagctaa ttcttaaggt ttatgtgtta gatctatgga       900
gtttgaggat tcttctcgct tctgtcgatc tctcgctgtt attttttgttt ttttcagtga       960 agtgaagttg tttagttcga aatgacttcg tgtatgctcg attgatctgg tttttaatctt      1020 cgatctgtta ggtgttgatg tttacaagtg aattctagtg ttttctcgtt gagatctgtg      1080
aagtttgaac ctagttttct caataatcaa catatgaagc gatgtttgag tttcaataaa      1140
cgctgctaat cttcgaaact aagttgtgat ctgattcgtg tttacttcat gagcttatcc      1200
aattcatttc ggtttcattt tactttttttt ttagtgaa                              1238

<210> SEQ ID NO 54
<211> LENGTH: 1020
<212> TYPE: DNA
<213> ORGANISM: Artificial
<220> FEATURE:
<223> OTHER INFORMATION: A coding sequence for a plastid targeted
      GOI-At.ShkG-CTP2+Ec.aadA-SPC/STR:1:1 that confers resistance to
      the antibiotic, spectinomycin.

<400> SEQUENCE: 54
atggcgcaag ttagcagaat ctgcaatggt gtgcagaacc catctcttat ctccaatctc        60
tcgaaatcca gtcaacgcaa atctcccta tcggtttctc tgaagacgca gcagcatcca       120
cgagcttatc cgatttcgtc gtcgtgggga ttgaagaaga gtgggatgac gttaattggc       180
tctgagcttc gtcctcttaa ggtcatgtct tctgtttcca cggcgtgcat gggggaagcg       240
gtgatcgccg aagtatcgac tcaactatca gaggtagttg gcgtcatcga gcgccatctc       300
gaaccgacgt tgctggccgt acatttgtac ggctccgcag tggatggcgg cctgaagcca       360
cacagtgata ttgatttgct ggttacggtg accgtaaggc ttgatgaaac aacgcggcga       420
gctttgatca acgacctttt ggaaacttcg gcttccctg gagagagcga gattctccgc       480
gctgtagaag tcaccattgt tgtgcacgac gacatcattc cgtggcgtta tccagctaag       540
cgcgaactgc aatttggaga atggcagcgc aatgacattc ttgcaggtat cttcgagcca       600
gccacgatcg acattgatct ggctatcttg ctgacaaaag caagagaaca tagcgttgcc       660

```
ttggtaggtc cagcggcgga ggaactcttt gatccggttc ctgaacagga tctatttgag       720
gcgctaaatg aaaccttaac gctatggaac tcgccgcccg actgggctgg cgatgagcga       780
aatgtagtgc ttacgttgtc ccgcatttgg tacagcgcag taaccggcaa aatcgcgccg       840
aaggatgtcg ctgccgactg ggcaatggag cgcctgccgg cccagtatca gcccgtcata       900
cttgaagcta gacaggctta tcttggacaa gaagaagatc gcttggcctc gcgcgcagat       960
cagttggaag aatttgtcca ctacgtgaaa ggcgagatca ccaaggtagt cggcaaataa      1020
```

```
<210> SEQ ID NO 55
<211> LENGTH: 621
<212> TYPE: DNA
<213> ORGANISM: Artificial
<220> FEATURE:
<223> OTHER INFORMATION: DNA sequence of an EXP, EXP-CaMV.35S-enh:1:2
      comprised of an enhanced promoter, and leader.

<400> SEQUENCE: 55
```

```
ggtccgattg agacttttca acaaagggta atatccggaa acctcctcgg attccattgc        60
ccagctatct gtcactttat tgtgaagata gtggaaaagg aaggtggctc ctacaaatgc       120
catcattgcg ataaaggaaa ggccatcgtt gaagatgcct ctgccgacag tggtcccaaa       180
gatggacccc cacccacgag gagcatcgtg aaaaagaag acgttccaac cacgtcttca        240
aagcaagtgg attgatgtga tggtccgatt gagacttttc aacaaagggt aatatccgga       300
aacctcctcg gattccattg cccagctatc tgtcacttta ttgtgaagat agtggaaaag       360
gaaggtggct cctacaaatg ccatcattgc gataaaggaa aggccatcgt tgaagatgcc       420
tctgccgaca gtggtcccaa agatggaccc ccacccacga ggagcatcgt ggaaaaagaa       480
gacgttccaa ccacgtcttc aaagcaagtg gattgatgtg atatctccac tgacgtaagg       540
gatgacgcac aatcccacta tccttcgcaa gacccttcct ctatataagg aagttcattt       600
catttggaga ggacacgctg a                                               621
```

```
<210> SEQ ID NO 56
<211> LENGTH: 715
<212> TYPE: DNA
<213> ORGANISM: Brassica rapa
<220> FEATURE:
<221> NAME/KEY: misc_feature
<222> LOCATION: (1)..(715)
<223> OTHER INFORMATION: DNA sequence of a promoter, P-Br.Snap2-1:1:20.

<400> SEQUENCE: 56
```

```
ctgatacaca cttaagcatc atgtggaaag ccaaagacaa ttggagcgag actcagggtc        60
gtcataatac caatcaaaga cgtaaaacca gacgcaacct ctttggttga atgtaatgaa       120
agggatgtgt cttggtatgt atgtacgaat aacaaaagag aagatggaat tagtagtaga       180
aatatttggg agcttttaa gcccttcaag tgtgcttttt atcttattga tatcatccat        240
ttgcgttgtt taatgcgtct ctagatatgt cctatatctt ttctcagtgt ctgataagtg       300
aaatgtgaga aaaccatacc aaaccaaaat attcaaatct tatttttaat aatgttgaat       360
cactcggagt tgccaccttc tgtgccaatt gtgctgaatc tatcacacta gaaaaaaaca       420
tttcttcaag gtaatgactt gtggactatg ttctgaattc tcattaagtt tttatttttct      480 gaagtttaag ttttttacctt ctgttttgaa atatatcgtt cataagatgt cacgccagga      540
catgagctac acatcgcaca tagcatgcag atcaggacga tttgtcactc acttcaaaca       600
cctaagagct tctctctcac agcgcacaca catatgcatg caatatttac acgtgatcgc       660
```

-continued

```
catgcaaatc tccattctca cctataaatt agagcctcgg cttcactctt tactc          715

<210> SEQ ID NO 57
<211> LENGTH: 171
<212> TYPE: DNA
<213> ORGANISM: Pisum sativum
<220> FEATURE:
<221> NAME/KEY: misc_feature
<222> LOCATION: (1)..(171)
<223> OTHER INFORMATION: DNA sequence encoding a chloroplast transit
      peptide, TS-Ps.RbcS-3C-1:3:1.

<400> SEQUENCE: 57
atggcttcta tgatatcctc ttccgctgtg acaacagtca gccgtgcctc taggggggcaa    60 tccgccgcag tggctccatt cggcgggctc aaatccatga ctggattccc agtgaagaag     120
gtcaacactg acattacttc cattacaagc aatggtggaa gagtaaagtg c            171

<210> SEQ ID NO 58
<211> LENGTH: 930
<212> TYPE: DNA
<213> ORGANISM: Artificial
<220> FEATURE:
<223> OTHER INFORMATION: DNA coding sequence encoding a crtB gene,
      CR-PANag.crtB.nno-1:4:1.

<400> SEQUENCE: 58
atgtcccagc tcctctcct ggatcatgct acccaaacta tggctaacgg tagcaagtcc      60
ttcgctaccg ccgctaagct cttcgatcct gctactaggc gttccgtcct catgctgtac     120
acctggtgta ggcattgcga cgatgtgatc gacgatcaaa cccacggttt cgcgtccgag     180
gctgcggccg aggaagaggc gacccaaagg ctcgctcgcc tccgtaccct caccctcgcc     240
gctttcgagg gcgctgagat gcaagatcct gcgttcgccg ctttccaaga ggtcgccctc     300
acccacggca tcactccaag gatggccctg gaccacctgg acggtttcgc tatggacgtc     360
gcccaaactc gctacgtgac tttcgaggac actctccggt actgctacca tgtcgccggt     420
gttgtcggcc tcatgatggc gcgcgtcatg ggtgtccgcg acgagcgcgt cctcgacagg     480
gcttgcgacc tcggcctcgc gtttcagctt accaacattg ctagggacat catcgacgac     540
gctgcgatag ataggtgtta cctgcctgct gagtggcttc aggacgctgg tcttacgccc     600
gagaactacg ctgccaggga gaacagggct gcccttgcta gagtcgctga gcgtttgatc     660
gacgcggctg aaccctatta cattagctcg caagcgggtt tgcatgactt gcctccacgt     720
tgtgcgtggg ccattgcgac ggcgcgtagt gtttatcgtg aaattgggat caaggttaag     780
gccgctggag gatcagcatg ggaccggaga cagcatacgt ctaagggaga gaagatcgca     840
atgctaatgg cagctcccgg ccaagtcatc cgcgcaaaga caacgcgggt tacacccaga     900
ccagcgggct tatggcagcg accagtatga                                     930

<210> SEQ ID NO 59
<211> LENGTH: 313
<212> TYPE: DNA
<213> ORGANISM: Brassica rapa
<220> FEATURE:
<221> NAME/KEY: misc_feature
<222> LOCATION: (1)..(313)
<223> OTHER INFORMATION: DNA sequence of a 3' UTR, T-Br.Snap2-1:3:6.

<400> SEQUENCE: 59
gagtgtgtat accacggtga tatgagtgtg gttgttgatg tatgttaaca ctacatagtc     60
```

```
atggtgtgtg ttccataaat aatgtactaa tgtaataaga actactccgt agacggtaat        120
aaaagagaag tttttttttt tactcttgct actttcctat aaagtgatga ttaacaacag        180
atacaccaaa aagaaaacaa ttaatctata ttcacaatga agcagtacta gtctattgaa        240
catgtcagat tttcttttt caaatgtcta attaagcctt caaggctagt gatgataaaa         300
gatcatccaa tgg                                                           313
```

```
<210> SEQ ID NO 60
<211> LENGTH: 1179
<212> TYPE: DNA
<213> ORGANISM: Artificial
<220> FEATURE:
<223> OTHER INFORMATION: DNA sequence of an EXP, EXP-Vf.Usp88-enh:1:1
      comprised a chimeric promoter (P-Vf.Usp88-chimera), and leader.

<400> SEQUENCE: 60
```

```
caaatttaca cattgtcact aaacgtctaa atcattgtaa tttgttttg ttttaatatg          60 tgtgttatga acttgatttt caataatttt taaatttggt accagtatta taacatcttt        120
tgtgctaacg gttgccaaca cttagcaatt tgtaagttga ttaattgatt ctaaactttt        180
attgtcttct taattcatgc tgataaatat atgctgataa aaattaaagt gaatatggta        240
ccacaagttt ttggagactg ttgccatata caccaaacat tcaataattc ttgaggataa        300
taatggtacc acacaagctt tgaggtgcat gaacgtcacg tggacaaaag gtttagtaat        360
ttttcaagac aacaatgtta ccacacacaa gttttgaggt gcatgcatgg atgccctgtg        420
gaaagtttaa aaatattttg gaaatgattt gcatggaagc catgtgtaaa accatgacat        480
ccacttggag gaagcaataa tgaagaaaac tacaaattta catgcaacta gttatgcatg        540
tagtcctgca gcaaatttac acattgtcac taaacgtcta atcattgta atttgttttt        600 gttttaatat gtgtgttatg aacttgattt tcaataattt ttaaatttgg taccagtatt        660
ataacatctt ttgtgctaac ggttgccaac acttagcaat ttgtaagttg attaattgat        720
tctaaacttt tattgtcttc ttaattcatg ctgataaata tatgctgata aaaattaaag        780
tgaatatggt accacaagtt tttggagact gttgccatat acaccaaaca ttcaataatt        840
cttgaggata ataatggtac cacacaagct ttgaggtgca tgaacgtcac gtggacaaaa        900
ggtttagtaa ttttttcaaga caacaatgtt accacacaca gttttgagg tgcatgcatg        960 gatgccctgt ggaaagttta aaaatatttt ggaaatgatt tgcatggaag ccatgtgtaa        1020
aaccatgaca tccacttgga ggaagcaata tgaagaaaa ctacaaattt acatgcaact        1080
agttatgcat gtagtctata taatgaggat tttgcaatac tttcattcat aaacactcac        1140
taagttttac acgattatca tttcttcata gccagtcaa                               1179
```

```
<210> SEQ ID NO 61
<211> LENGTH: 1121
<212> TYPE: DNA
<213> ORGANISM: Artificial
<220> FEATURE:
<223> OTHER INFORMATION: DNA sequence of an enhanced, chimeric promoter
      P-Vf.Usp88-chimera comprised of an enhancer derived from the
      Vf.Usp88 promoter operably linked 5' to the Vf.Usp88 promoter.

<400> SEQUENCE: 61
```

```
caaatttaca cattgtcact aaacgtctaa atcattgtaa tttgttttg ttttaatatg          60 tgtgttatga acttgatttt caataatttt taaatttggt accagtatta taacatcttt        120
tgtgctaacg gttgccaaca cttagcaatt tgtaagttga ttaattgatt ctaaactttt        180
```

-continued

```
attgtcttct taattcatgc tgataaatat atgctgataa aaattaaagt gaatatggta        240
ccacaagttt ttggagactg ttgccatata caccaaacat tcaataattc ttgaggataa        300
taatggtacc acacaagctt tgaggtgcat gaacgtcacg tggacaaaag gtttagtaat        360
ttttcaagac aacaatgtta ccacacacaa gttttgaggt gcatgcatgg atgccctgtg        420
gaaagtttaa aaatattttg gaaatgattt gcatggaagc catgtgtaaa accatgacat        480
ccacttggag gaagcaataa tgaagaaaac tacaaattta catgcaacta gttatgcatg        540
tagtccaaat ttacacattg tcactaaacg tctaaatcat tgtaatttgt ttttgtttta        600
atatgtgtgt tatgaacttg attttcaata atttttaaat ttggtaccag tattataaca        660
tcttttgtgc taacggttgc caacacttag caatttgtaa gttgattaat tgattctaaa        720
cttttattgt cttcttaatt catgctgata aatatatgct gataaaaatt aaagtgaata        780
tggtaccaca agtttttgga gactgttgcc atatacacca aacattcaat aattcttgag        840
gataataatg gtaccacaca gctttgagg tgcatgaacg tcacgtggac aaaaggttta        900 gtaattttc aagacaacaa tgttaccaca cacaagtttt gaggtgcatg catggatgcc        960
ctgtggaaag tttaaaaata ttttggaaat gatttgcatg gaagccatgt gtaaaaccat       1020
gacatccact tggaggaagc aataatgaag aaaactacaa atttacatgc aactagttat       1080
gcatgtagtc tatataatga ggattttgca atactttcat t                         1121
```

```
<210> SEQ ID NO 62
<211> LENGTH: 52
<212> TYPE: DNA
<213> ORGANISM: Vicia faba
<220> FEATURE:
<221> NAME/KEY: misc_feature
<222> LOCATION: (1)..(52)
<223> OTHER INFORMATION: DNA sequence of a leader, L-Vf.Usp-1:1:1.

<400> SEQUENCE: 62
cataaacact cactaagttt tacacgatta tcatttcttc atagccagtc aa             52
```

```
<210> SEQ ID NO 63
<211> LENGTH: 1458
<212> TYPE: DNA
<213> ORGANISM: Agrobacterium tumefaciens
<220> FEATURE:
<221> NAME/KEY: misc_feature
<222> LOCATION: (1)..(1458)
<223> OTHER INFORMATION: DNA coding sequence encoding an splA gene,
      CR-AGRtu.splA-C58:1:3.

<400> SEQUENCE: 63
atgcaaaaca aagtgcagtt tatcacctat gttgaccgcc tgaccagagg tggtttcagg        60
caattgaagg aactggtcga tggcaagttc gctggcctgt tcggcggcgt ccatgtcttg       120
cctttcttca atccgatcga tggcgctgat gccggattcg atccaacaga tcacacgatc       180
gtcgatccgc gcctcggcga ctgggaggat gtgcgggctt tgtcgggatc cgtggaaatc       240
atggccgatc ttatcgtcaa ccatgtctca tcgcaatccg gcgcattcac ggacttcatt       300
gccaagggtt cggcgtccga atttgccgac atgttcatga cgttcgataa ggtatttccc       360 gatgcgcca ccgaagaaga ccttctgagg atctatcgac cgcgccccgg tttaccgttt       420
tcgaaggtga ccctggctga tggtactcag cggatgctct ggacaacctt cacaccggag       480
cagatcgaca tcgatgtcca cagcgccaaa ggcacaacct atctcgaaac gatcctcgat       540
cgcttttcgg aggcgaatgt gacggcgatc cgcctcgacg ccgcgggata cgcgatcaag       600
```

```
aaagcgggca gcagttgctt catgatcgac gatacctacg cattcctcga agaagtggct       660
ggaaaggccc gcaaccgcgg catggaggtt ctggtcgaga ttcatagtta tcatcgtgac       720
caaatcgaga tcgcgaagaa ggtcgaccgg gtgtacgatt tcgcactacc accgctcatc       780
ttgcatgcat tgtttacggg agacgccacg ccgctggcaa agtggctggc aataagcccc       840
cgtaacgcga tcaccgttct cgacacccat gacgggattg gcgttataga tgtcggtgcc       900
catagcgacg gacgggcggg cctcctcgaa ccccaggcga tcgacaatct tgtgggagag       960
atccataggc gatcggatgg ccagagccgc caggcgacgg gggccgctgc atcgaatctg      1020
gacctttatc aggtaaactg cacctactat gacgcgcttg gtcgcaacga taatgattat      1080
ctcatcgctc gggcaattca gttttttgct ccaggaattc cgcaagtcta ttatgtcggt      1140
ttattgggcg gcgtaaacga tatggacctg ctcgccaaaa cgggcgtggg gcgtgacatt      1200
aaccggcact attacggcaa cgacgaaatc ggtacggccc ttgagacgcc gctcttccat      1260
cgcctttcaa atctgatccg tttcaggaac acccatcccg ccttcggtgg agcgctcaag      1320
gccaccattg ctgatgccgg agcgttggtg ctttcatggc aacacggcga tgcttttgct      1380
gaattgaaga tctcatttgc cgaccgcaag gcgagcattg ccgcatctgg tcagagcgag      1440
atgcagatcg tcgagtag                                                    1458
```

<210> SEQ ID NO 64
<211> LENGTH: 3105
<212> TYPE: DNA
<213> ORGANISM: Glycine max
<220> FEATURE:
<221> NAME/KEY: misc_feature
<222> LOCATION: (1)..(3105)
<223> OTHER INFORMATION: DNA sequence of an EXP, EXP-Gm.Nmh7:1,
      comprised of a promoter (P-Gm.Nmh7-1:1:12), operably linked 5' to
      a leader (L-Gm.Nmh7:1).

<400> SEQUENCE: 64

```
ggttttaact tatatatcat aataagacac acgcaagtcc gaggaggaag cgaattcgaa        60
caaggaatca tcttgacaac ggtgttagct caatataaag acgaccaagt tcatgaatct       120
tccagttgac caagttccga gataaattat tggttcctat aaattaatta tgtctttgcc       180
taattcgtta attcgaattt agatgaaaat atcttttcgt tcgattcatt tgtcggatca       240
agcaacgatg gggtaggtcc ttagtttata atcaagctag acagatgaaa acagttatag       300
tcttatagcc attgaaaggt cacatattta aaatactatt tgttctaatc acttactgac       360
catctttatt aaacataaaa aaggaagcaa tgcaaatttt tccgataaag aaataaatac       420
ttaattaaat agcacaaaag gtgcatgcta tttgattatt cttgcgaaat gatggacaaa       480
tcacagagca tcatcgtcgg gttaatcctt ctggagtgaa aatacagcca aaaatctaaa       540
caaaatttgg catgtcaaaa tcaaatggat taggtagaga tgtatatgac tttttatgtt       600
ttaattcaaa tgcagatata aaacttgggt ttttctattg ttttcttgga agctagacaa       660
taggagcgac ggacgctcaa actttatctg caatataagt ccaacaaaag caagggaaaa       720
acattaaatg acattgacaa gatatatatt tttcaatatc atcaagagaa taaaataatg       780
ctatatctaa atagcagcgt agaatcataa agttagccat attaacatgc atagaattaa       840
tttgaccata gagagatgta attaaaattt aagatgatcg tcctagaaaa atatcttcgg       900
ctaagataca gatttcactc ttgcacatat aataatttat aaataattta tacaatatta       960 tttttttgtat ttatttatct cttccacatc ttatcattta ttatatttaa aattcaaaat      1020
tttctctttt ttttttctct ttttctctgt tggttgtaca aatatcattt ctcttaaatc      1080
```

-continued

```
aaatatagtt attattgatg cgttgaaata tttaaaatat gtaagattaa aagtgaaaaa    1140
gtgacgtata ttaagtttca taatgtaaaa ttaataataa atacttgaca ttgtatatgc    1200
aagattataa catattttgt gtttctagta caaaataaag taaaaataaa atataattaa    1260
taataatcaa tttaaatatt taaaatgaca tactaatata aattaatttc ctaaaacttt    1320
tgtgattagt catgggtaaa gttaatgagt acatcgcaca ccagtatgat ggttaattaa    1380
ggtaaacaag aaataaaaac taaaaagata attaaggaga gcaaatgaga acttcaaaat    1440
ttgctattaa ggcgtactga aatattcgaa atgacaacac tacaaggcct cgacaacgtt    1500 aactttttc caatttagtg gggctcgaca agctaaagca ttttgatgtt tgaactttaa    1560
attgctcttt cactttcatt taacgcttaa acctagctac gagcaatata acatgggtat    1620
atatagctat atatatcata tgcagatcaa tcttcaatcc caaggttata acattgtgtt    1680
caatgcggag gcagccaaca cggaaactcg cttattatag aaatcacagt tttaaatgga    1740
atgagtgaca gagtttgttt gttttagata ggattggagg cattcaaacg ggaattggac    1800
aggagaaatt cgagggaact tgattatgta attgaaaaaa cttatttcgt ttaaaaatat    1860
tgttttccat aacttcattc ccacgtgaga tggtaaagca ctgaaagtaa attttttttg    1920
acaaattgaa gtaaccattt gatatggttg cggaggagtt acaccaagat agttattagc    1980
attagattaa tgtatttaga aatattttta tatacgtatc aacatcatat aattcaacag    2040
ttggtgttag aaataaaata attcactatt aattttggga ttgatactca atcacttaat    2100
ttcacataac accatcattc atatcataaa aattgacaaa tgttcaatag gtaactttta    2160
tgaactcatg tttgtttatt ttactgaaca ttcattaatc ctttattctt tctcattttc    2220
atttcttctc aaaatttaaa cttttttcaat tcttattttt tattatcatt gaaattattt    2280
agaaactaat tatcattaaa tcaaaaatat ttttatccaa agttattcta ttatcttatg    2340
aattacaatc ttattataat tcaaatgaac atatttatcg aaattataat tataatttat    2400
attaaatatt agacaattct ctattaaatt aaaaactata aatttactta tctaactaaa    2460
aagaactcat aataaaaaat aaatgttata tctcactttt taaatatttta tttgataata    2520 taatcaatta ctgaaaatta tattactatc ttgaaaatat ttttctttcg agaaataaat    2580
ataattttca ccgttaacac actcaattaa tcttctctta tcaattcggt tcattttaaa    2640
ataaagatac catttcatgc tcaaaccaaa gattataata ataaagcaat ttctattaac    2700
ttacaaccaa actatatgta gtatattgaa agtaagtagc agtgtataaa atataaatga    2760
aaatgtaatt aaccatttat tccatgataa acatacgtga tgaaattaga tgtagggaaa    2820
agctgcccta agtgtatgag gcactggtga cttgggggggg aatggtttac gtttccgtga    2880
cggagtagga cggaaagtaa gggtccccac agtgcacatg ggagctggtg ttgacgatga    2940
aactagaaag agcacaagac gtatatgaca aagcgtgcaa tagctttcgc taatttggca    3000
aagaggcctc ccatttgcgg cattgcaatt gcacctcctc tttccctcat taattgaaat    3060
cgctgcccca gatcgtgcaa gtgaagaagc tgctagctat tagct               3105
```

```
<210> SEQ ID NO 65
<211> LENGTH: 2974
<212> TYPE: DNA
<213> ORGANISM: Glycine max
<220> FEATURE:
<221> NAME/KEY: misc_feature
<222> LOCATION: (1)..(2974)
<223> OTHER INFORMATION: DNA sequence of a promoter, P-Gm.Nmh7-1:1:12.
```

```
<400> SEQUENCE: 65
ggttttaact tatatatcat aataagacac acgcaagtcc gaggaggaag cgaattcgaa     60
caaggaatca tcttgacaac ggtgttagct caatataaag acgaccaagt tcatgaatct    120
tccagttgac caagttccga gataaatttat tggttcctat aaattaatta tgtctttgcc    180
taattcgtta attcgaattt agatgaaaat atcttttcgt tcgattcatt tgtcggatca    240
agcaacgatg gggtaggtcc ttagtttata atcaagctag acagatgaaa acagttatag    300
tcttatagcc attgaaaggt cacatattta aaatactatt tgttctaatc acttactgac    360
catctttatt aaacataaaa aaggaagcaa tgcaaatttt tccgataaag aaataaaatac    420 ttaattaaat agcacaaaag gtgcatgcta tttgattatt cttgcgaaat gatggacaaa    480
tcacagagca tcatcgtcgg gttaatcctt ctggagtgaa aatacagcca aaaatctaaa    540
caaaatttgg catgtcaaaa tcaaatggat taggtagaga tgtatatgac ttttttatgtt    600 ttaattcaaa tgcagatata aaacttgggt ttttctattg ttttcttgga agctagacaa    660
taggagcgac ggacgctcaa actttatctg caatataagt ccaacaaaag caagggaaaa    720
acattaaatg acattgacaa gatatatatt tttcaatatc atcaagagaa taaaataatg    780
ctatatctaa atagcagcgt agaatcataa agttagccat attaacatgc atagaattaa    840
tttgaccata gagagatgta attaaaattt aagatgatcg tcctagaaaa atatcttcgg    900
ctaagataca gatttcactc ttgcacatat aataattat aaataattta tacaatatta    960 tttttttgtat ttatttatct cttccacatc ttatcattta ttatatttaa aattcaaaat   1020
tttctctttt ttttttctct ttttctctgt tggttgtaca aatatcattt ctcttaaatc   1080
aaatatagtt attattgatg cgttgaaata tttaaaatat gtaagattaa aagtgaaaaa   1140
gtgacgtata ttaagtttca taatgtaaaa ttaataataa atacttgaca ttgtatatgc   1200
aagattataa catattttgt gtttctagta caaaataaag taaaaataaa atataattaa   1260
taataatcaa tttaaatatt taaaatgaca tactaatata aattaatttc ctaaaacttt   1320
tgtgattagt catgggtaaa gttaatgagt acatcgcaca ccagtatgat ggttaattaa   1380
ggtaaacaag aaataaaaac taaaaagata attaaggaga gcaaatgaga acttcaaaat   1440
ttgctattaa ggcgtactga aatattcgaa atgacaacac tacaaggcct cgacaacgtt   1500
aacttttttc caatttagtg gggctcgaca agctaaagca ttttgatgtt tgaactttaa   1560
attgctcttt cactttcatt taacgcttaa acctagctac gagcaatata acatgggtat   1620
atatagctat atatatcata tgcagatcaa tcttcaatcc caaggttata acattgtgtt   1680
caatgcggag gcagccaaca cggaaactcg cttattatag aaatcacagt tttaaatgga   1740
atgagtgaca gagtttgttt gttttagata ggattggagg cattcaaacg ggaattggac   1800
aggagaaatt cgagggaact tgattatgta attgaaaaaa cttatttcgt ttaaaaatat   1860
tgttttccat aacttcattc ccacgtgaga tggtaaagca ctgaaagtaa attttttttg   1920
acaaattgaa gtaaccattt gatatggttg cggaggagtt acaccaagat agttattagc   1980
attagattaa tgtatttaga aatattttta tatacgtatc aacatcatat aattcaacag   2040
ttggtgttag aaataaaata attcactatt aattttggga ttgatactca atcacttaat   2100
ttcacataac accatcattc atatcataaa aattgacaaa tgttcaatag gtaacttta   2160 tgaactcatg tttgtttatt ttactgaaca ttcattaatc ctttattctt tctcattttc   2220
atttcttctc aaaatttaaa cttttttcaat tcttatttt tattatcatt gaaattattt   2280
agaaactaat tatcattaaa tcaaaaatat ttttatccaa agttattcta ttatcttatg   2340
```

-continued

```
aattacaatc ttattataat tcaaatgaac atatttatcg aaattataat tataatttat     2400
attaaatatt agacaattct ctattaaatt aaaaactata aatttactta tctaactaaa     2460
aagaactcat aataaaaaat aaatgttata tctcactttt taaatatttta tttgataata   2520 taatcaatta ctgaaaatta tattactatc ttgaaaatat ttttctttcg agaaataaat    2580
ataattttca ccgttaacac actcaattaa tcttctctta tcaattcggt tcattttaaa    2640
ataaagatac catttcatgc tcaaaccaaa gattataata ataaagcaat ttctattaac    2700
ttacaaccaa actatatgta gtatattgaa agtaagtagc agtgtataaa atataaatga    2760
aaatgtaatt aaccatttat tccatgataa acatacgtga tgaaattaga tgtagggaaa    2820
agctgcccta agtgtatgag gcactggtga cttgggggggg aatggtttac gtttccgtga   2880
cggagtagga cggaaagtaa gggtccccac agtgcacatg ggagctggtg ttgacgatga    2940
aactagaaag agcacaagac gtatatgaca aagc                                2974
```

```
<210> SEQ ID NO 66
<211> LENGTH: 131
<212> TYPE: DNA
<213> ORGANISM: Glycine max
<220> FEATURE:
<221> NAME/KEY: misc_feature
<222> LOCATION: (1)..(131)
<223> OTHER INFORMATION: DNA sequence of a leader, L-Gm.Nmh7:1.

<400> SEQUENCE: 66
gtgcaatagc tttcgctaat ttggcaaaga ggcctcccat ttgcggcatt gcaattgcac      60
ctcctctttc cctcattaat tgaaatcgct gccccagatc gtgcaagtga agaagctgct     120
agctattagc t                                                         131
```

```
<210> SEQ ID NO 67
<211> LENGTH: 315
<212> TYPE: DNA
<213> ORGANISM: Gossypium barbadense
<220> FEATURE:
<221> NAME/KEY: misc_feature
<222> LOCATION: (1)..(315)
<223> OTHER INFORMATION: DNA sequence of a 3' UTR, T-Gb.E6-3b:1:1.

<400> SEQUENCE: 67
tgatcacctg tcgtacagta tttctacatt tgatgtgtga tttgtgaaga acatcaaaca      60
aaacaagcac tggctttaat atgatgataa gtattatggt aattaattaa ttggcaaaaa    120
caacaatgaa gctaaaattt tatttattga gccttgcggt taatttcttg tgatgatctt    180 ttttttttatt ttctaattat atatagtttc ctttgctttg aaatgctaaa ggtttgagag    240
agttatgctc ttttttttctt cctctttctt ttttaacttt atcatacaaa ttttgaataa    300
aaatgtgagt acatt                                                     315
```

PLANT REGULATORY ELEMENTS AND USES THEREOF FOR AUTOEXCISION

REFERENCE TO RELATED APPLICATION

This application is a 371 National Phase application from International Patent Application No. PCT/2021/055596, filed Oct. 19, 2021, which claims the benefit of United States Provisional Application No. 63/093,893, filed Oct. 20, 2020, each of which is herein incorporated by reference in its entirety.

INCORPORATION OF SEQUENCE LISTING

The sequence listing that is contained in the file named "MONS512WO_ST25.txt", is 111,683 bytes (as measured in Microsoft Windows®), was created on Oct. 18, 2021, and is filed herewith by electronic submission and incorporated by reference herein.

FIELD OF THE INVENTION

The invention relates to the field of plant molecular biology and plant genetic engineering. More specifically, the invention relates to DNA molecules useful for modulating site-specific recombinase gene expression in plants.

BACKGROUND

Regulatory elements are genetic elements that regulate gene activity by modulating the transcription of an operably linked transcribable DNA sequence. Such elements may include promoters, leaders, introns, and 3' untranslated regions and are useful in the field of plant molecular biology and plant genetic engineering.

The use of transgenic technology has provided many beneficial traits for agricultural purposes but has encountered several challenges. One concern is related to the presence of marker genes conferring antibiotic or herbicide resistance in the transgenic crop plants. In addition, there may be other transgene cassettes or DNA sequences that are designed for a particular purpose and present in the initial transformation but are not needed in the final transgenic product. Removal of such marker genes and the other unwanted expression cassettes and DNA sequences is highly desirable in the field of plant biotechnology.

A number of strategies have been designed for the generation of marker-free transgenic plants. For example, removal of the marker gene expression cassette can be done using a two T-DNA transformation system or a site-specific recombinase system.

The two T-DNA transformation system utilizes a binary plant transformation vector that comprises two separate T-DNAs (Two T-DNA transformation system). One T-DNA comprises the marker gene expression cassette. The other T-DNA comprises the expression cassette(s) for the gene(s) of interest that are intended to remain in the transgenic plant. The plant cell can be transformed through *Agrobacterium*-mediated transformation. Each T-DNA can be integrated into separate chromosomes of the transformed plant cell genome. After transformation and plant regeneration, the $R_0$ plants are self-crossed, resulting in $R_1$ progeny. $R_1$ progeny plants are selected that have the T-DNA comprising the expression cassette(s) intended for the final transgenic product but lack the T-DNA comprising the marker gene expression cassette(s) (see, e.g., Komari, T. et al., (1996) Vectors carrying two separate T-DNAs for co-transformation of higher plants mediated by *Agrobacterium tumefaciens* and segregation of transformants free from selection markers, The Plant Journal, 10(1):165-174). The two T-DNA transformation system has some drawbacks with respect to efficiency. In the two T-DNA transformation system, transformant $R_0$ plants can have more than one copy of either or both T-DNAs that may have to be excluded, and the percentage of plants passing selection that possess only one copy of each T-DNA can be low.

Another system to remove marker gene expression cassettes from the transgenic plant relies on excision through use of a site-specific recombinase. A number of site-specific recombinases can be used, such as Cre-recombinase, Flp-recombinase (Lyznik, L. et al., (2000) Gene Transfer Mediated by Site-Specific Recombination Systems, Plant Molecular Biology Manual N1, 1-26), R-recombinase (Machida, C. et al., (2000) Use of the R-RS Site-Specific Recombination System in Plants, Plant Molecular Biology Manual N2, 1-23), or Gin-Recombinase (Maeser, S. et al., (1991). The Gin recombinase of phage Mu can catalyze site-specific recombination in plant protoplasts, Mol Gen Genet, 230: 170-176). Essentially, within the construct, such as a T-DNA insertion, the marker gene expression cassette(s) are flanked by site-specific recombinase recognition sequences, such that the construct sequence between the site-specific recombinase recognition sequences can be excised by expression of the recombinase. Expression cassette(s) that are intended to remain in the transgenic plant after excision are present in the construct outside of the site-specific recombinase recognition sequences of the construct.

Removal of the expression cassettes flanked by the site-specific recombinase recognition sequences can be accomplished using a crossing strategy or through autoexcision. In a crossing strategy, plants (e.g., R1 progeny) preferably homozygous for the presence of the construct are crossed with another line of transgenic plants transformed with an expression cassette used for the expression of the site-specific recombinase. The resulting $F_1$ progeny are then selected for the presence of the construct which has had the expression cassettes flanked by the site-specific recombinase recognition sequences excised. In the case of autoexcision, an additional expression cassette encoding a site-specific recombinase is present in the construct with the other expression cassette(s) to be excised between or flanked by the site-specific recombinase recognition sequences, such that all such expression cassettes are excised by the site-specific recombinase. Often a promoter will have a preference or specificity for driving expression in a specific type of cell or tissue. Not all promoters and expression elements are suitable for efficient autoexcision, and much experimentation is needed to identify the right promoter to drive recombinase expression along with additional expression elements, such as introns and 3' UTRs, that modulate the recombinase expression to achieve the desired excision frequency and outcome.

There is a need for expression elements that drive efficient autoexcision in a crop plant(s). The present disclosure provides several expression elements identified through many years of experimentation that can be used to drive expression of a recombinase and produce efficient autoexcision of the marker and/or recombinase transgenes and possibly other expression cassette(s) in a number of crop species following transformation.

SUMMARY

The invention provides gene regulatory elements for use in plants to drive a site-specific recombinase that will result in efficient autoexcision of marker gene expression cassettes as well as expression cassettes used in genome editing. The invention also provides recombinant DNA molecule constructs comprising the regulatory elements. The present invention also provides constructs comprising the regulatory elements. In one embodiment, the regulatory elements are operably linked to a site-specific recombinase. In certain embodiments the regulatory elements are meiotic promoters. In other embodiments, the regulatory elements are comprised within constructs comprising at least three transgene cassettes. The present invention also provides methods of using the regulatory elements and making and using the recombinant DNA molecules and constructs comprising the regulatory elements.

Thus, in one aspect, the invention provides a recombinant DNA molecule comprising a DNA regulatory sequence selected from the group consisting of: (a) a sequence with at least about 80 percent sequence identity to any of SEQ ID NOs:1-26, 59-62, and 64-66; (b) a sequence comprising any of SEQ ID NOs:1-26, 59-62, and 64-66; and (c) a fragment of (i) any of SEQ ID NOs:1-26, 59-62, and 64-66 or (ii) any sequence with at least 80 percent sequence identity to any of SEQ ID NOs:1-26, 59-62, and 64-66, wherein the fragment has gene-regulatory activity; wherein the sequence is operably linked to a heterologous transcribable DNA sequence encoding a site-specific recombinase. In specific embodiments, the recombinant DNA molecule comprises a DNA regulatory sequence having at least about 80 percent, at least about 81 percent, at least about 82 percent, at least about 83 percent, at least about 84 percent, at least about 85 percent, at least about 86 percent, at least about 87 percent, at least about 88 percent, at least about 89 percent, at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-26, 59-62, and 64-66. In particular embodiments, the DNA regulatory sequence comprises a regulatory element with gene regulatory activity. In some embodiments, the regulatory element comprises a promoter. In still other embodiments, the regulatory element comprises an intron. In still other embodiments, the regulatory element comprises a 3' UTR. In still other embodiments, the DNA regulatory sequence is a germline-preferred promoter. In other embodiments, the germline-preferred promoter is selected from the group consisting of SEQ ID NO:2, SEQ ID NO:5, SEQ ID NO:7, SEQ ID NO:10, SEQ ID NO:13, SEQ ID NO:14, SEQ ID NO:17, SEQ ID NO: 21, and SEQ ID NO:65. In other embodiments, the germline-preferred promoter is a CDC45 promoter. In yet further embodiments, the CDC45 promoter is selected from the group consisting of SEQ ID NO:2, SEQ ID NO:5, and SEQ ID NO:10, and a sequence having at least 80 percent sequence identity to any of SEQ ID NOs: 2, 5, 7, 10, 13, 14, 17, 21 and 65. In still other embodiments, the DNA regulatory sequence is a embryo-preferred promoter. In other embodiments, the DNA regulatory sequence is SEQ ID NO:60 or a sequence with at least 80% sequence identity to SEQ ID NO: 60. In still other embodiments, the heterologous transcribable DNA sequence comprises a gene encoding a site-specific recombinase. In other embodiments, the site-specific recombinase is selected from the group consisting of a Cre-recombinase, an Flp-recombinase, an R-recombinase, and a Gin-recombinase. In yet another embodiment, the site-specific recombinase is a Cre-recombinase.

In another aspect, the recombinant DNA construct further comprises one or both of the following expression cassettes:

a selectable marker transgene; and/or a transgene of agronomic interest. In another embodiment, the recombinant DNA construct further comprises a pair of site-specific recombination site sequences flanking one or both of the transcribable DNA sequences encoding the site-specific recombinase and/or the selectable marker transgene, wherein the site-specific recombination sites can be cleaved by the site-specific recombinase. In further embodiments the selectable marker transgene of the recombinant DNA construct confers resistance to an herbicide or antibiotic. In other embodiments, the site-specific recombination site sequences of the recombinant DNA construct are each selected from the group consisting of LoxP, Lox.TATA-R9, FRT, RS, and GIX. In specific embodiments the site-specific recombination site sequences of the recombinant DNA construct are each a LoxP or Lox.TATA-R9 site. In other embodiments, the site-specific recombination site sequences of the recombinant DNA construct each comprise SEQ ID NO:44 or SEQ ID NO:45.

In another aspect, the transgene of agronomic interest of the recombinant DNA construct confers herbicide tolerance in plants. In some embodiments, the transgene of agronomic interest of the recombinant DNA construct confers pest or disease resistance in plants. In further embodiments, the transgene of agronomic interest of the recombinant DNA construct confers increased yield or stress tolerance in plants. In yet other embodiments, the transgene of agronomic interest of the recombinant DNA construct encodes a dsRNA, a miRNA, or an siRNA.

In another aspect, the recombinant DNA construct further comprises one or both of the following: an expression cassette encoding a guide RNA; and/or an expression cassette encoding a site-specific nuclease. The recombinant DNA construct also comprises site-specific recombination site sequences flanking one or more of the transcribable DNA sequence encoding the site-specific recombinase, the selectable marker transgene, the expression cassette encoding the guide RNA, and/or the expression cassette encoding the site-specific nuclease, wherein the site-specific recombination sites can be cleaved by the site-specific recombinase. In further embodiments the guide RNA comprises a targeting sequence that targets a sequence in the genome of a eukaryotic cell for genome editing or site-specific integration. In another embodiment, the eukaryotic cell is a plant cell. In yet another embodiment, the recombinant DNA construct comprises two or more expression cassettes encoding two or more guide RNAs. In a further embodiment, the recombinant DNA construct comprises two, three, four, five, six, seven, eight, nine, or ten different expression cassettes encoding guide RNAs. In further embodiments, the site-specific nuclease is a RNA-guided endonuclease or CRISPR associated nuclease. In another embodiment, the RNA-guided endonuclease or CRISPR associated nuclease is selected from the group consisting of Cas1, Cas1B, Cas2, Cas3, Cas4, Cas5, Cas6, Cas7, Cas8, Cas9, Cas10, Cpf1, Cys1, Cys2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, and CasY. In specific embodiments, the RNA-guided endonuclease or CRISPR associated nuclease is Cpf1 or Cas9.

In another aspect, provided herein is a DNA molecule or vector comprising the recombinant DNA construct. In another embodiment, a DNA transformation vector comprises the recombinant DNA construct and a T-DNA segment bounded by a left border and a right border. In further embodiments, the transcribable DNA sequence encoding the site-specific recombinase is located between the left border and the right border of the T-DNA segment within the DNA transformation vector. In yet another embodiment, the DNA transformation vector comprises the recombinant DNA construct and a T-DNA segment with left border and a right border, wherein one or more of the transcribable DNA sequence encoding the site-specific recombinase, the selectable marker transgene and/or the transgene of agronomic interest is/are located between the left border and the right border of the T-DNA segment. In further embodiments, the DNA transformation vector comprises the recombinant DNA construct and a T-DNA segment with left border and a right border, wherein one or more of the transcribable DNA sequence encoding the site-specific recombinase, the selectable marker transgene, the transgene of agronomic interest, the expression cassette encoding the guide RNA and/or the expression cassette encoding the site-specific nuclease is/are located between the left border and the right border of the T-DNA segment.

In another aspect, provided herein is a transgenic plant, plants part, or plant cell comprising the recombinant DNA construct. The recombinant DNA construct is stably transformed into the genome of the transgenic plant, plant part or plant cell. The transgenic plant, plant part or plant cell is a corn, soybean, cotton or canola plant, plant part or plant cell. Also provide herein, is a bacterial cell comprising the recombinant DNA construct or the transformation vector.

In another aspect, provided herein is a method for producing a transgenic plant or plant part, comprising (a) transforming a plant cell of an explant with a DNA molecule or vector comprising the recombinant DNA construct to produce one or more transformed plant cells comprising the recombinant DNA construct stably transformed into the genome of the one or more transformed plant cells; (b) regenerating or developing a transgenic plant from the explant, wherein the transgenic plant comprises the recombinant DNA construct stably transformed into the genome of one or more cells of the transgenic plant. In one embodiment, the plant cell is transformed via *Agrobacterium*-mediated transformation or *Rhizobium*-mediated transformation. In another embodiment, the plant cell is transformed via microprojectile-mediated transformation or particle bombardment-mediated transformation. In yet another embodiment, the transgenic plant and plant cell are a corn, soybean, cotton or canola plant and plant cell, respectively. In yet another embodiment, the method further comprises: (c) separating or harvesting a plant part from the transgenic plant.

In another aspect, provided herein is a method for excising an expression cassette from the genome of a transgenic plant, comprising: (a) transforming a plant cell with a DNA molecule or vector comprising the recombinant DNA construct as described herein to produce one or more transformed plant cells comprising the recombinant DNA construct stably transformed into the genome of the one or more transformed plant cells; (b) regenerating or developing a transgenic plant at least in part from the one or more stably transformed plant cells; (c) crossing the transgenic plant to itself or another plant; and (d) selecting one or more progeny plants in which one or both of the transcribable DNA sequence encoding the site-specific recombinase and/or the selectable marker transgene between the pair of site-specific recombination site sequences of the recombinant DNA construct are excised and no longer present in the genome of the progeny plants. In further embodiments of the method, the recombinant DNA construct further comprises one or both of the following expression cassettes between the pair of site-specific recombination site sequences of the recombinant DNA construct: an expression cassette encoding a guide RNA and/or an expression cassette encoding a site-specific nuclease, and wherein one or more progeny plants are selected in which one or more of the transcribable DNA sequence encoding the site-specific recombinase, the selectable marker transgene, the expression cassette encoding the guide RNA, and/or the expression cassette encoding the site-specific nuclease of the recombinant DNA construct are excised and no longer present in the genome of the progeny plants. In specific embodiments, the transgenic plant and plant cell are a corn, soybean, cotton or canola plant and plant cell, respectively. In another embodiment the method further comprises (e) separating or harvesting a plant part from one or more of the progeny plants. In yet another embodiment, the method further comprises (f) crossing one or more of the progeny plants to itself or another plant.

BRIEF DESCRIPTION OF THE SEQUENCES

SEQ ID NO: 1 is a DNA sequence of a regulatory expression element group (EXP), EXP-Zm.Cdc45-1+Zm.DnaK:1:1 comprising a promoter (P-Zm.Cdc45-1:8) operably linked 5' to a leader (L-Zm.Cdc45-1:1), operably linked 5' to an intron (I-Zm.DnaK:1).

SEQ ID NO: 2 is a DNA sequence of a promoter, P-Zm.Cdc45-1:8.

SEQ ID NO: 3 is a DNA sequence of a leader, L-Zm.Cdc45-1:1.

SEQ ID NO: 4 is a DNA sequence of an EXP, EXP-Os.Cdc45-1:1:1 comprising a promoter (P-Os.Cdc45-1-1:1:1), operably linked 5' to a leader (L-Os.Cdc45-1:1:1).

SEQ ID NO: 5 is a DNA sequence of a promoter, P-Os.Cdc45-1-1:1:1.

SEQ ID NO: 6 is a DNA sequence of a leader, L-Zm.Cdc45-1:1.

SEQ ID NO: 7 is a DNA sequence of an EXP, EXP-At.mei1 comprised of a promoter and leader.

SEQ ID NO: 8 is a DNA sequence of a 3' UTR, T-At.mei1-1:2:1.

SEQ ID NO: 9 is a DNA sequence of an EXP, EXP-At.Cdc45:1:1 comprising a promoter (P-At.Cdc45-1:1:1), operably linked 5' to a leader (L-At.Cdc45-1:1:1).

SEQ ID NO: 10 is a DNA sequence of a promoter, P-At.Cdc45-1:1:1:1.

SEQ ID NO: 11 is a DNA sequence of a leader, L-At.Cdc45-1:1:1.

SEQ ID NO: 12 is a DNA sequence of a 3' UTR, T-At.Cdc45:1.

SEQ ID NO: 13 is a DNA sequence of an EXP, EXP-At.Swi1 comprised of a promoter and leader.

SEQ ID NO: 14 is a DNA sequence of an EXP, EXP-At.Swi1a comprised of a promoter and leader.

SEQ ID NO: 15 is a DNA sequence of a 3' UTR, T-At.Swi1-1:2:1.

SEQ ID NO: 16 is DNA sequence of an EXP, EXP-At.Asy1:1:1 comprising a promoter (P-At.Asy1-1:1:1), operably linked 5' to a leader (L-At.Asy1-1:1:1).

SEQ ID NO: 17 is a DNA sequence of a promoter, P-At.Asy1-1:1:1.

SEQ ID NO: 18 is a DNA sequence of a leader, L-At.Asy1-1:1:1.

SEQ ID NO: 19 is a DNA sequence of a 3' UTR, T-At.Asy1-1:1:1.

SEQ ID NO: 20 is a DNA sequence of an EXP, EXP-Gm.Rsp-1:1 comprising a promoter (P-Gm.Rsp-1-1:1:1), operably linked 5' to a leader (L-Gm.Rsp-1-1:1:1).

SEQ ID NO: 21 is a DNA sequence of a promoter, P-Gm.Rsp-1-1:1:1.

SEQ ID NO: 22 is a DNA sequence of a leader, L-Gm.Rsp-1-1:1:1.

SEQ ID NO: 23 is a DNA sequence of a 3' UTR, T-At.Cdc45:3.

SEQ ID NO: 24 is a DNA sequence of a 3' UTR, T-At.Cdc45:4.

SEQ ID NO: 25 is a DNA sequence of an EXP, EXP-Gm.Rsp-1+Gm.Rsp-1+At.AtpE:1 comprising a promoter (P-Gm.Rsp-1-1:1:1), operably linked 5' to a leader (L-Gm.Rsp-1-1:1:1), operably linked 5' to an intron (I-At.AtpE:1).

SEQ ID NO: 26 is a DNA sequence of an intron, I-At.AtpE:1.

SEQ ID NO: 27 is a DNA sequence of an EXP, EXP-Zm.Cdc45-2+Zm.DnaK:1:2 comprising a promoter (P-Zm.Cdc45-2-1:1:3), operably linked 5' to a leader (L-Zm.Cdc45-2-1:1:1), operably linked 5' to an intron (I-Zm.DnaK:1).

SEQ ID NO: 28 is a DNA sequence of a promoter, P-Zm.Cdc45-2-1:1:3.

SEQ ID NO: 29 is a DNA sequence of a leader, L-Zm.Cdc45-2-1:1:1.

SEQ ID NO: 30 is a DNA sequence of an EXP, EXP-Zm.Zm13:2 comprising a promoter (P-Zm.Zm13:2), operably linked 5' to a leader (L-Zm.Zm13:2).

SEQ ID NO: 31 is a DNA sequence of a promoter, P-Zm.Zm13:2.

SEQ ID NO: 32 is a DNA sequence of a leader, L-Zm.Zm13:2.

SEQ ID NO: 33 is a DNA sequence of an EXP, EXP-Zm.Waxy+Zm.DnaK:1:5 comprising a promoter (P-Zm.Waxy-1:1:9), operably linked 5' to a leader (L-Zm.Waxy-1:1:1), operably linked 5' to an intron (I-Zm.DnaK:1).

SEQ ID NO: 34 is a DNA sequence of a promoter, P-Zm.Waxy-1:1:9.

SEQ ID NO: 35 is a DNA sequence of a leader, L-Zm.Waxy-1:1:1.

SEQ ID NO: 36 is a DNA sequence of an EXP, EXP-Syn1 comprised of a promoter and leader.

SEQ ID NO: 37 is a DNA sequence of an EXP, EXP-Syn1a comprised of a promoter and leader.

SEQ ID NO: 38 is a DNA sequence of a 3' UTR, T-At.Syn1-1:2:1.

SEQ ID NO: 39 is a DNA sequence of an intron, I-Zm.DnaK:1.

SEQ ID NO: 40 is a DNA sequence of an EXP, EXP-At.Dmc1+Zm.DnaK:1:1 comprised of a promoter (P-At.Dmc1:1), operably linked 5' to a leader (L-At.Dmc1-1:1:1), operably linked 5' to an intron (I-Zm.DnaK:1).

SEQ ID NO: 41 is a DNA sequence of a promoter, P-At.Dmc1:1.

SEQ ID NO: 42 is a DNA sequence of a leader, L-At.Dmc1-1:1:1.

SEQ ID NO: 43 is a coding sequence for Cre-recombinase (Cre) with a processable intron derived from the potato light-inducible tissue-specific ST-LS1 gene (Genbank Accession: X04753).

SEQ ID NO: 44 is a DNA sequence of a Cre-recombinase site-specific recombination site, RS-P1.lox1:1.

SEQ ID NO: 45 is a DNA sequence of a Cre-recombinase site-specific recombination site, RS-P1.lox.TATA-R9-1:1:1.

SEQ ID NO: 46 is a DNA sequence of an EXP, EXP-Os.Act1:1:1 comprised of a promoter, leader, and intron derived from the Rice Actin 1 gene.

SEQ ID NO: 47 is a coding sequence for a plastid targeted EPSPS, CP4 that confers tolerance to the herbicide, glyphosate.

SEQ ID NO: 48 is a DNA sequence of a 3' UTR, T-AGRtu.nos:13.

SEQ ID NO: 49 a DNA sequence of an EXP, EXP-Os.Act1+CaMV.35S.2×A1-B3+Ta.Lhcb1:1:1 comprised of an enhanced promoter and leader.

SEQ ID NO: 50 is a coding sequence for β-glucuronidase (GUS) with a processable intron derived from the potato light-inducible tissue-specific ST-LS1 gene (Genbank Accession: X04753).

SEQ ID NO: 51 is a DNA sequence of a 3' UTR, T-St.Pis4-1:4:1.

SEQ ID NO: 52 is a DNA sequence of an EXP, EXP-Os.TubA-3:1 comprised of a promoter, leader, and intron derived from a Rice Tubulin gene.

SEQ ID NO: 53 is a DNA sequence of an EXP, EXP-At.Act7:2 comprised of a promoter, leader, and intron derived from the *Arabidopsis* Actin 7 gene.

SEQ ID NO: 54 is a coding sequence for a plastid targeted GOI-At.ShkG-CTP2+Ec.aadA-SPC/STR:1:1 that confers resistance to the antibiotic, spectinomycin.

SEQ ID NO: 55 is a DNA sequence of an EXP, EXP-CaMV.35S-enh:1:2 comprised of an enhanced promoter, and leader.

SEQ ID NO: 56 is a DNA sequence of a promoter, P-Br.Snap2-1:1:20.

SEQ ID NO: 57 is a DNA sequence encoding a chloroplast transit peptide, TS-Ps.RbcS-3C-1:3:1.

SEQ ID NO: 58 is a DNA coding sequence encoding a crtB gene, CR-PANag.crtB.nno-1:4:1.

SEQ ID NO: 59 is a DNA sequence of a 3' UTR, T-Br.Snap2-1:3:6.

SEQ ID NO: 60 is a DNA sequence of an EXP, EXP-Vf.Usp88-enh:1:1 comprised of an enhancer, chimeric promoter (P-Vf.Usp88-chimera), and leader.

SEQ ID NO: 61 is a DNA sequence of a chimeric promoter P-Vf.Usp88-chimera comprised of an enhancer derived from the Vf.Usp88 promoter, operably linked 5' to the Vf.Usp88 promoter.

SEQ ID NO: 62 is a DNA sequence of a leader, L-Vf.Usp-1:1:1.

SEQ ID NO: 63 is a DNA coding sequence encoding an splA gene, CR-AGRtu.sp1A-058:1:3.

SEQ ID NO: 64 is a DNA sequence of an EXP, EXP-Gm.Nmh7:1, comprised of a promoter (P-Gm.Nmh7-1:1:12), operably linked 5' to a leader (L-Gm.Nmh7:1).

SEQ ID NO: 65 is a DNA sequence of a promoter, P-Gm.Nmh7-1:1:12.

SEQ ID NO: 66 is a DNA sequence of a leader, L-Gm.Nmh7:1.

SEQ ID NO: 67 is a DNA sequence of a 3' UTR, T-Gb.E6-3b:1:1.

DETAILED DESCRIPTION

The invention provides gene regulatory elements for use in plants to drive expression of a site-specific recombinase that will result in efficient autoexcision of marker gene expression cassettes. The invention also provides constructs and recombinant DNA molecules comprising the regulatory elements. The invention also provides methods for autoexcising at least two transgene expression cassettes from the genome of a transgenic plant through the use of a construct comprising a transgene cassette wherein the gene regulatory elements described herein are operably linked to a site-specific recombinase gene.

The following definitions are provided for certain terms and phrases used herein. Unless otherwise defined in the present disclosure, terms and phrases used herein are to be understood according to their conventional meaning by those skilled and knowledgeable in the relevant art.

Site-Specific Recombinases and Excision of a DNA Segment

As used herein, a "site-specific recombinase" is an enzyme that binds to specific DNA recognition sequences and catalyzes the cleavage of DNA, DNA strand exchange, and the rejoining of the DNA between two site-specific recombinase site sequences. "Site-specific recombination," or "site-specific recombinase system," or "site-specific recombinase technologies," or "site-directed recombination," or "site-directed recombinase system," or "site-directed recombinase technologies," describes a variety of specialized recombination processes that involve reciprocal exchange between defined DNA sites. As used herein, the term "flanking" refers to two or more sequences, such as site-specific recombination site sequence(s), that are located on either side of one or more specific locus/loci, gene(s), sequence(s), transgene(s), or expression cassette(s). The site-specific recombination site sequences may be cloned within a recombinant DNA construct 5' and 3' relative to a segment of DNA (i.e., flanking the segment of DNA) comprising the expression cassettes under which recombination will occur. Depending on the initial arrangement of the parental site-specific recombination sites, site-specific recombination has one of three possible outcomes: integration (insertion of a foreign DNA segment), excision (removal of a DNA segment), or inversion (rotation of a DNA segment 180 degrees before rejoining the two end fragments). Integration results from recombination between sites on separate DNA molecules (provided that at least one of the parental chromosomes is circular) and occurs with a uniquely defined orientation.

For recombination sites located on the same DNA molecule or chromosome, the outcome can be determined by their relative orientation. While inversion of a DNA segment can result from exchange between inverted (head-to-head) sites, excision can result from recombination between sites in a head-to-tail orientation (Nigel et al. (2006) *Mechanisms of Site-Specific Recombination. Annu. Rev. Biochem,* 75: 567-605). A number of site-specific recombinases can be used for excision of DNA between two site-specific recombinase recognition sites, such as Cre-recombinase which recognizes Lox sites, Flp-recombinase which recognizes FRT sites (see, e.g., Lyznik, L. et al., (2000) Gene Transfer Mediated by Site-Specific Recombination Systems, Plant Molecular Biology Manual N1, 1-26), R-recombinase which recognizes RS sites (see, e.g., Machida, C. et al., (2000) Use of the R-RS Site-Specific Recombination System in Plants, Plant Molecular Biology Manual N2, 1-23), or Gin-Recombinase which recognizes GIX sites (see, e.g., Maeser, S. et al., (1991) The Gin recombinase of phage Mu can catalyze site-specific recombination in plant protoplasts, Mol Gen Genet, 230: 170-176). Each of the above site-specific recombinase systems have been shown to work in plants. The Cre/Lox site-specific recombinase system is the most frequently relied upon system for marker excision in plant biotechnology.

Site-specific recombinases can be used in plant biotechnology to remove marker gene expression cassettes as well as other expression cassettes and DNA segments from a transgenic plant. Typically, a plant is transformed with a recombinant DNA construct or vector that comprises multiple expression cassettes. The expression cassettes can be used to express transgenes that provide favorable characteristics to the plant as well as transgenes used as markers to select for the transformed plant cells such as antibiotic resistant genes, herbicide tolerant genes, or other transgenes useful in the selection process. The transgene cassettes for the marker genes are flanked by a pair of site-specific recombinase recognition sites. After transformation and selection, the regenerated transformed plants are grown. Excision of the marker genes can then be removed through various crossing strategies, either through crossing with a site-specific recombinase expressing line of plants or through autoexcision.

Crossing using a site-specific recombinase expressing line of plants is often carried out as follows. The $R_0$ transformed plants are allowed to self-cross. $R_1$ progeny plants are then selected for the presence of the recombinant DNA construct. The selected $R_1$ progeny plants are then allowed to self-cross, and $R_2$ progeny plants are selected that are homozygous for the recombinant DNA construct insertion. The homozygous $R_2$ progeny plants are then crossed with another line that expresses a recombinase. As a result of this cross, the recombinase excises the marker gene expression cassette(s) that are flanked by the site-specific recombinase recognition sequences, resulting in $F_1$ progeny plants that comprise the desired expression cassette(s) but with the marker gene expression cassette(s) excised out of the genome. The resulting $F_1$ progeny are then allowed to self-cross, and $F_2$ progeny plants are selected that lack the recombinase but are homozygous for the now modified recombinant DNA construct insertion.

Another strategy to remove the marker gene expression cassette(s) is through autoexcision. Similar to the excision approach above, an expressed recombinase is used to excise the marker gene expression cassette(s), but instead of crossing the transformed plants with another line that expresses the recombinase, a recombinase gene expression cassette is located within the same recombinant DNA construct and is flanked by the site-specific recombinase site sequences along with the marker gene expression cassette(s). Expression cassette(s) that are intended to remain in the transgenic plant after autoexcision are present in the recombinant DNA construct outside of the site-specific recombinase site sequences. After transformation and plant regeneration, the $R_0$ plants containing the recombinant DNA construct are generated. Those $R_0$ plants can then be self-crossed, and the resulting $R_1$ progeny plants can be selected for the presence of the altered recombinant DNA construct in which the marker gene expression cassette(s) and recombinase expression cassette have been excised. The advantage of an auto-excision system is that one can remove the marker gene expression cassette(s) in fewer generations than when a site-specific recombinase excision system is used that requires crossing with another line that expresses the site-specific recombinase.

A complicating factor for autoexcision is to find expression elements that provide expression of the site-specific recombinase at the right time in development for autoexcision to produce marker-free $R_1$ progeny plants. One approach is to use expression elements that are active in the germline or embryonic stage of the plant, but not all germline-preferred or embryo-preferred expression elements will provide a successful outcome for autoexcision to efficiently occur. Some germline-preferred or embryo-preferred expression elements may be leaky in their expression, and some may not express the site-specific recombinase at sufficient levels to effectively excise the marker and/or recombinase genes. In addition, germline or embryo expression elements may only provide efficient autoexcision in a particular crop species, such as corn, soybean, or cotton, but not in all three.

DNA Molecules

As used herein, the term "DNA" or "DNA molecule" refers to a double-stranded DNA molecule of genomic or synthetic origin, i.e., a polymer of deoxyribonucleotide bases or a DNA molecule. As used herein, the term "DNA sequence" refers to the nucleotide sequence of a DNA molecule, read from the 5' (upstream) end to the 3' (downstream) end.

As used herein, a "recombinant DNA molecule" or "recombinant DNA construct" is a DNA molecule or construct, respectively, comprising a combination of DNA sequences that would not naturally occur together without human intervention. For instance, a recombinant DNA molecule may comprise at least two DNA sequences heterologous with respect to each other, a DNA sequence that deviates from DNA sequences that exist in nature, a synthetic DNA sequence, and/or a DNA sequence that has been incorporated into a host cell's genomic DNA by genetic transformation, genome editing, or site-specific integration.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated sequence, leader sequence, promoter sequence, transcriptional termination sequence, and the like, that are naturally found within the genome of an organism are not considered to be "isolated" so long as the element is native to the genome of the organism and at the location within the genome in which it is naturally found. However, each of these elements, and subparts of these elements, would be "isolated" within the scope of this disclosure so long as the element is not within its native genome and/or present at a location within the genome where it is naturally found. For the purposes of this disclosure, any transgenic nucleotide sequence, i.e., the nucleotide sequence of the DNA inserted into the genome of cells of a plant or bacterium, or present in an extrachromosomal vector, would be considered to be an isolated nucleotide sequence whether it is present within the plasmid or similar vector used to transform cells, within the genome of the plant or bacterium, or in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment for two sequences is created by aligning the two sequences, e.g., a reference sequence and another sequence, to maximize the number of nucleotide matches in the sequence alignment with appropriate internal nucleotide insertions, deletions, or gaps. As used herein, the term "reference sequence" may refer to a DNA sequence comprising one or more of SEQ ID NOs:1-26, 59-62, and 64-66.

As used herein, the term "percent sequence identity" or "percent identity" or "% identity" is the identity fraction of two optimally aligned sequences multiplied by 100. The "identity fraction" for a sequence optimally aligned with a reference sequence is the number of nucleotide matches in the optimal alignment, divided by the total number of nucleotides in the reference sequence (i.e., the total number of nucleotides in the full length of the entire reference sequence). Thus, some embodiments of the present disclosure provide a DNA molecule comprising a regulatory sequence that, when optimally aligned to a reference sequence, such as one of SEQ ID NOs: 1-26, 59-62, and 64-66, has at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to the reference sequence. According to present embodiments, the regulatory sequence may be operably linked to a transcribable DNA sequence, which may encode a site-specific recombinase.

Regulatory Elements

Regulatory elements, such as promoters, leaders (also known as 5' UTRs), enhancers, introns, and transcription termination regions (or 3' UTRs), play an integral part in the overall expression of genes in living cells. The term "regulatory element," as used herein, refers to a DNA molecule or sequence or segment of DNA having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering. According to embodiments of the present disclosure, a regulatory element is a promoter having a sequence comprising SEQ ID NO: 2, 5, 10, 17, 21, 61 or 65, or a sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to SEQ ID NO: 2, 5, 10, 17, 21, 61 or 65, or a functional fragment or portion of any of the foregoing sequences. According to embodiments of the present disclosure, a regulatory element is a leader having a sequence comprising SEQ ID NO: 3, 6, 11, 18, 22, 61 or 66, or a sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity or 100 percent identity to SEQ ID NO: 3, 6, 11, 18, 22, 61 or 66, or a functional fragment or portion of any of the foregoing sequences that can affect the expression of an operably linked transcribable DNA sequence.

As used herein, a "fragment" of a promoter (or promoter sequence) or regulatory element comprises a fragment or portion of the promoter (or promoter sequence) or regulatory element, respectively, and a "functional fragment" of a promoter (or promoter sequence) or regulatory element comprises a fragment or portion of the promoter (or promoter sequence) or regulatory element, respectively, that affects, modulates or drives the expression of an operably linked transcribable DNA sequence. According to some embodiments, a "functional fragment" of a promoter (or promoter sequence) or regulatory element affects, modulates or drives expression of an operably linked transcribable DNA sequence in a similar manner as the promoter (or promoter sequence) or regulatory element.

As used herein, a "regulatory expression element group" or "EXP" sequence refers to a group of two or more operably linked regulatory elements, such as enhancers, promoters, leaders, and introns. Such two or more operably linked regulatory elements may typically be present together in the same construct and each operably linked to a transcribable DNA sequence. For example, a regulatory expression element group may be comprised, for instance, of a promoter operably linked 5' to a leader sequence. EXP's useful in practicing the present embodiments may comprise SEQ ID NO: 1, 4, 7, 9, 13, 14, 16, 20, 25, 60 or 64, and sequences having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity or 100 percent identity to SEQ ID NO: 1, 4, 7, 9, 13, 14, 16, 20, 25, 60 or 64.

Regulatory elements may be characterized by their associated gene expression pattern in plants, plant tissues and plant cells, e.g., by their positive and/or negative effects on expression, such as constitutive expression or specific patterns of expression, such as temporal, spatial, developmental, tissue, environmental, physiological, pathological or cell cycle expression, and/or chemically responsive or inducible expression, and any combination thereof, as well as by quantitative or qualitative indications or patterns of expression. As used herein, a "gene expression pattern" is any pattern of transcription of an operably linked DNA molecule into a transcribed RNA molecule resulting in relative levels and abundance of the transcribed RNA molecule in various plant tissues and cells during development. Regulatory elements may comprise an enhancer, promoter, leader, 5' UTR, intron, and/or 3' UTR. The regulatory elements of the present disclosure may comprise germline-preferred or embryo-preferred regulatory elements or promoters.

As used herein, the term "promoter" refers generally to a DNA molecule, segment or sequence that is involved in recognition and binding of RNA polymerase II and other proteins, such as trans-acting transcription factors, to initiate or regulate transcription. A promoter may be initially isolated from an upstream or 5' untranslated region (5' UTR) of a genomic copy of a gene. Alternately, promoters may be synthetically produced or engineered DNA molecules. Promoters may also be chimeric. Chimeric promoters are produced through the fusion of two or more heterologous DNA molecules. Promoters useful in practicing the present embodiments may include promoter elements comprising SEQ ID NO: 2, 5, 10, 17, 21, 61 or 65, or a sequence within any of SEQ ID NOs: 1, 4, 7, 9, 13, 14, 16, 20, 25, 60 and 64, or a sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to SEQ ID NOs: 2, 5, 10, 17, 21, 61 or 65, or a sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to a sequence within any of SEQ ID NOs: 1, 4, 7, 9, 13, 14, 16, 20, 25, 60 and 64, or a functional fragment or portion of any of the foregoing sequences. In specific embodiments, DNA molecules and any variants, fragments, portions or derivatives thereof as described herein, are further defined as comprising promoter activity, i.e., are capable of acting as a promoter in a host cell, such as in a transgenic plant. In still further specific embodiments, a fragment of a promoter sequence may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and/or promoter fragments, such as in constructing chimeric promoters, or in combination with other expression or regulatory elements and expression or regulatory element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a promoter, promoter sequence or DNA molecule having promoter activity as disclosed herein.

Recombinant DNA molecules or constructs comprising a promoter or regulatory element derived from any of the promoter elements provided as SEQ ID NOs: 2, 5, 10, 17, 21, 61, and 65, or from any sequence within any of SEQ ID NOs: 1, 4, 7, 9, 13, 14, 16, 20, 25, 60, and 64, such as internal or truncated sequences or sequences with 5' deletions, for example, can be produced using methods known in the art to modify or alter expression, such as by removing element(s) or element portion(s) or non-functional spacer sequence(s), that may have either positive or negative effects on expression; duplicating elements that have positive or negative effects on expression; inserting elements that have positive or negative effects on expression; and/or duplicating or removing elements that have tissue-specific, developmental or cell-specific effects on expression. Any recombinant DNA construct or molecule comprising a promoter or regulatory element derived from any of the promoter elements provided as SEQ ID NO: 2, 5, 10, 17, 21, 61 or 65, or from any sequence within SEQ ID NO: 1, 4, 7, 9, 13, 14, 16, 20, 25, 60 or 64, comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm or developmental timing) effects on expression. Any of the promoter elements provided as SEQ ID NOs: 2, 5, 10, 17, 21, 61 and 65, or comprised within any of SEQ ID NOs: 1, 4, 7, 9, 13, 14, 16, 20, 25, 60 and 64, and fragments or enhancers derived therefrom, can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, a "germline-preferred promoter" is defined as a promoter that drives expression of an operably linked gene (or transgene) predominantly in one or more germline cells of a plant but may also drive expression of the operably linked gene (or transgene) in other cells or tissues of the plant. "Germline" is used as a collective term for those cells that are a gamete cell or progenitor of a gamete cell, differentiate into a gamete cell or progenitor of a gamete cell, or have at least one descendent cell that is a gamete cell or progenitor of a gamete cell. Genetic modifications in germline cells can be passed on to progeny plants through the gametes derived or descended from such germline cells. Use of a germline-preferred promoter to drive expression of a site-specific recombinase allows for the removal of marker and/or recombinase gene(s) flanked by site-specific recombinase recognition sequences in the germline cells in which the site-specific recombinase is expressed. The resulting gametes will possess an altered transgene in which the marker gene expression cassette and/or the recombinase expression cassette are no longer present, and this altered transgene can then be passed on to progeny plants. Through the use of germline-preferred promoters to drive expression of the site-specific recombinase for autoexcision, removal of the marker and/or recombinase gene(s) can be accomplished in the $R_1$ generation from self-crosses or out-crossing of $R_0$ parent plants, as opposed to a later generation when the site-specific recombinase might otherwise be introduced through crossing with a different line having the recombinase expressing construct.

Germline-preferred promoters effective in driving autoexcision in plants differ depending on the crop species in which autoexcision is intended. For example, while the *Arabidopsis* DCM1 promoter has been shown to drive excision of a GUS marker gene in germline cells of *Arabidopsis* (see, e.g., Van Ex et al. (2009) "Evaluation of seven promoters to achieve germline directed Cre-lox recombination in *Arabidopsis thaliana*" Plant Cell Rep. 28: 1509-1520), this promoter did not drive autoexcision in stably transformed soybean plants (see, e.g., Example 4 below). Other *Arabidopsis*-derived germline-preferred promoters can drive autoexcision in transgenic soybean plants, such as promoter sequences comprising SEQ ID NO: 10 or SEQ ID NO: 17, and promoter sequences within SEQ ID NO: 7, SEQ ID NO: 13 or SEQ ID NO: 14 (see, e.g., Example 3). Promoters derived from the germline-preferred CDC45 genes of plants are demonstrated the ability to drive autoexcision in crop plants. The *Arabidopsis* CDC45 promoter SEQ ID NO:10 is shown to drive efficient autoexcision in transgenic soybean (Example 3) and cotton plants (Example 5). The CDC45-1 promoter of *Zea mays* (SEQ ID NO:2) and *Oryza sativa* (SEQ ID NO:5) is shown to drive efficient autoexcision in transgenic corn plants (Example 2). While the soybean Rsp1 promoter (SEQ ID NO:21) is shown to drive autoexcision in soybean plants, the Rsp1 promoter required an intron (I-At.AtpE:1, SEQ ID NO:26) operably linked to the Rsp1 promoter and leader to drive efficient autoexcision in transgenic cotton plants. However, operably linking the I-At.AtpE intron to the Rsp1 promoter and leader failed to drive efficient autoexcision in transgenic soybean. The soybean Rsp1 promoter and P-Gm.Nmh7-1:1:12 (SEQ ID NO:65) is shown to drive autoexcision of four transgene cassettes: the Cre-recombinase; the marker gene, a Cpf1, and guide RNA expression cassettes.

As used herein, an "embryo-preferred promoter" is defined as a promoter that drives expression of an operably linked a gene (or transgene) predominantly in one or more cells of a seed embryo but may also drive expression of the operably linked gene (or transgene) in other cells or tissues of a seed or plant. The embryo-preferred chimeric promoter, P-Vf.Usp88-chimera (SEQ ID NO: 61) is shown to drive autoexcision in transgenic canola plants.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or engineered DNA elements. A leader can be used as a 5' regulatory element for modulating expression of an operably linked transcribable DNA sequence. Leader sequences may be used with a heterologous promoter or with their native promoter. Leaders useful in practicing the present embodiments may include SEQ ID NO: 3, 6, 11, 18, 22, 62 or 66, or a sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to SEQ ID NO: 3, 6, 11, 18, 22, 62 or 66, or a functional fragment or portion of any of the foregoing sequences; or any of the leader elements comprised within any of SEQ ID NOs: 1, 4, 7, 9, 13, 14, 16, 20, 25, 60 and 64, or within any sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to SEQ ID NO: 1, 4, 7, 9, 13, 14, 16, 20, 25, 60 and 64, or functional fragments or portions thereof. In specific embodiments, such DNA sequences may be defined as being able to act as a leader in a host cell, including, for example, a transgenic plant cell. In one embodiment, such sequences are defined as comprising leader activity.

The leader sequences (also referred to as 5' UTRs) presented as SEQ ID NOs:3, 6, 11, 18, 22, 62, and 66; or any of the leader elements comprised within any of SEQ ID NOs:1, 4, 7, 9, 13, 14, 16, 20, 25, 60, and 64 may be comprised of regulatory elements, and/or may adopt secondary structures that can modulate or have an effect on transcription or translation of an operably linked transcribable DNA sequence. The leader sequences presented as SEQ ID NOs: 3, 6, 11, 18, 22, 62, and 66 or any fragment thereof, or any of the leader elements comprised within any of SEQ ID NOs: 1, 4, 7, 9, 13, 14, 16, 20, 25, 60, and 64 or any fragment thereof, can be used in accordance with this disclosure to make chimeric regulatory elements that affect transcription or translation of an operably linked transcribable DNA sequence.

As used herein, the term "intron" refers to a DNA molecule or sequence that may be isolated or identified from a gene and may be defined generally as a region spliced out during messenger RNA (mRNA) processing prior to translation. Alternately, an intron may be a synthetically produced or engineered DNA element. An intron may contain enhancer elements that affect the transcription of operably linked genes or transcribable DNA sequences. An intron may be used as a regulatory element for modulating expression of an operably linked transcribable DNA sequence. A construct may comprise an intron, and the intron may or may not be heterologous with respect to the transcribable DNA sequence. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements. Exemplary introns useful in practicing the present invention are presented as SEQ ID NOs: 26 and 39.

As used herein, the terms "3' transcription termination sequence," "3' untranslated region," or "3' UTR" refer to a DNA sequence that is transcribed into the untranslated region within the 3' portion of an mRNA molecule as generally understood in the art. The 3' untranslated region of an mRNA molecule may be generated by specific cleavage and 3' polyadenylation, also known as formation of a polyA tail. A 3' UTR may be operably linked to and located downstream of a RNA or protein coding portion of a transcribable DNA sequence and may include a polyadenylation signal and other regulatory elements or signals able to affect transcription, mRNA processing, and/or gene expression. PolyA tails are thought to function in mRNA stability and in initiation of translation. Examples of 3' transcription termination molecules in the art are the nopaline synthase 3' region, wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

Regulation of gene function through 3' UTRs is a relatively new field as only recent sequencing technology has provided us with the full landscape of 3' UTRs across species and cell types. Before sequencing technology was available, detailed functional and mechanistic studies were performed only on a few model 3' UTRs. Although these model 3' UTRs have contributed substantially to our understanding of 3' UTR biology, the conclusions drawn about their regulatory functions have been limited and were focused more on mRNA stability. (Mayr, Christine (2017) *Regulation by 3'-Untranslated Regions*. Annual Review of Genetics, 51: 171-194) A genome-wide in silico analysis revealed that motifs in the 3' UTR are primarily conserved on one strand, which is consistent with the 3' UTR acting to regulate gene expression at the post-transcriptional level (Xie, X. et. al., (2005) *Systematic discovery of regulatory motifs in human promoters and 3' UTRs by comparison of several mammals*, Nature 434: 338-345). 3' UTRs determine protein levels through regulation of mRNA stability and translation mediated largely by AU-rich elements and miR-NAs. 3' UTRs also enable local translation through the regulation of mRNA localization. A 3' UTR's length can be regulated by alternative cleavage and polyadenylation. 3' UTRs mediate protein-protein interactions (PPIs) which has widespread consequences for protein complex formation, protein localization, and protein function. 3' UTRs regulate gene expression through the binding of RNA-binding proteins (RBPs). RBPs bind to 3' UTR cis-elements and mediate 3' UTR functions through the recruitment of effector proteins. RBPs cooperate with other bound RBPs to enable functional specificity in vivo. The composition of RBPs bound to a 3' UTR at a given moment is dynamic and can change depending on the local environment, e.g., through addition of posttranslational modifications, local expression of other RBPs, and interactions with membranes and cytoskeletal filaments. RBP binding is also influenced by secondary and tertiary RNA structure formation that regulates accessibility of 3' UTRs (Mayr, Christine (2017) *Regulation by 3'-Untranslated Regions*. Annual Review of Genetics, 51: 171-194).

The poly(A) tail results from the addition of a series of adenosine bases to the 3' end of an RNA molecule. This provides the mRNA with a binding site for a class of regulatory factors called the poly(A) binding proteins (PABP) that have roles in the regulation of gene expression, including mRNA export, stability and decay, and translation. The 5'cap structure of the mRNA and the poly-A tail function synergistically to control mRNA translation. The association of PABPs with the poly(A) tail facilitates an interaction with eIF4F bound to the 5'cap structure, resulting in circularization of the mRNA that promotes translation initiation and ensures ribosome recycling and efficient translation. This interaction also allows inhibition of translation by inhibitor proteins bound to the 3' UTR (Barret, L et. al. (2012) *Regulation of eukaryotic gene expression by the untranslated regions and other non-coding elements*. Cell. Mol. Life Sci. 69:3613-3634).

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one construct, or the neighboring chromosomal DNA into which the construct has inserted. Second, the 3' UTR should not cause a reduction in the transcriptional activity imparted by the promoter, leader, enhancers, and introns that are used to drive expression of the DNA sequence. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. 3' UTRs useful in practicing the present invention are presented as SEQ ID NO:12, 15, 19, 23, 24, and 59.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments for example, the fusion of a promoter to an enhancer element. Thus, the design, construction, and use of chimeric promoters according to the methods disclosed herein for modulating expression of operably linked transcribable DNA molecules are encompassed by the present invention. A chimeric promoter useful in practicing the invention is presented as SEQ ID NO:61.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:1-26, 59-62, and 64-66 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites and/or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, a polynucleotide sequence provided as SEQ ID NOs:1-26, 59-62, and 64-66 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

As used herein, a "transcribable DNA sequence" is any DNA sequence that when operably linked to a promoter can be transcribed into RNA. The transcribed RNA molecule encoded by the transcribable DNA sequence operably linked to the regulatory element(s) provided herein may be translated to produce a protein molecule or may provide an antisense or other functional or regulatory RNA molecule, such as a double-stranded hairpin RNA (dsRNA), a transfer RNA (tRNA), a ribosomal RNA (rRNA), a microRNA (miRNA), a small interfering RNA (siRNA), and the like.

As used herein, the term "protein expression" is any pattern of translation of a transcribed RNA molecule into a protein molecule. Protein expression may be characterized by its temporal, spatial, developmental, or morphological qualities, as well as by its quantitative or qualitative indications or expression patterns.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any DNA molecule or vector, or a segment or portion of a DNA molecule, vector or chromosome, derived from any one or more sources and capable of transfection or genomic integration, comprising at least two DNA sequences linked to each other in a functionally operative manner. For example, a construct may comprise two operably linked sequences, such as a regulatory element or promoter operably linked to a coding sequence or transcribable DNA sequence. A construct may be a recombinant DNA construct. An example of a construct that is a linear, recombinant DNA segment is a T-DNA. As used herein, a "vector" refers to a DNA molecule that may contain or comprise a construct of the present disclosure, such as a plasmid, cosmid, virus, phage, or other linear or circular DNA molecule, and a "DNA transformation vector" mean any DNA molecule or vector comprising a recombinant DNA construct that may be used for the purpose of transformation—i.e., for the introduction of a recombinant DNA molecule or construct into a host cell, such as a plant cell. According to some embodiments, a DNA transformation vector may comprise a T-DNA segment bounded by left and/or right border sequences, which may be used for bacteria-mediated transformation, such as *Rhizobium*-mediated or *Agrobacterium*-mediated transformation. A construct typically includes one or more expression cassettes a gene coding sequence or transcribable DNA sequence operably linked to one or more regulatory sequences, such as a promoter, etc. As used herein, an "expression cassette" refers to a DNA sequence comprising at least a transcribable DNA sequence operably linked to one or more regulatory elements, typically at least a promoter and a 3' UTR.

As used herein, the term "operably linked" refers to a functional relationship between two or more physically joined DNA sequences of a DNA molecule, construct, vector or chromosome comprising a first and second DNA sequence arranged such that the first DNA sequence affects the function or expression of the second DNA sequence. The two DNA sequences may or may not be part of a single contiguous DNA molecule and may or may not be adjacent. For example, a promoter is operably linked to a transcribable DNA sequence if the promoter modulates transcription of the transcribable DNA sequence of interest in a cell. A leader, for example, is operably linked to a transcribable DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti or Ri plasmid isolated from *Agrobacterium* spp. (e.g., *A. tumefaciens* or *A. rhizogenes*) comprising a T-DNA that, along with transfer molecules provided by the *Agrobacterium* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriR1 (See, e.g., Ye et al., Transgenic Research 20(4):773-86, 2011), and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404, however other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower mosaic virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast protein.

Transcribable DNA Sequences

As used herein, the term "transcribable DNA sequence" refers to any DNA sequence capable of being transcribed into an RNA molecule, including, but not limited to, those having protein coding sequences and those producing RNA molecules having sequences useful for gene suppression. The type of DNA sequence can include, but is not limited to, a DNA sequence from the same plant, a DNA sequence from another plant, a DNA sequence from a different organism, or a synthetic DNA sequence, such as a DNA sequence containing an antisense message of a gene, or a DNA sequence encoding an artificial, synthetic, or otherwise modified version of a transgene. Exemplary transcribable DNA sequences for incorporation into constructs of the invention include, e.g., DNA sequences or genes from a species other than the species into which the DNA sequence is incorporated or genes that originate from, or are present in, the same species, but are incorporated into recipient cells by genetic engineering methods rather than classical breeding techniques.

A "transgene" refers to a transcribable DNA sequence heterologous to a host cell at least with respect to its location in the host cell genome and/or a transcribable DNA sequence artificially incorporated into a host cell's genome in the current or any prior generation of the cell.

A regulatory element, such as a promoter of the invention, may be operably linked to a transcribable DNA sequence that is heterologous with respect to the regulatory element. As used herein, the term "heterologous" refers to the combination of two or more DNA sequences when such a combination is not normally found in nature. For example, the two DNA sequences may be derived from different species and/or the two DNA sequences may be derived from different genes, e.g., different genes from the same species or the same genes from different species. A regulatory element is thus heterologous with respect to an operably linked transcribable DNA sequence if such a combination is not normally found in nature, i.e., the transcribable DNA sequence does not naturally occur operably linked to the regulatory element. By "heterologous transcribable DNA sequence," it is meant that the transcribable DNA sequence is heterologous with respect to the polynucleotide sequence to which it is operably linked.

The transcribable DNA sequence may generally be any DNA sequence for which expression of a transcript is desired. Such expression of a transcript may result in translation of the resulting mRNA molecule, and thus protein expression. Alternatively, for example, a transcribable DNA sequence may be designed to ultimately cause decreased expression of a specific gene or protein. In one embodiment, this may be accomplished by using a transcribable DNA sequence that is oriented in the antisense direction. One of ordinary skill in the art is familiar with using such antisense technology. Any gene may be negatively regulated in this manner, and, in one embodiment, a transcribable DNA sequence may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-26, 59-62, and 64-66 or fragment thereof, or a sequence having at least 80 percent identity, at least 85 percent identity, at least 86 percent identity, at least 87 percent identity, at least 88 percent identity, at least 89 percent identity, at least 90 percent identity, at least 91 percent identity, at least 92 percent identity, at least 93 percent identity, at least 94 percent identity, at least 95 percent identity, at least 96 percent identity, at least 97 percent identity, at least 98 percent identity, at least 99 percent identity, or 100 percent identity to any of SEQ ID NOs: 1-26, 59-62, and 64-66 or fragment thereof, operably linked to a heterologous transcribable DNA sequence so as to modulate transcription of the transcribable DNA sequence at a desired level or in a desired pattern when the construct is integrated in the genome of a transgenic plant cell. In one embodiment, the transcribable DNA sequence comprises a protein-coding region of a gene and in another embodiment the transcribable DNA sequence comprises an antisense region of a gene or any other transcribable DNA sequence that causes suppression of a specific target gene(s).

Genes of Agronomic Interest

A transcribable DNA sequence may be a gene of agronomic interest. As used herein, the term "gene of agronomic interest" or "transgene of agronomic interest" refers to a transcribable DNA sequence that, when expressed in a particular plant tissue, cell, or cell type, confers a desirable characteristic or trait. The product of a gene or transgene of agronomic interest may act within a plant to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA sequence that is a gene or transgene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified or increased yield, disease resistance, pathogen resistance, modified plant growth and development, modified starch content, modified oil content, modified fatty acid content, modified protein content, modified fruit ripening, enhanced animal and human nutrition, biopolymer productions, environmental stress tolerance or resistance, pharmaceutical peptides, improved processing qualities, improved flavor, hybrid seed production utility, improved fiber production, and desirable biofuel production.

Non-limiting examples of genes (or transgenes) of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716, 837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426, 447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228, 623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene or transgene of agronomic interest can affect the above mentioned plant characteristics or phenotypes by encoding a RNA molecule that causes a targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA sequence is transcribed into a RNA molecule that is capable of causing gene suppression.

Selectable Markers

Selectable marker transgenes may also be used with the regulatory elements of the invention. As used herein the term "selectable marker transgene" refers to any transcribable DNA sequence whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA sequences encoding β-glucuronidase (GUS), green fluorescent protein (GFP), proteins that confer antibiotic resistance, and proteins that confer herbicide tolerance. Examples of selectable marker transgenes are provided as GOI-At.ShkG-CTP2+AGRtu.aroA-CP4.nat:1 (SEQ ID NOs:47) used for selection of transformed plants cells through glyphosate selection, GOI-At.ShkG-CTP2+Ec.aadA-SPC/STR:1:1 (SEQ ID NO:54) used for selection of transformed plants cells through spectinomycin selection, and GOI-Ec.uidA+St.LS1:3 (SEQ ID NO:50), a GUS reporter gene used in the Examples below in a transgene expression cassette that is intended to remain in the integrated construct after autoexcision to demonstrate retention of the expression cassette and determine zygosity.

Site-Specific Nucleases

As used herein, the term "genome editing" refers to the modification of a genetic sequence at a target site in a DNA molecule or the genome or chromosome of a living organism or cell, such as the genome of a crop plant for agriculture, by deletion, substitution and/or insertion of a DNA sequence at or near the target site, which can be generated using a site-specific nuclease. "Site-specific integration" or "site-directed integration" are terms used to refer to the insertion of a DNA sequence or construct into the genome or chromosome of a living organism or cell at a target site. As used herein, the term "site-specific nuclease" refers to a DNA-cutting nuclease enzyme that creates a double-strand break or nick at or near a specific target site or location of a DNA molecule, chromosome or genome. As used herein, a "target site" for genome editing refers to the location of a polynucleotide sequence within a plant genome that is bound and cleaved by a site-specific nuclease introducing a double stranded break (or single-stranded nick) into the nucleic acid backbone of the polynucleotide sequence and/or its complementary DNA strand. After the break or cut is made, the cell's DNA repair mechanism can recognize and repair the break or nick via non-homologous end-joining (NHEJ) or homology-directed repair and possibly introduce a mutation and/or insertion at the target site as understood in the art.

A site-specific nuclease provided herein may be selected from the group consisting of a zinc-finger nuclease (ZFN), a meganuclease, an RNA-guided endonuclease, such as a CRISPR-associated nuclease, a TALE-endonuclease (TALEN), a recombinase, a transposase, or possibly any other endonuclease. See, e.g., Khandagale, K. et al., "Genome editing for targeted improvement in plants," *Plant Biotechnol Rep* 10: 327-343 (2016); and Gaj, T. et al., "ZFN, TALEN and CRISPR/Cas-based methods for genome engineering," *Trends Biotechnol.* 31(7): 397-405 (2013), the contents and disclosures of which are incorporated herein by reference. An expression cassette provided herein may encode a site-specific nuclease. Such an expression cassette may comprise a transcribable DNA sequence encoding the site-specific nuclease operably linked to a plant expressible promoter. In another aspect, a recombinant DNA construct provided herein may comprise at least one, at least two, at least three, at least four, at least five, at least six, at least seven, at least eight, at least nine, or at least ten expression cassettes encoding one or more site-specific nuclease(s).

According to embodiments of the present disclosure, a recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp 1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease or CRISPR-associated nuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 enzyme. In another aspect, a site-specific nuclease provided herein is selected from the group consisting of a Cas9 or a Cpf1 enzyme.

For RNA-guided endonucleases or CRISPR-associated nuclease, a guide RNA (gRNA) molecule may be required to direct the endonuclease to a target site in a DNA molecule, chromosome or genome of a plant via base-pairing or hybridization to cause a DSB or nick at or near the target site. The gRNA may be transformed or introduced into a plant cell or tissue (perhaps along with a nuclease, or nuclease-encoding DNA construct) as a recombinant DNA construct comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the DNA molecule, chromosome or plant genome. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al., "Target specificity of the CRISPR-Cas9 system," *Quant Biol.* 2(2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the target site. An expression cassette provided herein may encode a guide RNA. Such an expression cassette may comprise a transcribable DNA sequence encoding the guide RNA operably linked to a plant expressible promoter. In another aspect, a recombinant DNA construct provided herein may comprise at least one, at least two, at least three, at least four, at least five, at least six, at least seven, at least eight, at least nine, or at least ten expression cassettes encoding one or more guide RNA(s).

Zinc finger nucleases (ZFNs) are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger a-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. See, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFN s can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein can generate a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs may be introduced as ZFN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SeeI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant. In an aspect, a method and/or composition provided herein comprises one or more, two or more, three or more, four or more, or five or more meganucleases. In another aspect, a meganuclease can generate a targeted cut or break.

Zinc finger nucleases (ZFNs) and TAL effector nucleases (TALENs) are chimeric enzymes that combine a nuclease and a DNA-binding domain. TALENs are a class of sequence-specific nucleases that can be used to make double-stranded breaks at specific target sequences in the genome of a plant or other organism. TALENs are restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN also refers to one or both members of a pair of TALENs that work together to cleave DNA at the same site.

Transcription activator-like effectors (TALEs) can be engineered to bind practically any DNA sequence, such as at or near the genomic locus of a GA oxidase gene in a plant. TALE has a central DNA-binding domain composed of 13-28 repeat monomers of 33-34 amino acids. The amino acids of each monomer are highly conserved, except for hypervariable amino acid residues at positions 12 and 13. The DNA-binding domain of TAL effectors may contain 33-35 amino acid sequence repeats which include a repeat-variable di-residue (RVD) at residues 12 and 13, determining their specificity in DNA binding. Each repeat binds a specific nucleotide which has facilitated the engineering of specific DNA-binding domains by selecting a combination of repeat segments containing the appropriate RVD. The number of repeats of the sequence of the RVD determine the length and sequence of the target sequence that will be recognized (Podevin et al. (2013) Trends in Biotechnology 31(6): 375-383). The two variable amino acids are called repeat-variable diresidues (RVDs). The amino acid pairs of RVDs preferentially recognize certain nucleotide bases, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII MutH and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Comm.* 4: 1762). The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W1 17-122.; Cermak et al., *Nucleic Acids Research* (2011). 39:e82; and tale-nt.cac.cornell.edu/about. In an aspect, a recombinant DNA construct provided herein comprises one or more, two or more, three or more, four or more, or five or more TALENs. In another aspect, a TALEN provided herein is capable of generating a targeted cut or break at a target site.

Zinc finger nucleases (ZFNs) comprise a zinc finger DNA binding domain and a double-break-inducing domain. Recognition site specificity is conferred by the zinc finger domain, which may comprise two, three, or four zinc fingers, for example having a C2H2 structure, although other zinc finger structures are known and have been engineered. Zinc finger domains an be amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease, such as FokI. Additional functionalities can be fused to the zinc-finger binding domain, including transcriptional activator domains, transcriptions repressor domains, and methylases. In some examples, dimerization of nuclease domain is required for cleavage activity. Each zinc finger recognizes three consecutive base pairs in the target DNA. For example, a three-finger domain recognizes a sequence of nine contiguous nucleotides, with a dimerization requirement of the nuclease, two sets of zinc finger triplets are used to bind an eighteen-nucleotide recognition sequence (Gaj et al. (2013) Trends Biotechnology, 31(7): 397-405; and Urnov et al. (2010) Nature Reviews Genetics, 11: 636-646).

Cell Transformation

The invention is also directed to a method of producing transformed cells and plants that comprise one or more regulatory elements operably linked to a transcribable DNA sequence.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into and transforming plant cells. The process generally comprises the steps of selecting a suitable host cell or explant, transforming the cell or explant with a molecule or vector, and obtaining a transformed cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others. According to certain embodiments, methods of transformation include *Agrobacterium* or *Rhizobium* mediated transformation or particle bombardment or microprojectile mediated transformation.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, CA, 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, *Monograph,* 16:249 (1987); Fehr, *Principles of Variety Development, Theory and Technique*, (Vol. 1) and *Crop* Species *Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA sequence can be measured using TaqMan® (Applied Biosystems, Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-26, 59-62, and 64-66. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

EXAMPLES

Example 1

Identification of Regulatory Elements Able to Drive Autoexcision in Crop Plants

This example presents the regulatory elements that have been identified over many years of experimentation that are able to drive efficient autoexcision in transgenic corn, soybean, and cotton.

The regulatory elements with the potential to drive efficient autoexcision in transgenic crop plants were first identified through a combination of literature searches and searches of public and proprietary databases. Seventy soybean, twenty cotton, and one-hundred corn binary transformation vector constructs comprising different regulatory elements and combinations have been assayed for efficient autoexcision using the Cre/Lox recombinase system. From these studies, a small number of regulatory elements were identified that provided efficient autoexcision and are presented in Table 1 below.

TABLE 1

Regulatory elements that provide efficient autoexcision in crop plants.

| Description | SEQ ID NO: | Size (bp) | Description and/or regulatory elements of EXP linked in 5' → 3' direction (SEQ ID NOs): |
|---|---|---|---|
| EXP-Zm.Cdc45-1 + Zm.DnaK:1:1 | 1 | 2810 | EXP: P-Zm.Cdc45-1:8 (SEQ ID NO: 2); L-Zm.Cdc45-1:1 (SEQ ID NO: 3); I-Zm.DnaK:1 (SEQ ID NO: 42) |
| P-Zm.Cdc45-1:8 | 2 | 1887 | Promoter |
| L-Zm.Cdc45-1:1 | 3 | 112 | Leader |
| EXP-Os.Cdc45-1:1:1 | 4 | 1957 | EXP: P-Os.Cdc45-1-1:1:1 (SEQ ID NO: 5); L-Os.Cdc45-1-1:1:1 (SEQ ID NO: 6) |
| P-Os.Cdc45-1-1:1:1 | 5 | 1871 | Promoter |
| L-Os.Cdc45-1-1:1:1 | 6 | 86 | Leader |
| EXP-At.mei1 | 7 | 1434 | Promoter + Leader |
| T-At.mei1-1:2:1 | 8 | 667 | 3' UTR |
| EXP-At.Cdc45:1:1 | 9 | 1030 | EXP: P-At.Cdc45-1:1:1 (SEQ ID NO: 10); L-At.Cdc45-1:1:1 (SEQ ID NO: 11) |
| P-At.Cdc45-1:1:1 | 10 | 737 | Promoter |
| L-At.Cdc45-1:1:1 | 11 | 293 | Leader |
| T-At.Cdc45:1 | 12 | 734 | 3' UTR |
| EXP-At.Swi1 | 13 | 1346 | Promoter + Leader |
| EXP-At.Swi1a | 14 | 1721 | Promoter + Leader |
| T-At.Swi1-1:2:1 | 15 | 709 | 3' UTR |
| EXP-At.Asy1:1:1 | 16 | 1361 | EXP: P-At.Asy1-1:1:1 (SEQ ID NO: 17); L-At. Asy1-1:1:1 (SEQ ID NO: 18) |
| P-At.Asy1-1:1:1 | 17 | 1237 | Promoter |
| L-At.Asy1-1:1:1 | 18 | 124 | Leader |
| T-At.Asy1-1:1:1 | 19 | 505 | 3' UTR |
| EXP-Gm.Rsp-1:1 | 20 | 720 | EXP: P-Gm.Rsp-1-1:1:1 (SEQ ID NO: 21); L-Gm.Rsp-1-1:1:1 (SEQ ID NO: 22) |
| P-Gm.Rsp-1-1:1:1 | 21 | 558 | Promoter |
| L-Gm.Rsp-1-1:1:1 | 22 | 162 | Leader |
| T-At.Cdc45:3 | 23 | 188 | 3' UTR |
| T-At.Cdc45:4 | 24 | 509 | 3' UTR |
| EXP-Gm.Rsp-1 + Gm.Rsp-1 + At.AtpE:1 | 25 | 1474 | EXP: P-Gm.Rsp-1-1:1:1 (SEQ ID NO: 21); L-Gm.Rsp-1-1:1:1 (SEQ ID NO: 22); I-At.AtpE:1 (SEQ ID NO: 26) |
| I-At.AtpE: 1 | 26 | 754 | Intron |
| I-Zm.DnaK:1 | 39 | 804 | Intron |
| EXP-Vf.Usp88-enh:1:1 | 60 | 313 | EXP: P-Vf.Usp88-chimera (SEQ ID NO: 61); L-Vf.Usp-1:1:1 (SEQ ID NO: 62) |
| P-Vf.Usp88-chimera | 61 | 1179 | Chimeric promoter |
| L-Vf.Usp-1:1:1 | 62 | 1121 | Leader |
| T-Br.Snap2-1:3:6 | 59 | 52 | 3' UTR |
| EXP-Gm.Nmh7:1 | 64 | 3105 | EXP: P-Gm.Nmh7-1:1:12 (SEQ ID NO: 65); L-Gm.Nmh7:1 (SEQ ID NO: 66) |
| P-Gm.Nmh7-1:1:12 | 65 | 2974 | Promoter |
| L-Gm.Nmh7:1 | 66 | 131 | Leader |

Example 2

The *Zea mays* and *Oryza sativa* CDC45-1 Promoters Drive Autoexcision in Stably Transformed Corn Plants Corn plants were transformed with recombinant DNA molecules, specifically plant transformation constructs, comprising different regulatory elements driving expression of a Cre-recombinase to assess the ability and efficiency of the Cre-recombinase expressed under the control of the different regulatory elements to drive autoexcision of the Cre-recombinase expression cassette and marker gene expression cassette.

Corn plants were transformed with binary plant transformation constructs comprising three transgene expression cassettes: a selectable marker gene expression cassette and a Cre-recombinase expression cassette, both flanked by two LoxP sites (RS-P1.lox1:1, SEQ ID NO:44), and a third expression cassette located outside of the LoxP sites that expresses a β-glucuronidase (GUS) transgene. The Cre-recombinase expression cassette was used to assay different EXP's to test for their ability to drive efficient autoexcision of the Cre-recombinase expression cassette and marker gene expression cassette located between the LoxP sites. The Cre-recombinase expression cassette was comprised of an EXP to be tested, operably linked 5' to a synthetic coding sequence (e.g., a codon redesigned for expression in a plant cell) encoding a Cre-recombinase (GOI-P1.Cre-St.LS1:1:1, SEQ ID NO:43) containing a processable intron derived from the potato light-inducible tissue-specific ST-LS1 gene (GenBank Accession: X04753), operably linked 5' to a 3' termination or 3' UTR (T-AGRtu.nos:13, SEQ ID NO:48). Each plant transformation construct comprised one of two different marker gene expression cassettes, designated "Marker-1" and "Marker-2." The Marker-1 marker gene expression cassette comprised the constitutive EXP, EXP-Os.Act1:1:1 (SEQ ID NO:46), operably linked 5' to a synthetic coding sequence encoding plastid targeted CP4 coding sequence (GOI-At.ShkG-CTP2+AGRtu.aroA-CP4.nat:1, SEQ ID NO:47) which provides tolerance to the herbicide glyphosate, operably linked 5' to a 3' termination region, T-AGRtu.nos:13 (SEQ ID NO:48). The Marker-2 gene expression cassette comprised the constitutive EXP, EXP-Os.TubA-3:1 (SEQ ID NO:52), operably linked 5' to a synthetic coding sequence encoding plastid targeted CP4 coding sequence (GOI-At.ShkG-CTP2+AGRtu.aroA-CP4.nat:1, SEQ ID NO:47) which provides tolerance to the herbicide glyphosate, operably linked 5' to a 3' termination region, T-AGRtu.nos:13 (SEQ ID NO:48).

The marker gene expression cassette and the Cre-recombinase expression cassette were flanked by two LoxP Cre-recombinase recognition sequences (RS-P1.lox1:1, SEQ ID NO:44) in the same head to tail orientation. Expression of the Cre-recombinase within the transformed plant cell would be expected to result in excision of both cassettes if autoexcision is effective. The GUS expression cassette was cloned outside of the LoxP Cre-recombinase recognition sequences and comprised an EXP comprising a chimeric promoter and leader (EXP-Os.Act1+CaMV.35S.2×A1-B3+ Ta.Lhcb1:1:1, SEQ ID NO:49), operably linked 5' to a synthetic coding sequence encoding β-glucuronidase (GOI-Ec.uidA+St.LS1:3, SEQ ID NO:50) containing a processable intron derived from the potato light-inducible tissue-specific ST-LS1 gene (GenBank Accession: X04753), operably linked 5' to a 3' termination region (T-St.Pis4-1:4:1, SEQ ID NO:51).

Three EXPs derived from corn and rice CDC45 gene homologs were operably linked to a transcribable DNA sequence encoding a Cre recombinase and assayed for their ability to drive autoexcision in stably transformed corn plants. EXP-Zm.Cdc45-1+Zm.DnaK:1:1 (SEQ ID NO:1) comprised a promoter (P-Zm.Cdc45-1:8, SEQ ID NO:2), operably linked 5' to a synthetic leader (L-Zm.Cdc45-1:1, SEQ ID NO:3), operably linked 5' to an intron (I-Zm.DnaK: 1, SEQ ID NO:39). EXP-Os.Cdc45-1:1:1 (SEQ ID NO:4) comprised a promoter (P-Os.Cdc45-1-1:1:1, SEQ ID NO:5), operably linked 5' to a leader (L-Os.Cdc45-1-1:1:1, SEQ ID NO:6). EXP-Zm.Cdc45-2+Zm.DnaK:1:2 (SEQ ID NO:27) comprised a promoter (P-Zm.Cdc45-2-1:1:3, SEQ ID NO:28), operably linked 5' to a leader (L-Zm.Cdc45-2-1:1: 1, SEQ ID NO:29), operably linked 5' to an intron (I-Zm.D-naK:1, SEQ ID NO:39).

Two additional EXPs were also operably linked to a transcribable DNA sequence encoding a Cre recombinase and assayed for their ability to drive autoexcision in stably transformed corn plants. EXP-Zm.Zm13:2 (SEQ ID NO:30), which is derived from a germline-preferred gene expressed in pollen, comprised a promoter (P-Zm.Zm13:2, SEQ ID NO:31), operably linked 5' to a lead (L-Zm.Zm13:2, SEQ ID NO:32). EXP-Zm.Waxy+Zm.DnaK:1:5 (SEQ ID NO:33), which is derived from an endosperm preferred gene, comprised a promoter (P-Zm.Waxy-1:1:9, SEQ ID NO:34), operably linked 5' to a leader (L-Zm.Waxy-1:1:1, SEQ ID NO:35), operably linked 5' an intron (I-Zm.DnaK:1, SEQ ID NO:39).

Corn plant cells were transformed, using the binary plant transformation constructs described above with each of the above EXPs to be tested operably linked to a transcribable DNA sequence encoding a Cre recombinase, by *Agrobacterium*-mediated transformation. Methods for *Agrobacterium*-mediated transformation are well known in the art. The resulting transformed plant cells were regenerated into corn plants under glyphosate selection.

$R_0$ plants with single copy events were selected and allowed to self-pollinate. The resulting $R_1$ seeds were then analyzed for the presence of the Cre, CP4, and GUS transgenes using a TAQMAN® assay. Zygosity of the $R_1$ seeds for the integrated construct was also determined using a TAQMAN® assay of the GUS transgene. Forty-one $R_1$ seeds were assayed per each selected self-cross of an $R_0$ event. Those events that gave rise to at least two $R_1$ seeds that were homozygous for GUS and lacked the Cre and CP4 transgenes were considered to have a successful autoexcision of the Cre and CP4 transgene expression cassettes.

Table 2 below shows the results for each of the EXPs. Data corresponding to the two different CP4 marker transgene cassettes (Marker-1 and Marker-2) are also presented in Table 2. Only one of the CP4 transgene cassettes was used for EXP-Zm.Zm13:2 (Marker-1) and EXP-Zm.Waxy+ Zm.DnaK:1:5 (Marker-2). In Table 2, the column "Percent Event Homozygous/41 Seeds Analyzed" indicates the percentage of events that gave rise to at least two $R_1$ seeds that were homozygous for GUS and lacked the Cre and CP4 transgenes. In parenthesis, the first number indicates the number of $R_0$ events that gave rise to at least two $R_1$ seeds that were homozygous for GUS and lacked the Cre and CP4 transgenes, and the second number indicates the number of $R_0$ events from which forty-one seeds per event were analyzed.

TABLE 2

Percent $R_0$ events that demonstrated effective autoexcision in stably transformed corn plants with the corn and rice CDC45-1 promoters driven autoexcision.

| EXP | SEQ ID NO: | GUS Cassette | Percent Event Homozygous/41 Seeds Analyzed |
|---|---|---|---|
| EXP-Zm.Cdc45-1 + Zm.DnaK:1:1 | 1 | Marker-1 | 63% (7/11) |
| EXP-Zm.Cdc45-1 + Zm.DnaK:1:1 | 1 | Marker-2 | 40% (2/5) |
| EXP-Os.Cdc45-1:1:1 | 4 | Marker-1 | 22% (4/18) |
| EXP-Os.Cdc45-1:1:1 | 4 | Marker-2 | 67% (6/9) |
| EXP-Zm.Cdc45-2 + Zm.DnaK:1:2 | 27 | Marker-1 | 0% (0/2) |
| EXP-Zm.Cdc45-2 + Zm.DnaK:1:2 | 27 | Marker-2 | 0% (0/6) |
| EXP-Zm.Zm13:2 | 30 | Marker-1 | 0% (0/6) |
| EXP-Zm.Waxy + Zm.DnaK:1:5 | 33 | Marker-2 | 0% (0/9) |

As can be seen in Table 2 above, the promoters comprised within EXP-Zm.Cdc45-1+Zm.DnaK:1:1 (P-Zm.Cdc45-1:8, SEQ ID NO:2) and EXP-Os.Cdc45-1:1:1 (P-Os.Cdc45-1-1: 1:1, SEQ ID NO:5) were very effective in driving autoexcision in stably transformed corn plants. The promoters comprised within EXP-Zm.Cdc45-2+Zm.DnaK:1:2 (P-Zm.Cdc45-2-1:1:3, SEQ ID NO:28), EXP-Zm.Zm13:2 (P-Zm.Zm13:2, SEQ ID NO:31), and EXP-Zm.Waxy+ Zm.DnaK:1:5 (P-Zm.Waxy-1:1:9, SEQ ID NO:34) were unable to drive autoexcision in this experiment in stably transformed corn plants.

Example 3

The *Arabidopsis* CDC45 Promoter and Other Germline-Preferred Promoters Drive Autoexcision in Stably Transformed Soybean Plants Soybean plants were transformed with recombinant DNA molecules, specifically plant transformation constructs, comprising different regulatory elements driving expression of a Cre-recombinase to assess the ability and efficiency of the Cre-recombinase expressed under the control of the different regulatory elements to drive autoexcision of the Cre-recombinase expression cassette and marker gene expression cassettes.

Soybean plants were transformed with binary plant transformation constructs comprising four transgene expression cassettes: a marker gene expression cassette (crtB) that produces a screenable color phenotype, a Cre-recombinase expression cassette, and a selectable marker expression cassette for selection of transformed soybean cells (aadA), flanked by two LoxP sites (RS-P1.lox.TATA-R9-1:1:1, SEQ ID NO:45), and a fourth expression cassette located outside of the LoxP sites that expresses a β-glucuronidase (GUS) transgene. The Cre-recombinase expression cassette was used to assay different EXP's to test for their ability to drive efficient autoexcision of the crtB expression cassette, the Cre-recombinase expression cassette, and the marker gene expression cassette, all located between the LoxP sites. The Cre-recombinase expression cassette was comprised of an EXP to be tested, operably linked 5' to a synthetic coding sequence encoding a Cre-recombinase (GOI-P1.Cre-St.LS1:1:1, SEQ ID NO:43) containing a proces sable intron derived from the potato light-inducible tissue-specific ST-LS1 gene (GenBank Accession: X04753), operably linked 5' to a 3' termination region (T-AGRtu.nos:13, SEQ ID NO:48). The color marker gene expression cassette comprised a seed preferred promoter and leader (P-Br.Snap2-1:1:20, SEQ ID NO:56) operably linked 5' to a synthetic coding sequence encoding a chloroplast targeted (TS-Ps.RbcS-3C-1:3:1, SEQ ID NO:57), phytoene synthase (crtB) (CR-PANag.crtB.nno-1:4:1, SEQ ID NO:58), operably linked 5' to a 3' termination region (T-Br.Snap2-1:3:6, SEQ ID NO:59). Expression of the crtB gene in seeds results in an orange pigmented seed and is an indicator of the retention of the transgene cassettes between the LoxP sites as a result of a failure for the cassettes to be excised after autoexcision. The transformation aadA selectable marker cassette comprised of an EXP (EXP-At.Act7:2, SEQ ID NO:53), operably linked 5' to a coding sequence encoding a chloroplast targeted Tn7 adenylyltransferase (GOI-At-.ShkG-CTP2+Ec.aadA-SPC/STR:1:1, SEQ ID NO:54), the same germline-preferred gene and comprise a promoter operably linked to a leader. The 3' UTR, T-At.Swi1-1:2:1 (SEQ ID NO:14) was used in both EXP-At.Swi1 expression cassettes. Likewise, two other EXPs, EXP-Syn1 (SEQ ID NO:36) and EXP-Syn1a (SEQ ID NO:37), are different length variants derived from the same germline-preferred gene and comprise a promoter operably linked to a leader. The 3' UTR, T-At.Syn1-1:2:1 (SEQ ID NO:38) were used in both EXP-At.Syn1 expression cassettes.

Soybean plant cells were transformed, using the binary plant transformation constructs described above with each of the above EXPs to be tested operably linked to a transcribable DNA sequence encoding a Cre recombinase, by *Agrobacterium*-mediated transformation. Methods for *Agrobacterium*-mediated transformation are well known in the art. The resulting transformed plant cells were regenerated into soybean plants under spectinomycin selection.

$R_0$ plants with single copy events were selected and allowed to self-pollinate. The resulting $R_1$ seeds were then analyzed for the presence of the GUS transgene using a TAQMAN® assay. Successful autoexcision of the Cre, aadA, and crtB expression cassettes between the LoxP sites was inferred by the absence of an orange color that would be imparted to the seeds by a retained crtB expression cassette. Table 3 below shows the results for each of the EXP/3' UTR combinations.

TABLE 3

| | | | | | $R_0$ events Producing Marker-Free $R_1$ Seeds | Percent $R_0$ events Producing Marker-Free $R_1$ Seeds |
|---|---|---|---|---|---|---|
| EXP | SEQ ID NO: | 3' UTR | SEQ ID NO: | $R_0$ events | | |
| EXP-At.mei1 | 7 | T-At.mei1-1:2:1 | 8 | 9 | 3 | 33% |
| EXP-At.Cdc45:1:1 | 9 | T-At.Cdc45:1 | 12 | 42 | 35 | 83% |
| EXP-At.Swi1 | 13 | T-At.Swi1-1:2:1 | 15 | 13 | 8 | 62% |
| EXP-At.Swi1a | 14 | T-At.Swi1-1:2:1 | 15 | 14 | 8 | 57% |
| EXP-At.Asy1:1:1 | 16 | T-At.Asy1-1:1:1 | 19 | 14 | 3 | 21% |
| EXP-Syn1 | 36 | T-At.Syn1-1:2:1 | 38 | 12 | 0 | 0% |
| EXP-Syn1a | 37 | T-At.Syn1-1:2:1 | 38 | 12 | 0 | 0% |

Percent $R_0$ events which produced marker-free $R_1$ seeds in stably transformed Soybean plants.

which confers spectinomycin resistance and is used for the selection of transformed plant cells, operably linked 5' to a 3' termination region (T-AGRtu.nos:13, SEQ ID NO:48). The GUS transgene expression cassette comprised an enhanced Cauliflower mosaic virus 35S promoter and leader (EXP-CaMV.35S-enh:1:2, SEQ ID NO:55), operably linked 5' to a synthetic coding sequence encoding β-glucuronidase (GOI-Ec.uidA+St.LS1:3, SEQ ID NO:50) containing a processable intron derived from the potato light-inducible tissue-specific ST-LS1 gene (GenBank Accession: X04753), operably linked 5' to a 3' termination region (T-AGRtu.nos:13, SEQ ID NO:48).

Seven EXPs derived from *Arabidopsis* genes with germline-preferred expression were operably linked to a transcribable DNA sequence encoding a Cre recombinase and assayed for their ability to drive autoexcision in stably transformed soybean plants. See Table 3 below. Each Cre-recombinase expression cassette also comprised the native 3' termination region corresponding to the gene from which the EXP was derived (also presented in Table 3). Two of the EXPs, EXP-At.Swi1 (SEQ ID NO:13) and EXP-At.Swi1s (SEQ ID NO:14), are different length variants derived from As can be seen in Table 3 above, all of the EXPs in this experiment, with the exception of EXP-Syn1 and EXP-Syn1a, were able to drive autoexcision in stably transformed soybean plants. The EXP and 3' UTR combination derived from the *Arabidopsis* CDC45 gene (EXP-At.Cdc45:1:1, SEQ ID NO:9 and T-At.Cdc45:1, SEQ ID NO:12) provided the highest percentage of $R_0$ events producing marker-free $R_1$ Seeds. The two variant EXPs derived from the *Arabidopsis* Swi1 gene (EXP-At.Swi1, SEQ ID NO:13 and EXP-At.Swi1a, SEQ ID NO:14) and the same corresponding 3' UTR (T-At.Swi1-1:2:1, SEQ ID NO:15) also provided a high percentage of $R_0$ events producing marker-free $R_1$ Seeds.

Example 4

The Soybean Rsp-1 Promoter Drives Autoexcision in Stably Transformed Soybean Plants Soybean plants were transformed with constructs, specifically plant binary transformation constructs comprising test regulatory elements driving expression of Cre-recombinase and used to assess the ability and efficiency of autoexcision of the Cre-recombinase expression cassette and marker gene expression cassette.

Soybean plants were transformed with binary plant transformation constructs comprising three transgene expression cassettes; a Cre-recombinase expression cassette, and a selectable marker expression cassette for selection of transformed soybean cells (aadA) flanked by two LoxP sites (RS-P1.lox1:1, SEQ ID NO:44); and a third expression cassette outside of the LoxP sites used for the expression of the β-glucuronidase (GUS) transgene. The Cre-recombinase expression cassette was used to assay different EXP's for their ability to drive efficient autoexcision of the Cre-recombinase expression cassette and marker gene expression cassette. The Cre-recombinase expression cassette was comprised of a test EXP, operably linked 5' to a synthetic coding sequence encoding Cre-recombinase (GOI-P1.Cre-St.LS1:1:1, SEQ ID NO:43) containing a processable intron derived from the potato light-inducible tissue-specific ST-LS1 gene (GenBank Accession: X04753), operably linked 5' to a 3' termination region (T-At.Cdc45:1, SEQ ID NO:12). The transformation selectable marker cassette, aadA, was comprised of an EXP (EXP-At.Act7:2, SEQ ID NO:54), operably linked 5' to a coding sequence encoding a chloroplast targeted Tn7 adenylyltransferase (GOI-At.ShkG-CTP2+Ec.aadA-SPC/STR:1:1, SEQ ID NO:54) which confers spectinomycin resistance and used for the selection of transformed plant cells, operably linked 5' to a 3' termination region (T-AGRtu.nos:13, SEQ ID NO:48). The GUS transgene expression cassette was comprised of an enhanced Cauliflower mosaic virus 35S promoter and leader (EXP-CaMV.35S-enh:1:2, SEQ ID NO:55), operably linked 5' to a synthetic coding sequence encoding β-glucuronidase (GOI-Ec.uidA+St.LS1:3, SEQ ID NO:50) containing a processable intron derived from the potato light-inducible tissue-specific ST-LS1 gene (GenBank Accession: X04753), operably linked 5' to a 3' termination region (T-AGRtu.nos: 13, SEQ ID NO:48).

EXP-Gm.Rsp-1:1 Drives Efficient Autoexcision in Stably Transformed Soybean Plants.

Soybean plants were transformed with a binary construct as described above, wherein the EXP, EXP-Gm.Rsp-1:1 (SEQ ID NO:20) drove expression of the Cre-recombinase transgene. The Cre-recombinase expression cassette was comprised of the EXP, EXP-Gm.Rsp-1:1 (SEQ ID NO:20) comprised of a promoter (P-Gm.Rsp-1-1:1:1, SEQ ID NO:21), operably linked 5' to a leader, (L-Gm.Rsp-1-1:1:1, SEQ ID NO:22), operably linked 5' to a synthetic coding sequence encoding Cre-recombinase, operably linked 5' to a 3' termination region (T-At.Cdc45:1, SEQ ID NO:12).

Soybean plant cells were transformed using the binary plant transformation constructs described above by *Agrobacterium*-mediated transformation, as is well known in the art. The resulting transformed plant cells were induced to form whole soybean plants under spectinomycin selection.

Fifty $R_0$, single copy events were allowed to self-pollinate. The resulting $R_1$ plants were then analyzed for the presence of the Cre, aadA, and GUS transgenes using a TAQMAN® assay. The zygosity of the GUS transgene cassette was also determined using a TAQMAN® assay. The percent GUS positive (GUS+) and marker free (aadA-) $R_1$ progeny for each of the fifty $R_0$ events is presented in Table 4 below.

TABLE 4

Percent GUS positive (GUS+) and marker free (aadA−) $R_1$ progeny in stably transformed soybean plants with EXP-Gm.Rsp-1:1 driven autoexcision

| $R_0$ Event | Total $R_1$ Plants | GUS+/ aadA− | Homozygous GUS/ aadA− | Percent GUS+/ aadA− | Percent Homozygous GUS+/ aadA− |
|---|---|---|---|---|---|
| Event-1 | 46 | 6 | 1 | 13% | 2% |
| Event-2 | 41 | 7 | 0 | 17% | 0% |
| Event-3 | 46 | 7 | 1 | 15% | 2% |
| Event-4 | 39 | 14 | 3 | 36% | 8% |
| Event-5 | 46 | 12 | 2 | 26% | 4% |
| Event-6 | 43 | 12 | 7 | 28% | 16% |
| Event-7 | 46 | 21 | 4 | 46% | 9% |
| Event-8 | 42 | 14 | 4 | 33% | 10% |
| Event-9 | 46 | 4 | 1 | 9% | 2% |
| Event-10 | 43 | 12 | 4 | 28% | 9% |
| Event-11 | 46 | 18 | 6 | 39% | 13% |
| Event-12 | 45 | 18 | 10 | 40% | 22% |
| Event-13 | 46 | 6 | 1 | 13% | 2% |
| Event-14 | 40 | 9 | 3 | 23% | 8% |
| Event-15 | 46 | 26 | 11 | 57% | 24% |
| Event-16 | 41 | 24 | 8 | 59% | 20% |
| Event-17 | 46 | 5 | 4 | 11% | 9% |
| Event-18 | 44 | 21 | 11 | 48% | 25% |
| Event-19 | 46 | 17 | 2 | 37% | 4% |
| Event-20 | 45 | 15 | 11 | 33% | 24% |
| Event-21 | 45 | 22 | 5 | 49% | 11% |
| Event-22 | 43 | 12 | 2 | 28% | 5% |
| Event-23 | 46 | 7 | 3 | 15% | 7% |
| Event-24 | 45 | 13 | 3 | 29% | 7% |
| Event-25 | 46 | 5 | 0 | 11% | 0% |
| Event-26 | 44 | 0 | 0 | 0% | 0% |
| Event-27 | 46 | 15 | 5 | 33% | 11% |
| Event-28 | 44 | 9 | 2 | 20% | 5% |
| Event-29 | 44 | 10 | 1 | 23% | 2% |
| Event-30 | 44 | 16 | 2 | 36% | 5% |
| Event-31 | 46 | 12 | 2 | 26% | 4% |
| Event-32 | 44 | 22 | 4 | 50% | 9% |
| Event-33 | 46 | 22 | 4 | 48% | 9% |
| Event-34 | 44 | 10 | 5 | 23% | 11% |
| Event-35 | 45 | 12 | 2 | 27% | 4% |
| Event-36 | 42 | 9 | 2 | 21% | 5% |
| Event-37 | 46 | 17 | 10 | 37% | 22% |
| Event-38 | 45 | 12 | 1 | 27% | 2% |
| Event-39 | 46 | 19 | 6 | 41% | 13% |
| Event-40 | 43 | 10 | 3 | 23% | 7% |
| Event-41 | 46 | 15 | 9 | 33% | 20% |
| Event-42 | 41 | 17 | 7 | 41% | 17% |
| Event-43 | 46 | 11 | 4 | 24% | 9% |
| Event-44 | 43 | 29 | 15 | 67% | 35% |
| Event-45 | 46 | 8 | 0 | 17% | 0% |
| Event-46 | 45 | 26 | 15 | 58% | 33% |
| Event-47 | 45 | 13 | 6 | 29% | 13% |
| Event-48 | 45 | 19 | 13 | 42% | 29% |
| Event-49 | 46 | 14 | 1 | 30% | 2% |
| Event-50 | 46 | 12 | 2 | 26% | 4% |
| Average | | 13.72 | 4.56 | 30.90% | 10.28% |

As can be seen in Table 4 above, all but one $R_0$ event (Event-26) gave rise to marker free $R_1$ progeny after self-pollination. Some $R_0$ events provided a large percentage of marker free $R_1$ progeny plants, many of which were homozygous for the GUS marker expression cassette, such as Event-12, Event-15, Event-18, Event-20, Event-37, Event-41, Event-44, Event-46, and Event-48. The P-Gm.Rsp-1-1:1:1 promoter (SEQ ID NO:21) comprised within EXP-Gm.Rsp-1:1 (SEQ ID NO:20) provided efficient autoexcision in stably transformed soybean plants.

The germline-preferred Dmc1 promoter does not drive efficient autoexcision in stably transformed soybean plants.

The *Arabidopsis* germline-preferred Dmc1 promoter has been demonstrated to drive efficient autoexcision in transformed *Arabidopsis* plants. In order to see if this promoter was capable of driving autoexcision in stably transformed soybean plants, a binary plant transformation vector as described above was constructed wherein the EXP, EXP-At.Dmc1+Zm.DnaK:1:1 (SEQ ID NO:40) was operably linked 5' to a synthetic coding sequence encoding Cre-recombinase.

Soybean plant cells were transformed using the binary plant transformation constructs described above by *Agrobacterium*-mediated transformation, as is well known in the art. The resulting transformed plant cells were induced to form whole soybean plants under spectinomycin selection.

Selected $R_0$, single copy events were allowed to self-pollinate. The resulting $R_1$ plants were then analyzed for the presence of the Cre, aadA, and the GUS transgenes using a TAQMAN® assay. The zygosity of the GUS transgene cassette was also determined using a TAQMAN® assay. The percent GUS positive (GUS+) and marker free (aadA-) $R_1$ progeny for each of the selected $R_0$ events is presented in Table 5 below.

TABLE 5

Percent GUS positive (GUS+) and marker free (aadA-)
$R_1$ progeny in stably transformed soybean plants with
the Dmc1 promoter driven autoexcision.

| $R_0$ Event | Total $R_1$ Plants | GUS+/ aadA- | Homozygous GUS+/ aadA- | Percent GUS+/ aadA- | Percent Homozygous GUS+/ aadA- |
|---|---|---|---|---|---|
| Event-1 | 44 | 0 | 0 | 0% | 0% |
| Event-2 | 46 | 3 | 0 | 6.52% | 0% |
| Event-3 | 44 | 7 | 1 | 15.90% | 2.27% |
| Event-4 | 45 | 2 | 0 | 4.44% | 0% |
| Event-5 | 45 | 0 | 0 | 0% | 0% |
| Event-6 | 46 | 3 | 0 | 6.52% | 0% |
| Event-7 | 46 | 1 | 0 | 2.17% | 0% |
| Event-8 | 45 | 1 | 0 | 2.22% | 0% |
| Event-9 | 45 | 2 | 0 | 4.44% | 0% |
| Event-10 | 44 | 0 | 0 | 0% | 0% |
| Event-11 | 46 | 0 | 0 | 0% | 0% |
| Event-12 | 46 | 1 | 1 | 2.17% | 2.17% |
| Event-13 | 46 | 0 | 0 | 0% | 0% |
| Event-14 | 45 | 0 | 0 | 0% | 0% |
| Event-15 | 45 | 1 | 0 | 2.22% | 0% |
| Event-16 | 46 | 1 | 1 | 2.17% | 2.17% |
| Event-17 | 46 | 0 | 0 | 0% | 0% |
| Event-18 | 46 | 0 | 0 | 0% | 0% |
| Event-19 | 46 | 2 | 0 | 4.35% | 0% |
| Event-20 | 46 | 0 | 0 | 0% | 0% |

As can be seen in Table 5 above, only a few $R_0$, single copy events provided marker free $R_1$ progeny. Only three events of twenty $R_0$ events gave rise to a homozygous GUS positive, marker-free plant. In comparison to EXP-Gm.Rsp-1:1 (SEQ ID NO:20), $R_0$ events comprising EXP-At.Dmc1+Zm.DnaK:1:1 (SEQ ID NO:40) driving Cre-recombinase did not provide efficient autoexcision in stably transformed plants.

Introduction of a Kozak consensus sequence 3' to EXP-Gm.Rsp-1:1 does not dramatically affect the efficiency of autoexcision in stably transformed soybean plants.

The leader sequence of EXP-Gm.Rsp-1:1 (L-Gm.Rsp-1-1:1:1, SEQ ID NO:22) comprises a small fragment of ninety-three base pairs of the open reading frame (ORF) of the *Glycine max* BURP domain-containing protein 9. The small ORF fragment was in frame with the Cre-recombinase coding sequence and as a result, this fragment did not interfere with efficient autoexcision in the $R_1$ progeny plants. In order to shift the bias of translation initiation to the start codon of the Cre-recombinase coding sequence, a small Kozak consensus sequence (5'-GCAAAA-3), based upon Nakagawa et al., 2007 (Nakagawa et al. (2007) *Diversity of preferred nucleotide sequences around the translation initiation codon in eukaryote genomes. Nucleic Acids Research*, 36(3): 861-871), was operably linked 3' of EXP-Gm.Rsp-1:1 (EXP-Gm.Rsp-1:1+Kozak).

Four binary plant transformation constructs similarly as described above were constructed, each comprising EXP-Gm.Rsp-1:1 (SEQ ID NO:20) operably linked 5' to a synthetic coding sequence encoding Cre-recombinase. One construct also comprised a small Kozak consensus sequence operably linked 3' of EXP-Gm.Rsp-1:1 (EXP-Gm.Rsp-1:1+Kozak). Two other constructs comprised truncated variants of T-At.Cdc45:1 (SEQ ID NO:12), T-At.Cdc45:3 (SEQ ID NO:23) and T-At.Cdc45:4 (SEQ ID NO:24). The GUS expression cassette outside of the LoxP sites was substituted for an expression cassette expressing an herbicide tolerance gene.

Soybean plant cells were transformed using the binary plant transformation constructs described above by *Agrobacterium*-mediated transformation, as is well known in the art. The resulting transformed plant cells were induced to form whole soybean plants under spectinomycin selection.

Selected $R_0$, single copy events were allowed to self-pollinate. The resulting $R_1$ plants were then analyzed for the presence of the Cre, aadA, and the herbicide tolerance transgenes using a TAQMAN® assay. The zygosity of the herbicide tolerance (HT) transgene cassette was also determined using a TAQMAN® assay. The percent homozygous HT positive and marker free $R_1$ progeny for each of the selected $R_0$ events is presented in Table 6 below.

TABLE 6

Percent homozygous HT positive and marker free
$R_1$ progeny in stably transformed soybean plants.

| EXP | SEQ ID NO: | 3' UTR | SEQ ID NO: | Total $R_1$ Single Copy Events Analyzed | Average Percent $R_1$ Homozygous HT/ Marker Free |
|---|---|---|---|---|---|
| EXP-Gm.Rsp-1:1 | 20 | T-At.Cdc45:1 | 12 | 8 | 29% |
| EXP-Gm.Rsp-1:1 + Kozak | 20 | T-At.Cdc45:1 | 12 | 21 | 23% |
| EXP-Gm.Rsp-1:1 | 20 | T-At.Cdc45:3 | 23 | 35 | 12% |
| EXP-Gm.Rsp-1:1 | 20 | T-At.Cdc45:4 | 24 | 15 | 13% |

As can be seen in Table 6 above, introduction of the Kozak consensus sequence 3' of EXP-Gm.Rsp-1:1 had minimal effect on the efficiency of autoexcision in stably transformed soybean plants (23% relative to 29% without the Kozak consensus sequence). The truncation variants of the T-At.Cdc45:1 3' UTR reduced the efficiency of autoexcision. However, with both truncation variants of T-At.Cdc45:1 autoexcision still occurred.

Introduction of an Intron 3' to EXP-Gm.Rsp-1:1 Dramatically Reduced Autoexcision in Stably Transformed Soybean Plants.

Introns are known in the art to improve expression of transgenes. In order to assess the effect of an intron in autoexcision, the intron I-At.AtpE:1 (SEQ ID NO:26) was cloned 3' to EXP-Gm.Rsp-1:1 in a binary plant transformation construct similar to those described above. In addition to the Cre, aadA, and the GUS transgene cassettes, a third transgene cassette was cloned between the LoxP sites which was used to express the sucrose phosphorylase gene; a visual marker. When the splA expression cassette is present in the seed, the seed will appear wrinkled. This visual marker allows for a rapid assessment for the presence of the marker gene cassettes that have not been removed by autoexcision. The expression cassette was comprised of a seed enhanced EXP, EXP-Vf.Usp88-enh:1:1 (SEQ ID NO:60), operably linked 5' to the coding sequence encoding sucrose phosphorylase (CR-AGRtu.splA-058:1:3, SEQ ID NO:61), operably linked 5' to a 3' termination region (T-AGRtu.nos:13, SEQ ID NO:48). Selected $R_0$, single copy events were allowed to self-pollinate. The presence of the GUS transgene cassette and the zygosity of the GUS transgene cassette was determined using a TAQMAN® assay. The absence of the Cre, aadA, and splA expression cassettes was determined by visually examining the $R_1$ progeny seed and looking for the absence of a wrinkled seed phenotype. Those seeds with a wrinkled seed appearance were inferred to still comprise the Cre, aadA, and splA expression cassettes. The percent GUS positive (GUS+) and marker free (aadA-) $R_1$ progeny for each of the selected $R_0$ events is presented in Table 7 below.

TABLE 7

Percent GUS positive (GUS+) and marker free (aadA–) $R_1$ progeny in stably transformed soybean plants with EXP-Gm.Rsp-1:1 and I-At.AtpE:1 driven autoexcision.

| $R_0$ Event | Total $R_1$ Plants | GUS+/ aadA– | Homozygous GUS+/ aadA– | Percent GUS+/ aadA– | Percent Homozygous GUS+/ aadA– |
|---|---|---|---|---|---|
| Event-1 | 42 | 4 | 0 | 9.52% | 0% |
| Event-2 | 42 | 0 | 0 | 0% | 0% |
| Event-3 | 45 | 11 | 1 | 24.44% | 2.22% |
| Event-4 | 44 | 1 | 0 | 2.27% | 0% |
| Event-5 | 44 | 1 | 0 | 2.27% | 0% |
| Event-6 | 44 | 1 | 0 | 2.27% | 0% |
| Event-7 | 45 | 0 | 0 | 0% | 0% |
| Event-8 | 40 | 0 | 0 | 0% | 0% |
| Event-9 | 45 | 6 | 1 | 13.33% | 2.22% |
| Event-10 | 44 | 4 | 0 | 9.09% | 0% |
| Event-11 | 40 | 1 | 0 | 2.50% | 0% |
| Event-12 | 43 | 0 | 0 | 0% | 0% |
| Event-13 | 45 | 0 | 0 | 0% | 0% |
| Event-14 | 40 | 4 | 0 | 10.00% | 0% |
| Event-15 | 39 | 4 | 0 | 10.26% | 0% |

As can be seen in Table 7 above, addition of the intron, I-At.AtpE:1 (SEQ ID NO:26) 3' to EXP-Gm.Rsp-1:1 dramatically reduced the efficiency of autoexcision in stably transformed soybean plants when compared to the results without an intron (see Table 4 above). Few $R_0$ events gave rise to homozygous GUS positive, marker-free events. In contrast, as will be seen in example 5 below, introduction of the I-At.AtpE:1 intron 3' to EXP-Gm.Rsp-1:1 enhanced the ability of EXP-Gm.Rsp-1:1 to efficiently drive autoexcision in cotton plants.

Example 5

The Soybean Rsp-1 Promoter Drives Autoexcision in Stably Transformed Cotton Plants when Operably Linked to the Intron, I-At.AtpE:1

Cotton plants were transformed with the same binary plant transformation construct comprising the intron I-At.AtpE:1 (SEQ ID NO:26) cloned 3' to EXP-Gm.Rsp-1:1 as described in the previous example. Selected $R_0$, single copy events were allowed to self-pollinate. The presence of the GUS transgene cassette and the zygosity of the GUS transgene cassette was determined using a TAQMAN® assay. The absence of the Cre, aadA, and splA expression cassettes was determined by visually examining the $R_1$ progeny seed and looking for the absence of a wrinkled seed phenotype. The percent GUS positive (GUS+) and marker free (aadA-) $R_1$ progeny for each of the selected $R_0$ events is presented in Table 8 below.

TABLE 8

Percent GUS positive (GUS+) and marker free (aadA–) $R_1$ progeny in stably transformed cotton plants with EXP-Gm.Rsp-1:1 and I-At.AtpE:1 driven autoexcision.

| $R_0$ Event | Total $R_1$ Plants | GUS+/ aadA– | Homozygous GUS/ aadA– | Percent GUS+/ aadA– | Percent Homozygous GUS+/ aadA– |
|---|---|---|---|---|---|
| Event-1 | 50 | 29 | 2 | 58.00% | 4.00% |
| Event-2 | 50 | 20 | 7 | 40.00% | 14.00% |
| Event-3 | 50 | 0 | 0 | 0.00% | 0.00% |
| Event-4 | 50 | 30 | 8 | 60.00% | 16.00% |
| Event-5 | 50 | 20 | 11 | 40.00% | 22.00% |
| Event-6 | 50 | 0 | 0 | 0.00% | 0.00% |
| Event-7 | 50 | 33 | 6 | 66.00% | 12.00% |
| Event-8 | 50 | 34 | 6 | 68.00% | 12.00% |
| Event-9 | 50 | 28 | 9 | 56.00% | 18.00% |
| Event-10 | 50 | 29 | 6 | 58.00% | 12.00% |
| Event-11 | 50 | 33 | 5 | 66.00% | 10.00% |
| Event-12 | 50 | 32 | 11 | 64.00% | 22.00% |
| Event-13 | 50 | 37 | 8 | 74.00% | 16.00% |
| Event-14 | 50 | 31 | 12 | 62.00% | 24.00% |
| Event-15 | 50 | 36 | 9 | 72.00% | 18.00% |

As can be seen in Table 8 above, and in contrast with the results obtained using the same binary plant transformation construct in soybean, cloning the I-At.AtpE:1 (SEQ ID NO:26) intron 3' to EXP-Gm.Rsp-1:1 resulted in efficient autoexcision in stably transformed cotton plants. All but one event (Event-3) provided marker-free $R_1$ progeny seed and homozygous GUS positive, marker-free negative $R_1$ progeny seed.

Example 6

The *Arabidopsis* CDC45 Promoter Drives Autoexcision in Stably Transformed Cotton Plants Cotton plants were transformed with a construct, specifically a plant binary transformation construct comprising the EXP, EXP-At.Cdc45:1:1 (SEQ ID NO:9) presented in Example 3, driving expression of Cre-recombinase and used to assess the ability and efficiency of autoexcision of the Cre-recombinase expression cassette and marker gene expression cassette.

A binary plant transformation construct as described in Example 4 was cloned using methods well known in the art. The EXP, EXP-At.Cdc45:1:1 (SEQ ID NO:9) was operably linked 5' to a synthetic coding sequence encoding Cre-recombinase (GOI-P1.Cre-St.LS1:1:1, SEQ ID NO:43), which was operably linked 5' to a 3' termination region (T-At.Cdc45:1, SEQ ID NO:12).

Cotton plant cells were transformed using the binary plant transformation constructs described above by *Agrobacterium*-mediated transformation. The resulting transformed plant cells were induced to form whole cotton plants under spectinomycin selection.

Selected $R_0$, single copy events were allowed to self-pollinate. The resulting $R_1$ plants were then analyzed for the presence of the Cre, aadA, and the GUS transgenes using a TAQMAN® assay. The zygosity of the GUS transgene cassette was also determined using a TAQMAN® assay. The percent GUS positive (GUS+) and marker free (aadA-) $R_1$ progeny for each of the selected $R_0$ events is presented in Table 9 below.

TABLE 9

Percent GUS positive (GUS+) and marker free (aadA-)
$R_1$ progeny in stably transformed cotton plants with
the Arabidopsis CDC45 promoter drives autoexcision.

| $R_0$ Event | Total $R_1$ Plants | GUS+/ aadA- | Homozygous GUS+/ aadA- | Percent GUS+/ aadA- | Percent Homozygous GUS+/ aadA- |
|---|---|---|---|---|---|
| Event-1 | 40 | 22 | 7 | 55% | 18% |
| Event-2 | 40 | 35 | 14 | 88% | 35% |
| Event-3 | 40 | 22 | 8 | 55% | 20% |
| Event-4 | 38 | 25 | 9 | 66% | 24% |
| Event-5 | 40 | 30 | 8 | 75% | 20% |
| Event-6 | 40 | 24 | 10 | 60% | 25% |
| Event-7 | 35 | 33 | 17 | 94% | 49% |
| Event-8 | 34 | 23 | 5 | 68% | 15% |
| Event-9 | 35 | 15 | 3 | 43% | 9% |
| Event-10 | 37 | 28 | 8 | 76% | 22% |
| Event-11 | 27 | 22 | 18 | 81% | 67% |
| Event-12 | 40 | 14 | 5 | 35% | 13% |
| Event-13 | 40 | 5 | 2 | 13% | 5% |
| Event-14 | 40 | 0 | 0 | 0% | 0% |
| Average | | 22.92 | 8.77 | 62.23% | 24.77% |

As can be seen in Table 9 above, all but one $R_0$ event (Event-14) gave rise to GUS positive (GUS+) and marker free (aadA-) $R_1$ progeny. Some $R_0$ events gave rise to a large percentage of marker free and homozygous marker free events, such as, Event-2, Event-7, and Event-11. The CDC45 promoter (P-At.Cdc45-1:1:1, SEQ ID NO:10) comprised within EXP-At.Cdc45:1:1 (SEQ ID NO:9) was able to efficiently drive autoexcision in stably transformed cotton plants.

Example 7

The Chimeric P-Vf.Usp88-chimera Promoter Drives Efficient Autoexcision in Stably Transformed Canola Plants Canola plants were transformed with a construct, specifically a plant binary transformation construct comprising the EXP, EXP-Vf.Usp88-enh:1:1 (SEQ ID NO:60) to drive expression of Cre-recombinase and used to assess the ability and efficiency of autoexcision of the Cre-recombinase expression cassette and a marker gene expression cassette. The EXP, EXP-Vf.Usp88-enh:1:1 (SEQ ID NO:60) is comprised of a chimeric promoter, P-Vf.Usp88-chimera (SEQ ID NO:61), operably linked 5' to the leader, L-Vf.Usp-1:1:1 (SEQ ID NO:62).

Canola plants were transformed with a binary plant transformation construct comprising three transgene expression cassettes; a Cre-recombinase expression cassette, and a selectable marker expression cassette for selection of transformed soybean cells (aadA) flanked by two LoxP sites (RS-P1.lox1:1, SEQ ID NO:44); and a third expression cassette outside of the LoxP sites used for the expression of the β-glucuronidase (GUS) transgene. The Cre-recombinase expression cassette was comprised of the EXP, EXP-Vf.Usp88-enh:1:1 (SEQ ID NO:60) operably linked 5' to a synthetic coding sequence encoding Cre-recombinase (GOI-P1.Cre-St.LS1:1:1, SEQ ID NO:43) containing a processable intron derived from the potato light-inducible tissue-specific ST-LS1 gene (GenBank Accession: X04753), operably linked 5' to a 3' termination region (T-Br.Snap2-1:3:6, SEQ ID NO:59). The transformation selectable marker cassette, aadA, was comprised of an EXP (EXP-At.Act7:2, SEQ ID NO:53), operably linked 5' to a coding sequence encoding a chloroplast targeted Tn7 adenylyltransferase (GOI-At.ShkG-CTP2+Ec.aadA-SPC/STR:1:1, SEQ ID NO:54) which confers spectinomycin resistance and used for the selection of transformed plant cells, operably linked 5' to a 3' termination region (T-AGRtu.nos:13, SEQ ID NO:48). The GUS transgene expression cassette was comprised of an enhanced Cauliflower mosaic virus 35S promoter and leader (EXP-CaMV.35S-enh:1:2, SEQ ID NO:55), operably linked 5' to a synthetic coding sequence encoding β-glucuronidase (GOI-Ec.uidA+St.LS1:3, SEQ ID NO:50) containing a processable intron derived from the potato light-inducible tissue-specific ST-LS1 gene (GenBank Accession: X04753), operably linked 5' to a 3' termination region (T-AGRtu.nos:13, SEQ ID NO:48).

Canola plant cells were transformed using the binary plant transformation construct described above by an *Agrobacterium*-mediated transformation, as is well known in the art. The resulting transformed plant cells were induced to form whole canola plants under spectinomycin (aadA) selection.

Selected $R_0$, single copy events were allowed to self-pollinate. The resulting $R_1$ seeds were then analyzed for the presence of the aadA and GUS transgenes using a TAQMAN® assay. Zygosity of the $R_1$ seeds for the integrated construct was also determined using a TAQMAN® assay of the GUS transgene. Eighty-eight $R_1$ seeds were assayed per each selected self-cross of an $R_0$ event. Table 10 below shows the number of hemizygous and homozygous GUS+/aadA-events observed for each event seed sample.

TABLE 10

Number and percent hemizygous and homozygous GUS+/aadA-
R1 progeny seed sampled in stably transformed canola plants with
the chimeric P-Vf.Usp88-chimera promoter driven autoexcision.

| Event | R1 Seeds Analyzed | Hemizygous GUS+/ aadA- | Homozygous GUS+/ aadA- | Percent Hemizygous GUS+/ aadA- | Percent Homozygous GUS+/ aadA- |
|---|---|---|---|---|---|
| Event-1 | 88 | 12 | 4 | 13.64% | 4.55% |
| Event-2 | 88 | 24 | 12 | 27.27% | 13.64% |
| Event-3 | 88 | 1 | 0 | 1.14% | 0.00% |
| Event-4 | 88 | 33 | 13 | 37.50% | 14.77% |
| Event-5 | 88 | 42 | 15 | 47.73% | 17.05% |
| Event-6 | 88 | 5 | 4 | 5.68% | 4.55% |
| Event-7 | 88 | 32 | 6 | 36.36% | 6.82% |
| Event-8 | 88 | 24 | 12 | 27.27% | 13.64% |

As can be seen in Table 9 above, all but one $R_0$ event (Event-3) gave rise to homozygous GUS positive (GUS+) and marker free (aadA-) $R_1$ progeny. Event-3 may have been a chimeric event with some cells being untransformed as occasionally happens in plant transformation. Some $R_0$ events gave rise to a large percentage of hemizygous marker free events, such as, Event-2, Event-4, Event-5, Event-7, and Event-8. The EXP, EXP-Vf.Usp88-enh:1:1 (SEQ ID NO:61) comprising the chimeric promoter, P-Vf.Usp88-chimera (SEQ ID NO:61) was able to efficiently drive autoexcision in stably transformed canola plants.

Example 8

EXP-Gm.Rsp-1:1 Drives Autoexcision of a Selectable Marker and Genome Editing Transgene Cassettes in Stably Transformed Soybean Plants Soybean plants were transformed with constructs, specifically plant binary transformation constructs comprising the EXP, EXP-Gm.Rsp-1:1 (SEQ ID NO:20) driving expression of Cre-recombinase and used to assess the ability and efficiency of autoexcision of the Cre-recombinase expression cassette, the marker gene expression cassette, and expression cassettes used for editing of the soybean genome.

Soybean plants were transformed with a binary plant transformation construct comprising five transgene expression cassettes; a Cre-recombinase expression cassette, a selectable marker expression cassette for selection of transformed soybean cells (aadA), an expression cassette used for the expression of the Cpf1 CRISPR associated nuclease, an expression cassette used for the expression of a guide RNA, flanked by two LoxP sites (RS-P1.lox1:1, SEQ ID NO:44); and a fifth expression cassette outside of the LoxP sites used for the expression of a gene of agronomic interest. The Cre-recombinase expression cassette was comprised of the EXP, EXP-Gm.Rsp-1:1 (SEQ ID NO:20), operably linked 5' to a synthetic coding sequence encoding Cre-recombinase (GOI-P1.Cre-St.LS1:1:1, SEQ ID NO:43) containing a processable intron derived from the potato light-inducible tissue-specific ST-LS1 gene (GenBank Accession: X04753), operably linked 5' to a 3' termination region (T-At.Cdc45:3, SEQ ID NO:23). The transformation selectable marker cassette, aadA, was comprised of an EXP (EXP-At.Act7:2, SEQ ID NO:54), operably linked 5' to a coding sequence encoding a chloroplast targeted Tn7 adenylyltransferase (GOI-At.ShkG-CTP2+Ec.aadA-SPC/STR:1:1, SEQ ID NO:54) which confers spectinomycin resistance and is used for the selection of transformed plant cells, operably linked 5' to a 3' termination region (T-AGRtu.nos:13, SEQ ID NO:48). The Cpf1 expression cassette was comprised of an EXP which provided constitutive expression, operably linked 5' to a nuclear targeted Cpf1 coding sequence, operably linked 5' to a 3' plant termination region. The guide RNA expression cassette was comprised of an RNA polymerase III promoter, operably linked 5' to a guide RNA encoding sequence, operably linked 5' to a 3' RNA polymerase III termination region. All four expression cassettes were flanked by LoxP sites. The fifth transgene expression cassette was comprised of a plant constitutive EXP, operably linked 5' to a coding sequence encoding a gene of agronomic interest, operably linked 5' to a 3' plant termination region.

The guide RNA transgene cassette comprised a guide RNA that was designed to provide site-specific integration of the construct in a specific location within the soybean genome. The construct was designed to provide autoexcision of the Cre, aadA, Cpf1, and guide RNA transgene expression cassettes after integration of the construct into the specific region of the soybean genome in the $R_1$ generation soybean seed. Following autoexcision, only the fifth transgene expression cassette used to express a gene of agronomic interest should remain in the $R_1$ generation transgenic soybean plants.

All $R_0$ transgenic events were assayed for transgene copy number. They were also analyzed for site-specific integration using a flank PCR assay wherein amplification was performed across the target site junction. The selected $R_0$ transgenic events were self-crossed to produce $R_1$ generation seed. Random samples of $R_1$ generation seed were assayed for the presence or absence of the marker and genome editing cassettes. Table 11 below shows the number and percent hemizygous and homozygous marker and genome editing cassette-free seeds derived from eight selected events.

TABLE 11

Number and percent hemizygous and homozygous marker and genome editing cassette-free R1 progeny seed sampled from stably transformed soybean plants with EXP-Gm.Rsp-1:1 Drives Autoexcision.

| Event | Total R1 Seed | Hemizygous M/GE-Free | Homozygous M/GE-Free | % Hemizygous M/GE-Free | % Homozygous M/GE-Free |
|---|---|---|---|---|---|
| Event-1 | 83 | 21 | 7 | 25% | 8% |
| Event-2 | 80 | 17 | 5 | 21% | 6% |
| Event-3 | 71 | 18 | 6 | 25% | 8% |
| Event-4 | 77 | 26 | 11 | 34% | 14% |
| Event-5 | 88 | 26 | 6 | 30% | 7% |
| Event-6 | 84 | 16 | 4 | 19% | 5% |
| Event-7 | 86 | 14 | 5 | 16% | 6% |
| Event-8 | 88 | 26 | 5 | 30% | 6% |

As can be seen in Table 11 above, the EXP, EXP-Gm.Rsp-1:1 (SEQ ID NO:20) was able to drive autoexcision of the marker and genome editing cassettes similar to the efficiency as demonstrated in Example 4 above.

Example 9

EXP-Gm.Nmh7:1 Drives Autoexcision of a Selectable Marker and Genome Editing Transgene Cassettes in Stably Transformed Soybean Plants Soybean plants were transformed with constructs, specifically plant binary transformation constructs comprising the EXP, EXP-Gm.Nmh7:1 (SEQ ID NO:64) driving expression of Cre-recombinase and used to assess the ability and efficiency of autoexcision of the Cre-recombinase expression cassette, the marker gene expression cassette, and expression cassettes used for editing of the soybean genome.

Soybean plants were transformed with binary plant transformation constructs comprising five transgene expression cassettes; a Cre-recombinase expression cassette, a selectable marker expression cassette for selection of transformed soybean cells (aadA), an expression cassette used for the expression of the Cpf1 CRISPR associated nuclease, an expression cassette used for the expression of a guide RNA, flanked by two LoxP sites (RS-P1.lox1:1, SEQ ID NO:44); and a fifth expression cassette outside of the LoxP sites used for the expression of a gene of agronomic interest. All of the expression cassettes were similar to those described in the previous Example 7. The Cre-recombinase expression cassette was comprised of the EXP, EXP-Gm.Nmh7:1 (SEQ ID NO:64), operably linked 5' to a synthetic coding sequence encoding Cre-recombinase (GOI-P1.Cre-St.LS1:1:1, SEQ ID NO:43) containing a processable intron derived from the potato light-inducible tissue-specific ST-LS1 gene (GenBank Accession: X04753), operably linked 5' to a 3' termination region (T-Gb.E6-3b:1:1, SEQ ID NO:67). Two different constructs were used in transformation. Each construct comprised a different constitutive promoter driving expression of the Cpf1 CRISPR associated nuclease.

All $R_0$ transgenic events were assayed for transgene copy number. They were also analyzed for site-specific integration using a flank PCR assay wherein amplification was performed across the target site junction. The selected $R_0$ transgenic events were self-crossed to produce $R_1$ generation seed. Random samples of $R_1$ generation seed were assayed for the presence or absence of the marker and genome editing cassettes. Tables 12 below shows the number and percent hemizygous and homozygous marker and genome editing cassette-free seeds derived from eight selected events.

TABLE 12

Number and percent hemizygous and homozygous marker and genome editing
cassette-free R1 progeny seed sampled from stably transformed
soybean plants with EXP-Gm.Nmh7:1 Drives Autoexcision.

| Construct | Event | Total R1 Seed | Hemizygous M/GE-Free | Homozygous M/GE-Free | % Hemizygous M/GE-Free | % Homozygous M/GE-Free |
|---|---|---|---|---|---|---|
| Construct-1 | Event-1 | 154 | 27 | 0 | 17% | 0% |
| | Event-2 | 64 | 11 | 3 | 17% | 5% |
| | Event-3 | 170 | 0 | 0 | 0% | 0% |
| Construct-2 | Event-1 | 173 | 7 | 0 | 4% | 0% |
| | Event-2 | 143 | 0 | 0 | 0% | 0% |
| | Event-3 | 176 | 20 | 0 | 11% | 0% |

As can be seen in Table 12 above, two events derived from transformations using each construct gave rise to hemizygous marker and genome editing cassette-free $R_1$ progeny. Event 2 derived from transformation using Construct-1 even gave rise to several homozygous marker and genome editing cassette-free $R_1$ progeny.

Example 10

Autoexcision of Selectable Marker and Genome Editing Transgene Cassettes in Stably Transformed Corn Plants using The *Zea mays* and *Oryza sativa* CDC45-1 Promoters to Drive Autoexcision Corn plants are transformed with constructs, specifically plant binary transformation constructs comprising EXP-Zm.Cdc45-1+Zm.DnaK:1:1 (SEQ ID NO:1) or EXP-Os.Cdc45-1:1:1 (SEQ ID NO:4) driving expression of Cre-recombinase.

Corn plants are transformed with constructs comprising at least five expression cassettes. The construct comprises a Cre-recombinase expression cassette, at least one selectable marker cassette, an expression cassette used for the expression of a CRISPR associated nuclease such as Cpf1, at least one guide RNA cassette; all of which are flanked by a LoxP site. The construct also comprises at least one expression cassette outside of the LoxP sites that is used for expression of a gene of agronomic interest. Each construct comprises a Cre-recombinase expression cassette similar to that described in Example 2, wherein either EXP-Zm.Cdc45-1+Zm.DnaK:1:1 (SEQ ID NO:1) or EXP-Os.Cdc45-1:1:1 (SEQ ID NO:4) is used to drive expression of Cre-recombinase.

Corn plants are transformed with either of the two constructs and $R_0$ transgenic events are selected using molecular assays to determine copy number, insert intactness. If the constructs are designed to provide site-specific integration of the construct; confirmation of the insertion location within the corn genome is confirmed by amplification of the insertion site junctions. The selected $R_0$ transgenic events are self-crossed to generate $R_1$ generation seed. The seed or germinated progeny are analyzed for the removal of the Cre, marker, Cpf1, and guide RNA cassettes. They are also analyzed for the presence of the expression cassette or cassettes for the gene or genes of agronomic interest.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA construct comprising a DNA regulatory sequence selected from the group consisting of:
   a) a sequence with at least 95 percent sequence identity to SEQ ID NO:20 or 21 and having promoter activity;
   b) a sequence comprising SEQ ID NO:20 or 21; and
   c) a fragment comprising at least 250 contiguous nucleo- tides of SEQ ID NO:20 or 21, wherein the fragment has promoter activity;

wherein said DNA regulatory sequence is operably linked to a heterologous transcribable DNA sequence encoding a site-specific recombinase.

2. The recombinant DNA construct of claim 1, wherein said DNA regulatory sequence has at least 97 percent sequence identity to the DNA sequence of SEQ ID NO: 20 or 21 and having promoter activity.

3. The recombinant DNA construct of claim 1, wherein said DNA regulatory sequence has at least 99 percent sequence identity to the DNA sequence of SEQ ID NO: 20 or 21 and having promoter activity.

4. The recombinant DNA construct of claim 1 wherein said DNA regulatory sequence has promoter activity.

5. The recombinant DNA construct of claim 1, wherein said DNA regulatory sequence is a germline-preferred promoter.

6. The recombinant DNA construct of claim 5, wherein said germline-preferred promoter comprises a sequence of SEQ ID NO:21, or a sequence with at least 95 percent sequence identity to SEQ ID NO:21.

7. The recombinant DNA construct of claim 1, wherein said site-specific recombinase is selected from the group consisting of a Cre-recombinase, a Flp-recombinase, an R-recombinase, and a Gin-Recombinase.

8. The recombinant DNA construct of claim 1, wherein said site-specific recombinase is a Cre-recombinase.

9. The recombinant DNA construct of claim 1, further comprising:
   a) an expression cassette comprising a selectable marker transgene; and/or an expression cassette comprising a transgene of agronomic interest;
   b) a pair of site-specific recombination site sequences flanking one or both of the transcribable DNA sequences encoding the site-specific recombinase and/ or the selectable marker transgene, wherein the site-specific recombination sites can be cleaved by the site-specific recombinase; or
   c) an expression cassette encoding a guide RNA; and/or an expression cassette encoding a site-specific nuclease.

10. The recombinant DNA construct of claim 9, wherein:
   a) said pair of site-specific recombination site sequences are oriented in a head-to-tail arrangement;
   b) said selectable marker transgene confers resistance to an herbicide or antibiotic;
   c) said pair of site-specific recombination site sequences are each selected from the group consisting of LoxP, Lox.TATA-R9, FRT, RS, and GIX;
   d) said pair of site-specific recombination site sequences are each a LoxP or Lox.TATA-R9 site;
   e) said pair of site-specific recombination site sequences each comprise SEQ ID NO: 44 or SEQ ID NO: 45;
   f) said transgene of agronomic interest confers herbicide tolerance in plants;
   g) said transgene of agronomic interest confers pest or disease resistance in plants;
   h) said transgene of agronomic interest confers increased yield or stress tolerance in plants;
   i) said transgene of agronomic interest encodes a dsRNA, a miRNA, or and siRNA;
   j) said guide RNA comprises a targeting sequence that targets a sequence in the genome of a eukaryotic cell for genome editing or site-specific integration;
   k) said site-specific nuclease is a RNA-guided endonuclease; or
   l) said site-specific is a RNA-guided endonuclease selected from the group consisting of Cas1, Cas1B, Cas2, Cas3, Cas4, Cas5, Cas6, Cas7, Cas8, Cas9, Cas10, Cpf1, Cys1, Cys2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, and CasY.

11. The recombinant DNA construct of claim 9, further comprising:
   a) a pair of site-specific recombination site sequences flanking one or more of the transcribable DNA sequence encoding the site-specific recombinase, the selectable marker transgene, the expression cassette encoding the guide RNA, and/or the expression cassette encoding the site-specific nuclease, wherein the site-specific recombination sites can be cleaved by the site-specific recombinase;
   b) two or more expression cassettes encoding two or more guide RNAs; and/or
   c) two, three, four, five, six, seven, eight, nine, or ten different expression cassettes encoding guide RNAs.

12. The recombinant DNA construct of claim 10, wherein:
   a) said eukaryotic cell is a plant cell; and/or
   b) said RNA-guided endonuclease is Cas9 or Cpf1.

13. A DNA molecule, DNA vector, or DNA transformation vector comprising:
   a) the recombinant DNA construct of claim 1; or
   b) the recombinant DNA construct of claim 1 and a T-DNA segment bounded by a left border and right border.

14. The DNA transformation vector of claim 13, wherein said transcribable DNA sequence encoding the site-specific recombinase is located between the left border and the right border of the T-DNA segment.

15. A DNA transformation vector comprising the recombinant DNA construct of claim 9 and a T-DNA segment with a left border and a right border, wherein:
   a) one or more of the transcribable DNA sequences encoding the site-specific recombinase, the selectable marker transgene, and/or the transgene of agronomic interest is/are located between the left border and the right border of the T-DNA segment; or
   b) one or more of the transcribable DNA sequences encoding the site-specific recombinase, the selectable marker transgene, the transgene of agronomic interest, the expression cassette encoding the guide RNA and/or the expression cassette encoding the site-specific nuclease is/are located between the left border and the right border of the T-DNA segment.

16. A transgenic plant, plant part or plant cell comprising the recombinant DNA construct of claim 1.

17. The transgenic plant, plant part, or plant cell of claim 16, wherein:
   a) said recombinant DNA construct is stably transformed into the genome of the transgenic plant, plant part, or plant cell; or
   b) said transgenic plant, plant part, or plant cell is a corn, soybean, cotton, or canola plant, plant part or plant cell.

18. A method for producing a transgenic plant or plant part, comprising:
   a) transforming a plant cell of an explant with a DNA molecule or vector comprising the recombinant DNA construct of claim 1 to produce one or more transformed plant cells comprising the recombinant DNA construct stably transformed into the genome of the one or more transformed plant cells; and
   b) regenerating or developing a transgenic plant from the explant, wherein the transgenic plant comprises the recombinant DNA construct stably transformed into the genome of one or more cells of the transgenic plant.

19. The method of claim 18, wherein:
   a) said plant cell is transformed via *Agrobacterium*-mediated transformation or *Rhizobium*-mediated transformation;

b) said plant cell is transformed via microprojectile-mediated transformation or particle bombardment-mediated transformation;

c) said transgenic plant and plant cell are a corn, soybean, cotton, or canola plant and plant cell, respectively; and/or d) the method further comprises: separating or harvesting a plant part from the transgenic plant.

20. A method for excising an expression cassette from the genome of a transgenic plant, comprising:

a) transforming a plant cell with a DNA molecule or vector comprising the recombinant DNA construct of claim 12 to produce one or more transformed plant cells comprising the recombinant DNA construct stably transformed into the genome of the one or more transformed plant cells;

b) regenerating or developing a transgenic plant at least in part from the one or more stably transformed plant cells;

c) crossing the transgenic plant with itself or another plant; and d) selecting one or more progeny plants in which one or both of the transcribable DNA sequence encoding the site-specific recombinase and/or the selectable marker transgene between the pair of site-specific recombination site sequences of the recombinant DNA construct are excised and no longer present in the genome of the one or more progeny plants.

21. The method of claim 20, wherein:

a) said recombinant DNA construct further comprises one or both of the following expression cassettes between the pair of DNA site-specific recombination site sequences of the recombinant DNA construct: an expression cassette encoding a guide RNA and/or an expression cassette encoding a site-specific nuclease, and wherein one or more progeny plants are selected in which one or more of the transcribable DNA sequence encoding the site-specific recombinase, the selectable marker transgene, the expression cassette encoding the guide RNA, and/or the expression cassette encoding the site-specific nuclease of said recombinant DNA construct are excised and no longer present in the genome of the one or more progeny plants; and/or b) said transgenic plant and plant cell are a corn, soybean, cotton, or canola plant and plant cell, respectively.

22. The method of claim 20, further comprising:

a) separating or harvesting a plant part from one or more of the progeny plants; and/or b) crossing one or more of the progeny plants to itself or another plant.

23. A bacterial cell comprising the recombinant DNA construct of claim 1.

24. A bacterial cell comprising the DNA molecule, DNA vector, or DNA transformation vector of claim 13.

25. The recombinant DNA molecule of claim 1, wherein said sequence has at least 95 percent sequence identity to SEQ ID NO:21 and has promoter activity.

26. The recombinant DNA molecule of claim 1, wherein said sequence comprises SEQ ID NO: 21.

27. The recombinant DNA molecule of claim 1, wherein said fragment comprises at least 250 contiguous nucleotides of SEQ ID NO:21, and wherein said fragment has promoter activity.

* * * * *